(12) United States Patent
Kim et al.

(10) Patent No.: US 12,156,881 B2
(45) Date of Patent: *Dec. 3, 2024

(54) ORAL (17-β)-3-OXOANDROST-4-EN-17-YL TRIDECANOATE THERAPY

(71) Applicant: Lipocine Inc., Salt Lake City, UT (US)

(72) Inventors: Kilyoung Kim, Salt Lake City, UT (US); Mahesh V. Patel, Salt Lake City, UT (US); Nachiappan Chidambaram, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 18/437,405

(22) Filed: Feb. 9, 2024

(65) Prior Publication Data

US 2024/0245708 A1 Jul. 25, 2024

Related U.S. Application Data

(63) Continuation of application No. 17/490,866, filed on Sep. 30, 2021, now Pat. No. 11,931,367.

(51) Int. Cl.
A61K 31/568 (2006.01)
A61K 9/00 (2006.01)
G16H 20/10 (2018.01)

(52) U.S. Cl.
CPC .......... A61K 31/568 (2013.01); A61K 9/0053 (2013.01); G16H 20/10 (2018.01)

(58) Field of Classification Search
CPC .................................................. A61K 31/568
See application file for complete search history.

(56) References Cited

U.S. PATENT DOCUMENTS

| | | | | |
|---|---|---|---|---|
| 9,034,858 B2 | 5/2015 | Giliyar | | A61K 31/568 |
| 9,205,057 B2 | 12/2015 | Giliyar | | A61K 9/4858 |
| 9,480,690 B2 | 11/2016 | Giliyar | | A61K 31/568 |
| 10,881,670 B2 | 1/2021 | Chidambaram | | A61K 31/568 |
| 10,973,833 B2 | 4/2021 | Giliyar | | A61K 31/568 |
| 11,370,811 B1 | 6/2022 | Kim | | C07J 9/005 |
| 11,672,807 B1 | 6/2023 | Chidambaram | | A61K 31/568 |
| 11,931,367 B2 * | 3/2024 | Kim | | A61K 31/568 |
| 2012/0244215 A1 | 9/2012 | Giliyar | | 424/452 |
| 2015/0224059 A1 | 8/2015 | Giliyar | | A61K 9/4858 |
| 2015/0320765 A1 | 11/2015 | Giliyar | | A61K 31/568 |
| 2016/0074416 A1 | 3/2016 | Giliyar | | A61K 31/568 |
| 2017/0007622 A1 | 1/2017 | Giliyar | | A61K 31/568 |
| 2018/0153905 A1 | 6/2018 | Chidambaram | | A61K 31/568 |
| 2020/0155570 A1 | 5/2020 | Patel | | A61K 31/568 |
| 2020/0222426 A1 | 7/2020 | Chidambaram | | A61K 31/568 |

* cited by examiner

*Primary Examiner* — Rei Tsang Shiao
(74) *Attorney, Agent, or Firm* — Michael R. Schramm

(57) ABSTRACT

Disclosed are pharmaceutical compositions and oral dosage forms including capsules containing (17-ß)-3-oxoandrost-4-en-17-yl tridecanoate, and related methods. The capsule fill can include an additive and about 14 wt % to about 42 wt % for androst-4-en-17β-ol-3-one esters that comprise (17-ß)-3-oxoandrost-4-en-17-yl tridecanoate or a combination of (17-ß)-3-oxoandrost-4-en-17-yl undecanoate, (17-ß)-3-oxoandrost-4-en-17-yl dodecanoate, and (17-ß)-3-oxoandrost-4-en-17-yl tridecanoate. A single oral administration to a male subject of one or more dosage forms with a total androst-4-en-17β-ol-3-one equivalent dose of about 150 mg to about 895 mg is provided. In another embodiment, a method for providing a serum concentration of androst-4-en-17β-ol-3-one within a target PK performance for a male subject is provided. In a further embodiment, the pharmaceutical compositions and methods comprising androst-4-en-17β-ol-3-one ester loading of 14 wt % to 42 wt % achieve androst-4-en-17β-ol-3-one PK performance targets and require titration(s) to show therapeutic effectiveness for treatment of hypogonadism.

31 Claims, 9 Drawing Sheets

ORAL (17-ß)-3-OXOANDROST-4-EN-17-YL TRIDECANOATE THERAPY

CROSS REFERENCE TO RELATED APPLICATIONS

This nonprovisional utility patent application is a continuation of and claims the benefit under 35 USC § 120 to allowed co-pending U.S. application Ser. No. 17/490,866 filed Sep. 30, 2021 and published on Apr. 13, 2023 as US 20230113311, which is incorporated herein in its entirety by this reference.

FIELD OF THE INVENTION

The present invention relates to (17-ß)-3-oxoandrost-4-en-17-yl tridecanoate (IUPAC name: [(8R,9S,10R,13S,14S,17S)-10,13-dimethyl-3-oxo-1,2,6,7,8,9,11,12,14,15,16,17-dodecahydrocyclopenta[a]phenanthren-17-yl] tridecanoate) containing pharmaceutical compositions and oral dosage units as well as associated methods. Accordingly, this invention involves the fields of chemistry, pharmaceutical sciences, medicine and other health sciences.

BACKGROUND OF THE INVENTION

Male hypogonadism is a serious condition affecting mostly aging men. References directed to the treatment of hypogonadism include the following US patents and applications which are expressly incorporated herein by reference: U.S. Pat. No. 9,034,858 to Giliyar et al., U.S. Pat. No. 9,205,057 to Giliyar et al., U.S. Pat. No. 9,480,690 to Giliyar et al., U.S. Pat. No. 10,881,670 to Chidambaram et al., U.S. Pat. No. 10,973,833 to Giliyar et al., 20120244215 to Giliyar et al., 20150224059 to Giliyar et al., 20150320765 to Giliyar et al., 20160074416 to Giliyar et al., 20170007622 to Giliyar et al., 20180153905 to Chidambaram et al., and 20200222426 to Chidambaram et al. The common reasons for hypogonadism in men could be physiological abnormality involving among other factors, improper functioning or growth of the gonads and/or the pituitary-hypothalamus regulatory systems, and aging. Many of the abnormalities that are identified to be commonly associated with the low or decreased androst-4-en-17β-ol-3-one, commonly known as testosterone, levels include impaired sexual function and/or libido, metabolic syndrome which may be a combination of abdominal obesity, high blood pressure, insulin resistance, lipid disorders; high risk of cardiovascular diseases; reduced bone mass/mineral density and muscle weakness and or degeneration affecting the musculoskeletal system. Other effects of low androst-4-en-17β-ol-3-one levels include negative changes in body composition, depression and other psychological disorders. The average human male produces 4-7 mg of androst-4-en-17β-ol-3-one per day in a circadian pattern, with maximal plasma levels attained in early morning and minimal levels in the evening. It is generally recognized that in a normal adult man, the serum total androst-4-en-17β-ol-3-one is between about 300 ng/dL to about 1100 ng/dL and this range is referred to as the eugonadal range which may vary depending on the specific assay employed including blood sample matrix. Restoration of androst-4-en-17β-ol-3-one levels to the eugonadal range typically corrects many of the cited clinical abnormalities associated with hypogonadism or low androst-4-en-17β-ol-3-one levels.

While oral administration is the most preferred and patient friendly route for administration, the effective oral delivery of androst-4-en-17β-ol-3-one as androst-4-en-17β-ol-3-one and its esters remains a challenge. This is due to extremely poor bioavailability of androst-4-en-17β-ol-3-one, which requires very high dosing as well as frequent dosing due to the short serum half-life. These problems with orally administered androst-4-en-17β-ol-3-one products are primarily due to first pass metabolism.

Currently, modified androst-4-en-17β-ol-3-ones, in form of a methyl analogue of androst-4-en-17β-ol-3-one, and as a undecanoate ester, are available for oral administration for patients in need of androst-4-en-17β-ol-3-one therapy. However, liver damage including cholestasis, peliosis hepatitis, nodular regenerative hyperplasia, and primary hepatic tumors has been reported with use of methyl androst-4-en-17β-ol-3-one. (17-ß)-3-oxoandrost-4-en-17-yl undecanoate is a prodrug which gets converted to androst-4-en-17β-ol-3-one in vivo but requires multiple administrations per day. Therefore, there remains a need for compositions and methods to enable a patient friendly administration of an oral composition for androst-4-en-17β-ol-3-one therapy with less dosing frequency, and a patient customized adjustable dosing that effectively restores androst-4-en-17β-ol-3-one levels in subjects in need of androst-4-en-17β-ol-3-one.

(17-ß)-3-oxoandrost-4-en-17-yl tridecanoate, an androst-4-en-17β-ol-3-one ester, is extremely lipophilic and practically insoluble in water, and has a melting point about 70-75° C. with low oral bioavailability. (17-ß)-3-oxoandrost-4-en-17-yl tridecanoate has unique physico-chemical, pharmacokinetic, and pharmacodynamic properties relative to other androst-4-en-17β-ol-3-one esters known in the art presenting unique challenges to develop desirable dosing frequency such as once daily method and compositions. Furthermore, compositions and methods using principally crystalline (17-ß)-3-oxoandrost-4-en-17-yl tridecanoate, especially particles not subjected to comminution, are not expected to provide effective absorption of the (17-ß)-3-oxoandrost-4-en-17-yl tridecanoate ester due to very low bioavailability resulting in sub therapeutic restoration of androst-4-en-17β-ol-3-one even at high doses. A hypogonadal patient may be a super or poor absorber leading to super or poor response and responder rates resulting in sub (androst-4-en-17β-ol-3-one $C_{avg}$<300 ng/dL) or supra therapeutic (androst-4-en-17β-ol-3-one $C_{max}$>2.5×ULN: ULN=upper limit of normal lab range) blood levels on a non-adjustable dosing regimen, possibly leading to erroneous discontinuation of the therapy in subjects in need to therapy. Prior art oral compositions and methods involving dosing regimens requiring dose adjustment or titration to treat androst-4-en-17β-ol-3-one deficiency teach either a low initial dose and/or dose adjustments of smaller increments from the initial dose resulting in compromised pharmacokinetic performance in a patient group population. It is noted that pharmacokinetic performance in a patient group population is a regulatory requirement for marketing. The oral titration dosing regimen for an approved fully solubilized (17-ß)-3-oxoandrost-4-en-17-yl undecanoate composition (e.g., JATENZO) with the initial dose of 237 mg requires twice daily dosing.

Currently no dosage forms or adjustable dosing regimens are approved for oral compositions comprising (17-ß)-3-oxoandrost-4-en-17-yl tridecanoate, which is a unique prodrug of androst-4-en-17β-ol-3-one. Therefore, (17-ß)-3-oxoandrost-4-en-17-yl tridecanoate needs to be formulated in a composition comprising a carrier, and needs to be administered via a dosing regimen that enables effective oral absorption of the (17-ß)-3-oxoandrost-4-en-17-yl tridecanoate so as to result in a restoration of androst-4-en-17β-ol- 3-one levels to a eugonadal range in an acceptable majority of a group of hypogonadal patients. Accordingly, research continues into the development of (17-ß)-3-oxoandrost-4-en-17-yl tridecanoate oral delivery products that can provide for a practical unit dosing regimen with oral dosage forms that allow for dose adjustment and can provide therapeutically effective amounts of total androst-4-en-17β-ol-3-one in a subject in need of androst-4-en-17β-ol-3-one treatment.

Typically, titration based dosing regimen pivotal clinical trials for regulatory approval for androst-4-en-17β-ol-3-one replacement therapy include multiple pharmacokinetic sampling based assessments of androst-4-en-17β-ol-3-one levels, titration iterations, and associated $C_{avg}$ and/or $C_{max}$ targets after a single dose administration. However, in clinical practice a single point based assessment and titration iteration are employed based on a relationship between an androst-4-en-17β-ol-3-one level range measured at a single point and the full pharmacokinetic profile.

SUMMARY OF THE INVENTION

The present disclosure is drawn to pharmaceutical compositions and oral dosage units containing (17-ß)-3-oxoandrost-4-en-17-yl tridecanoate, as well as related methods.

In one embodiment, pharmaceutical compositions and oral dosage units containing (17-ß)-3-oxoandrost-4-en-17-yl tridecanoate and related methods are provided that comprise a dosing regimen having an adjustable dose. In one aspect, the dosing regimen comprises an initial dose that provides a base for subsequent titration (increase or decrease) to result in a maintenance dosage. The titration sequence may be repeated (performed) up to two or three times, if/as needed to achieve the subject and/or the group $C_{avg}$ and $C_{max}$ targets. The $C_{avg}$ and $C_{max}$ targets are preferably based on serum or plasma androst-4-en-17β-ol-3-one measurements taken at a steady state after a single dose administration of a maintenance dose after completion of titration as needed.

In another aspect, the dosing regimen comprises an initial dose that provides a base for subsequent titration (increase or decrease) to result in a maintenance dosage. The titration sequence may be repeated (performed) up to two or three times, if/as needed to achieve the $C_{avg}$ and $C_{max}$ targets. The $C_{avg}$ and $C_{max}$ targets are preferably based on at least a single serum or plasma androst-4-en-17β-ol-3-one measurement taken at a steady state after a single dose administration, in order to provide therapeutically effective amounts of total androst-4-en-17β-ol-3-one in a subject in need of androst-4-en-17β-ol-3-one treatment.

In another aspect, the dosing regimen comprises an initial dose that provides a base for subsequent titration (increase or decrease) to result in a maintenance dosage. The titration sequence may be repeated (performed) up to two or three times, if needed, to achieve the $C_{avg}$ and $C_{max}$ targets in a hypogonadal subject or a group of subjects. The $C_{avg}$ and $C_{max}$ targets are preferably based on at least a single serum or plasma androst-4-en-17β-ol-3-one measurement taken at a steady state after a single dose administration, in order to provide a $C_{avg}$ responder rate of at least 75% of the subjects based on amounts of total androst-4-en-17β-ol-3-one in the group of hypogonadal subjects in need of androst-4-en-17β-ol-3-one treatment.

In another aspect, the dosing regimen comprises an initial dose that provides a base for subsequent titration (increase or decrease) to result in a maintenance dosage. The titration sequence may be repeated (performed) up to two or three times, if needed, to achieve the $C_{avg}$ and $C_{max}$ targets in a hypogonadal subject or a group of subjects. The $C_{avg}$ and $C_{max}$ targets are preferably based on at least a single serum or plasma androst-4-en-17β-ol-3-one measurement taken at a steady state after single dose administration, in order to avoid excessive androst-4-en-17β-ol-3-one repletion (e.g. no more than 3% of subjects in $C_{max}$ of greater than 2.5 times the upper limit of normal lab range: 2.5×ULN) based on amounts of total androst-4-en-17β-ol-3-one in the group of hypogonadal subjects in need of androst-4-en-17β-ol-3-one treatment.

In another aspect, the dosing regimen comprises an initial dose that provides a base for subsequent titration (increase or decrease) to result in a maintenance dosage. The titration sequence may be repeated (performed) up to two or three times, if needed, to achieve the $C_{avg}$ and $C_{max}$ targets in a hypogonadal subject or a group of subjects. The $C_{avg}$ and $C_{max}$ targets are preferably based on at least a single serum or plasma androst-4-en-17β-ol-3-one measurement taken at a steady state after single dose administration, in order to provide a $C_{avg}$ responder rate of at least 75% of the subjects based on a titration metric in the group of hypogonadal subjects in need of androst-4-en-17β-ol-3-one treatment.

In another aspect, the dosing regimen comprises an initial dose that provides a base for subsequent titration (increase or decrease) to result in a maintenance dosage. The titration sequence may be repeated (performed) up to two or three times, if needed, to achieve the $C_{avg}$ and $C_{max}$ targets in a hypogonadal subject or a group of subjects. The $C_{avg}$ and $C_{max}$ targets are preferably based on at least a single serum or plasma androst-4-en-17β-ol-3-one measurement taken at a steady state after single dose administration, in order to avoid excessive androst-4-en-17β-ol-3-one repletion (e.g. $C_{max}$>2.5×ULN of no more than 3% of subjects) based on a titration metric in the group of hypogonadal subjects in need of androst-4-en-17β-ol-3-one treatment.

In one embodiment, androst-4-en-17β-ol-3-one ester pharmaceutical compositions and oral dosage units containing (17-ß)-3-oxoandrost-4-en-17-yl tridecanoate and related methods are provided that comprise a dosing regimen having an adjustable dose. In one aspect, the dosing regimen comprises an initial dose that provides a base for subsequent titration (increase or decrease) to result in a maintenance dosage. The titration sequence may be repeated (performed) up to two or three times, if/as needed, to achieve the $C_{avg}$ and $C_{max}$ targets in hypogonadal subjects or a group of subjects based on at least a single serum or plasma androst-4-en-17β-ol-3-one measurement taken at a steady state after single dose administration to provide therapeutically effective amounts of total androst-4-en-17β-ol-3-one in a subject in need of androst-4-en-17β-ol-3-one treatment. The initial dose is preferably 250 mg to 1500 mg of (17-ß)-3-oxoandrost-4-en-17-yl tridecanoate if the androst-4-en-17β-ol-3-one ester is substantially (17-ß)-3-oxoandrost-4-en-17-yl tridecanoate.

In one embodiment, pharmaceutical compositions and oral dosage units containing androst-4-en-17β-ol-3-one esters (a combination of (17-ß)-3-oxoandrost-4-en-17-yl tridecanoate and at least one of (17-ß)-3-oxoandrost-4-en-17-yl undecanoate and (17-ß)-3-oxoandrost-4-en-17-yl dodecanoate) and related methods are provided that comprise a dosing regimen with adjustable dose. In one aspect, the dosing regimen comprises an initial dose that provides a base for subsequent titration (increase or decrease) to result in a maintenance dosage The titration sequence may be repeated (performed) up to two or three times, if/as needed to achieve the $C_{avg}$ and $C_{max}$ targets. The $C_{avg}$ and $C_{max}$ targets are preferably based on at least a single serum or plasma androst-4-en-17β-ol-3-one measurement taken at a steady state after a single dose administration to provide therapeutically effective amounts of total androst-4-en-17β-ol-3-one in a subject in need of androst-4-en-17β-ol-3-one treatment. The initial dose is preferably 149 mg to 893 mg of an androst-4-en-17β-ol-3-one equivalent amount.

In one embodiment, androst-4-en-17β-ol-3-one ester pharmaceutical compositions and oral dosage units containing (17-ß)-3-oxoandrost-4-en-17-yl tridecanoate and related methods are provided that comprise a dosing regimen with adjustable dose. In one aspect, the dosing regimen comprises an initial dose that provides a base for subsequent titration (increase or decrease) to result in a maintenance dosage. The titration sequence may be repeated (performed) up to two or three times, if/as needed, to achieve the $C_{avg}$ and $C_{max}$ targets. The $C_{avg}$ and $C_{max}$ targets are preferably based on at least a single serum or plasma androst-4-en-17β-ol-3-one measurement taken at a steady state after a single dose administration, in order to provide therapeutically effective amounts of total androst-4-en-17β-ol-3-one in a subject in need of androst-4-en-17β-ol-3-one treatment. The titrated dose and maintenance dose are preferably within from 250 mg to 1500 mg of (17-ß)-3-oxoandrost-4-en-17-yl tridecanoate if the androst-4-en-17β-ol-3-one ester is substantially (17-ß)-3-oxoandrost-4-en-17-yl tridecanoate.

In one embodiment, pharmaceutical compositions and oral dosage units containing androst-4-en-17β-ol-3-one esters (a combination of (17-ß)-3-oxoandrost-4-en-17-yl tridecanoate and at least one of (17-ß)-3-oxoandrost-4-en-17-yl undecanoate and (17-ß)-3-oxoandrost-4-en-17-yl dodecanoate) and related methods are provided that comprise a dosing regimen with adjustable dose. In one aspect, the dosing regimen comprises an initial dose that provides a base for subsequent titration (increase or decrease) to result in a maintenance dosage. The titration sequence may be repeated (performed) up to two or three times, if/as needed, to achieve the $C_{avg}$ and $C_{max}$ targets. The $C_{avg}$ and $C_{max}$ targets are preferably based on at least a single serum or plasma androst-4-en-17β-ol-3-one measurement taken at a steady state after single dose administration, in order to provide therapeutically effective amounts of total androst-4-en-17β-ol-3-one in a subject in need of androst-4-en-17β-ol-3-one treatment. The titrated dose and maintenance dose are preferably any amount between 149 mg and 893 mg of an androst-4-en-17β-ol-3-one equivalent amount.

In one aspect, androst-4-en-17β-ol-3-one ester in the pharmaceutical compositions and oral dosage units comprises at least 25 w/w % for (17-ß)-3-oxoandrost-4-en-17-yl tridecanoate per the amount of total androst-4-en-17β-ol-3-one ester. The initial dose or the titrated dose, if need, preferably can comprise any amount of (17-ß)-3-oxoandrost-4-en-17-yl tridecanoate between 62.5 mg and 1500 mg.

In one aspect, the total equivalent amount of (17-ß)-3-oxoandrost-4-en-17-yl tridecanoate of the androst-4-en-17β-ol-3-one ester in the pharmaceutical compositions and oral dosage units comprises at least one of 25 w/w %, 30 w/w %, 40 w/w %, 50 w/w %, 60 w/w %, 70 w/w %, 80 w/w %, 90 w/w %, and 100 w/w %.

In one embodiment, a pharmaceutical capsule for oral delivery is provided. The capsule includes a capsule shell and a capsule fill. The capsule fill can include an additive and about 14 wt % to about 42 wt % for (17-ß)-3-oxoandrost-4-en-17-yl tridecanoate based on the total weight of the capsule fill if the androst-4-en-17β-ol-3-one ester is substantially (17-ß)-3-oxoandrost-4-en-17-yl tridecanoate. In some aspects, the oral dosage capsule is preferably such that upon a single oral administration to a male subject of one or more capsules with a total (17-ß)-3-oxoandrost-4-en-17-yl tridecanoate dose of about 250 mg to about 1500 mg if the androst-4-en-17β-ol-3-one ester is substantially (17-ß)-3-oxoandrost-4-en-17-yl tridecanoate.

In one aspect, the capsule fill can include an additive and about 14 wt % to about 42 wt % for androst-4-en-17β-ol-3-one ester based on the total weight of the capsule fill. In some aspects, the oral dosage capsule is preferably such that a single oral administration to a male subject of one or more capsules will provide an androst-4-en-17β-ol-3-one total equivalent amount of between about 149 mg and about 893 mg.

In another embodiment, a method for providing a serum concentration of androst-4-en-17β-ol-3-one within the eugonadal range based on a $C_{avg}$ of androst-4-en-17β-ol-3-one for a male subject is provided. The method can include the step of orally administering a dose of androst-4-en-17β-ol-3-one ester containing composition to the male subject. The androst-4-en-17β-ol-3-one ester preferably comprises a (17-ß)-3-oxoandrost-4-en-17-yl tridecanoate or a combination of (17-ß)-3-oxoandrost-4-en-17-yl tridecanoate and at least one of (17-ß)-3-oxoandrost-4-en-17-yl undecanoate and (17-ß)-3-oxoandrost-4-en-17-yl dodecanoate, and can comprise about 14 wt % to about 42 wt % in the composition. The dose preferably provides any amount between about 250 mg and about 893 mg of an androst-4-en-17β-ol-3-one total equivalent amount to the male subject.

In yet a further embodiment, a method for providing a serum concentration of androst-4-en-17β-ol-3-one within a target serum androst-4-en-17β-ol-3-one concentration $C_{avg}$ range for a male subject is provided. The method can include the step of orally administering an initial dose of a (17-ß)-3-oxoandrost-4-en-17-yl tridecanoate containing composition to the male subject. The androst-4-en-17β-ol-3-one ester preferably comprises about 14 wt % to about 42 wt % in the (17-ß)-3-oxoandrost-4-en-17-yl tridecanoate containing composition and the initial dose preferably provides any amount between about 250 mg and about 893 mg of an androst-4-en-17β-ol-3-one total equivalent amount to the male subject. After the initial dose, the method may include a step of determining the serum androst-4-en-17β-ol-3-one concentration for the male subject on at least one titration node day after reaching a steady state to arrive at a maintenance dosage, if/as needed. The method further may include the step of orally administering to the male subject a titrated dose or a maintenance dose of the (17-ß)-3-oxoandrost-4-en-17-yl tridecanoate containing composition that comprises about 14 wt % to about 42 wt % of an androst-4-en-17β-ol-3-one ester. The titrated dose or maintenance dose may provide a dose of an androst-4-en-17β-ol-3-one total equivalent amount to the subject based on the serum androst-4-en-17β-ol-3-one concentration determined by a titration metric on at least one titration node day and the titrated or maintenance dose may be sufficient to provide a serum androst-4-en-17β-ol-3-one plasma concentration within the target range.

Surprisingly, the androst-4-en-17β-ol-3-one ester pharmaceutical compositions and oral dosage units comprising (17-ß)-3-oxoandrost-4-en-17-yl tridecanoate having loading in the range of about 14 wt % to about 42 wt % of the present invention may be formulated to administer one or more capsules daily to each subject with one or more dose titrations, if/as needed, until the therapy achieves the therapeutic effectiveness (e.g. ≥75% of subjects when administered to a group of hypogonadal subjects with androst-4-en-17β-ol-3-one $C_{avg}$ within the eugonadal range). In one aspect, the pharmaceutical compositions and oral dosage units of the present invention may be administered for a period of at least 7 days (at the steady state of androst-4-en-17β-ol-3-one) with at least one dose titration, if needed, to arrive at the maintenance dosage based on PK performance (e.g. $C_{avg}$, $C_{max}$, $C_t$, or $C_{min}$) per dose (such as per one morning, evening or afternoon dose). In another aspect, the dose titration, if needed, can be performed at least one of about 7 days, about 9 days, about 11 days, about 13 days, about 15 days, about 21 days, about 28 days, about 1 month, about 2 months, about 3 months, about 4 months, about 5 months, about 6 months, about 1 year, or about 2 years post the start of an androst-4-en-17β-ol-3-one ester therapy.

In one aspect, the pharmaceutical compositions and oral dosage units of the present invention can be administered for a period of at least 7 days (at the steady state of androst-4-en-17β-ol-3-one) with dose titration, if/as needed, dependent upon a titration metric based on $C_t$ post dose (such as one morning, evening or afternoon dose). In one aspect, the titration metric may include a blood sampling performed at one of 3 hrs, 4 hrs, 5 hrs, 6 hrs, 7 hrs, 8 hrs, 10, hrs, 11 hrs, 12 hrs, 13 hrs, 14 hrs, 15 hrs, 16 hrs, 17 hrs, and 18 hrs post dosing. In another aspect, the increase or decrease in dose is based on a titration metric, which comprises titration criteria and $C_t$. For example, the titration metric may direct to increase the dose amount if the $C_t$ level is less than a threshold level between 250 ng/dl and 500 ng/dL used in the titration metric. For another example, the titration metric may direct to decrease the dose amount if the $C_t$ level is greater than a threshold level between 500 ng/dl and 1200 ng/dL used in the titration metric. In one aspect, the increase in the titrated dose from the initial dose or the previously administered dose in a maintenance dosage of androst-4-en-17β-ol-3-one total equivalent amount is at least 50 mg, 60 mg, 75 mg, 97 mg, 107 mg, 119 mg, 149 mg, 179 mg, 198 mg, 208 mg, 223 mg, 238 mg, 268 mg, or 298 mg. In another aspect, the decrease in the titrated dose from the initial dose or the previously administered dose in a maintenance dosage of androst-4-en-17β-ol-3-one equivalent amount is at least 50 mg, 60 mg, 75 mg, 97 mg, 107 mg, 119 mg, 149 mg, 179 mg, 198 mg, 208 mg, 223 mg, 238 mg, 268 mg, or 298 mg. In another aspect, the dose titration can be performed at at least one of 7 days, 9, days, 11 days, 13 days, 15 days, 21 days, 28 days, 1 month, 2 months, 3 months, 4 months, 5 months, 6 months, 1 year, and 2 years post the start of an androst-4-en-17β-ol-3-one therapy.

The androst-4-en-17β-ol-3-one ester pharmaceutical compositions and oral dosage units comprising (17-ß)-3-oxoandrost-4-en-17-yl tridecanoate with loading in the range of about 14 wt % to about 42 wt % in the present invention can be formulated to administer one or more dosage units daily to each subject with one or more dose titrations, if/as needed, until the therapy achieves the desired therapeutic effectiveness (e.g. ≥75% of subjects with $C_{avg}$ within the normal range and <3% of subjects with $C_{max}$ greater than 2.5× the ULN). In one aspect, the pharmaceutical compositions and oral dosage units of the present invention can be administered for a period of at least 7 days (at a steady state of androst-4-en-17β-ol-3-one) for one dose titration, if/as needed, based on PK performance (e.g., $C_{avg}$, $C_{max}$, $C_t$, or $C_{min}$) per dose (such as one morning, evening, or afternoon dose). In another aspect, the dose titration can be performed at at least one of 7 days, 9, days, 11 days, 13 days, 15 days, 21 days, 28 days, 1 month, 2 months, 3 months, 4 months, 5 months, 6 months, 1 year, and 2 years post the start of an androst-4-en-17β-ol-3-one ester therapy.

In one aspect, the pharmaceutical compositions and oral dosage units of the present invention can be administered for a period of at least 7 days (at a steady state of androst-4-en-17β-ol-3-one) with dose titration, if/as needed, dependent upon a titration metric based on Ce per dose (such as one morning, evening or afternoon dose). In one aspect, the titration metric may include blood sampling performed at one of 3 hrs, 4 hrs, 5 hrs, 6 hrs, 7 hrs, 8 hrs, 9 hrs, 10 hrs, 12 hrs, 13 hrs, 14 hrs, 15 hrs, 16 hrs, 17 hrs, and 18 hrs post dose or any time between 3 hrs and 18 hrs post dose. In another aspect, the increase or decrease in dose, if/as needed, is based on a titration metric comprising the titration criteria and $C_t$. For example, the titration metric may direct to increase the dose if the $C_t$ level is less than a threshold level between 250 ng/dl and 500 ng/dL, such as one of <250 ng/dL, <275 ng/dL, <300 ng/dL, <325 ng/dL, <350 ng/dL, <375 ng/dL, <400 ng/dL, <425 ng/dL, <450 ng/dL, <475 ng/dL, or <500 ng/dL. For another example, the titration metric may direct to decrease the dose if the $C_t$ level is greater than a threshold level between 500 ng/dL and 1200 ng/dL, such as one of >500 ng/dL, >550 ng/dL, >600 ng/dL, >650 ng/dL, >700 ng/dL, >750 ng/dL, >800 ng/dL, >850 ng/dL, >900 ng/dL, >950 ng/dL, >1000 ng/dL, >1050 ng/dL, >1080 ng/dL, >1100 ng/dL, >1140 ng/dL, or >1200 ng/dL. In one aspect, the increase in a titrated dose, if/as needed, from the initial dose or the previously administered dose in a maintenance dosage as an androst-4-en-17β-ol-3-one total equivalent amount may be one of 50 mg, 60 mg, 75 mg, 97 mg, 107 mg, 119 mg, 149 mg, 179 mg, 198 mg, 208 mg, 223 mg, 238 mg, 268 mg, or 298 mg. In another aspect, the decrease in a titrated dose, if/as needed, from the initial dose or the previously administered dose in a maintenance dosage as an androst-4-en-17β-ol-3-one total equivalent amount may be one of 50 mg, 60 mg, 75 mg, 97 mg, 107 mg, 119 mg, 149 mg, 179 mg, 198 mg, 208 mg, 223 mg, 238 mg, 268 mg, or 298 mg. In another aspect, the dose titration, if/as needed, may be performed at one of 7 days, 9, days, 11 days, 13 days, 15 days, 21 days, 28 days, 1 month, 2 months, 3 months, 4 months, 5 months, 6 months, 1 year, or 2 years post the start of an androst-4-en-17β-ol-3-one ester therapy.

In another embodiment, after the first dose titration, if/as needed, from the initial dose of an initial dosage of an androst-4-en-17β-ol-3-one ester, the pharmaceutical compositions and oral dosage units of the present invention when administered to a group of hypogonadal subjects, may provide at least 75% of the hypogonadal subjects with a $C_{avg}$ within the normal range if the initial dose of an initial dosage of androst-4-en-17β-ol-3-one total equivalent amount ranges from 149 mg to 893 mg. In the other embodiment, after the second dose titration, if/as needed, from the initial dose of an initial dosage of an androst-4-en-17β-ol-3-one total equivalent amount, the pharmaceutical compositions and oral dosage units of the present invention when administered to a group of hypogonadal subjects, may provide at least 75% of the hypogonadal subjects with an androst-4-en-17β-ol-3-one $C_{avg}$ within the eugonadal range if the initial dose of an initial dosage of an androst-4-en-17β-ol-3-one total equivalent amount ranges from 149 mg to 893 mg. In another embodiment, after the third dose titration, if/as needed, from the initial dose of an initial dosage of an androst-4-en-17β-ol-3-one total equivalent amount, the pharmaceutical compositions and oral dosage units of the present invention when administered to a group of hypogonadal subjects, may provide at least 75% of the hypogonadal subjects with an androst-4-en-17β-ol-3-one $C_{avg}$ within the eugonadal range if the initial dose of an initial dosage of androst-4-en-17β-ol-3-one total equivalent amount ranges from 149 mg to 893 mg.

In yet further embodiment, after titration(s), if/as needed, from the initial dose of an initial dosage of an androst-4-en-17β-ol-3-one ester, the pharmaceutical compositions and oral dosage units of the present invention when administered to a group of hypogonadal subjects, may achieve the $C_{max}$ performance target of an androst-4-en-17β-ol-3-one $C_{max}$ of greater than 2.5×ULN in about 3% or less of the hypogonadal males in the group, if the initial dose of an initial dosage of androst-4-en-17β-ol-3-one total equivalent amount ranges from 149 mg to 893 mg, from 149 mg to 833 mg, from 149 mg to 745 mg, from 149 mg to 655 mg, from 149 mg to 600 mg, from 179 mg to 775 mg, from 250 mg to 895 mg, or from 250 mg to 745 mg.

In yet further embodiment, after titration(s), if/as needed, from the initial dose of an initial dosage of an androst-4-en-17β-ol-3-one ester, the pharmaceutical compositions and oral dosage units of the present invention when administered to a group of hypogonadal subjects, may achieve the $C_{max}$ performance target of an androst-4-en-17β-ol-3-one $C_{max}$ of greater than 2.5×ULN in about 3% or less of the hypogonadal males in the group, if the initial dose of an initial dosage of an androst-4-en-17β-ol-3-one total equivalent amount is greater than or equal to one of about 195 mg, about 200 mg, about 250 mg, about 268 mg, about 300 mg, about 328 mg, about 350 mg, about 400 mg, about 415 mg, about 445 mg, about 475 mg, about 505 mg, about 535 mg, about 565 mg, about 600 mg, about 745 mg, about 775 mg, and about 895 mg. In one aspect, the pharmaceutical compositions and oral dosage units of the present invention when administered to a group of hypogonadal subjects, may achieve the $C_{max}$ performance target of an androst-4-en-17β-ol-3-one $C_{max}$ of greater than 2.5×ULN in about 3% or less, or about 2% or less or about 1% or less of the hypogonadal males in the group, if the initial dose of androst-4-en-17β-ol-3-one total equivalent amount is greater than or equal to one of about 195 mg, about 200 mg, about 250 mg, about 268 mg, about 300 mg, about 328 mg, about 350 mg, about 400 mg, about 415 mg, about 445 mg, about 475 mg, about 505 mg, about 535 mg, about 565 mg, about 600 mg, about 745 mg, about 775 mg, and about 895 mg.

In yet further embodiment, after titration(s), if/as needed, from the initial dose of an initial dosage of androst-4-en-17β-ol-3-one ester, the pharmaceutical compositions and oral dosage units of the present invention when administered to a group of hypogonadal subjects, may achieve the $C_{avg}$ performance target of an androst-4-en-17β-ol-3-one (e.g. at least 75% of the hypogonadal males in the group with $C_{avg}$ within the normal range), if the initial dose of an initial dosage of an androst-4-en-17β-ol-3-one total equivalent amount is greater than or equal to one of about 195 mg, about 200 mg, about 250 mg, about 268 mg, about 300 mg, about 328 mg, about 350 mg, about 400 mg, about 415 mg, about 445 mg, about 475 mg, about 505 mg, about 535 mg, about 565 mg, about 600 mg, about 745 mg, about 775 mg, and about 895 mg. In one aspect, the pharmaceutical compositions and oral dosage units of the pharmaceutical compositions and oral dosage units of the present invention when administered to a group of hypogonadal subjects, may achieve the $C_{avg}$ performance target of an androst-4-en-17β-ol-3-one administration, such as a target of at least 75%, at least 80%, at least 83%, at least 86%, at least 88%, at least 90%, at least 92%, at least 94%, or at least 96% of the hypogonadal males in the group achieving a $C_{avg}$ within the normal range, if the initial dose of an initial dosage of an androst-4-en-17β-ol-3-one total equivalent amount administration is greater than or equal to one of about 195 mg, about 200 mg, about 250 mg, about 268 mg, about 300 mg, about 328 mg, about 350 mg, about 400 mg, about 415 mg, about 445 mg, about 475 mg, about 505 mg, about 535 mg, about 565 mg, about 600 mg, about 745 mg, about 775 mg, and about 895 mg.

DETAILED DESCRIPTION

Figure 1A:
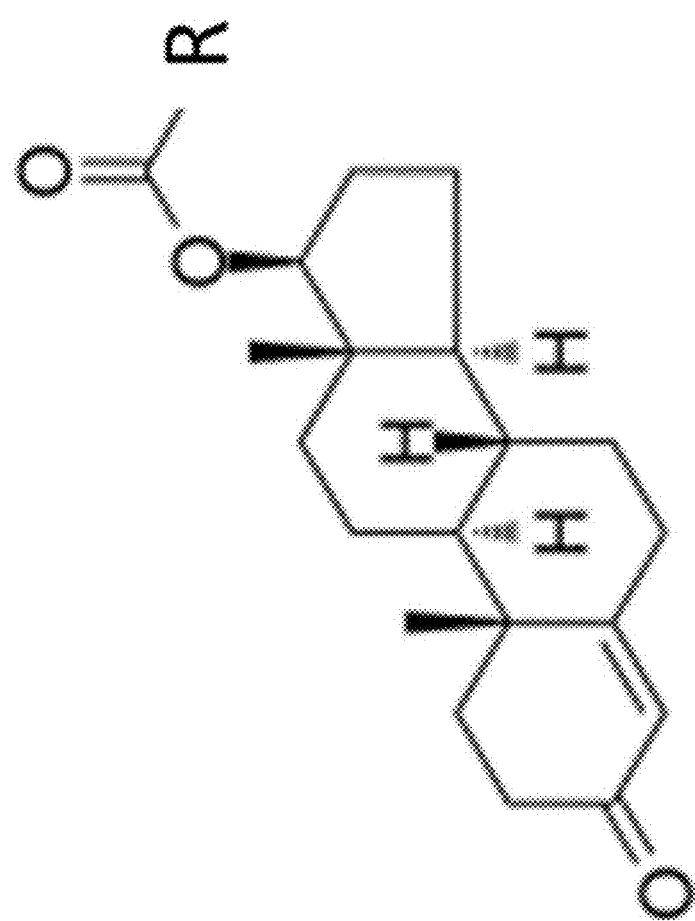
FIG. 1A is an illustration of the chemical structure for the androst-4-en-17β-ol-3-one ester, wherein R is alkyl group and can be C-10, C-11, and C-12 alkyl group in this disclosure.
Figure 1B:
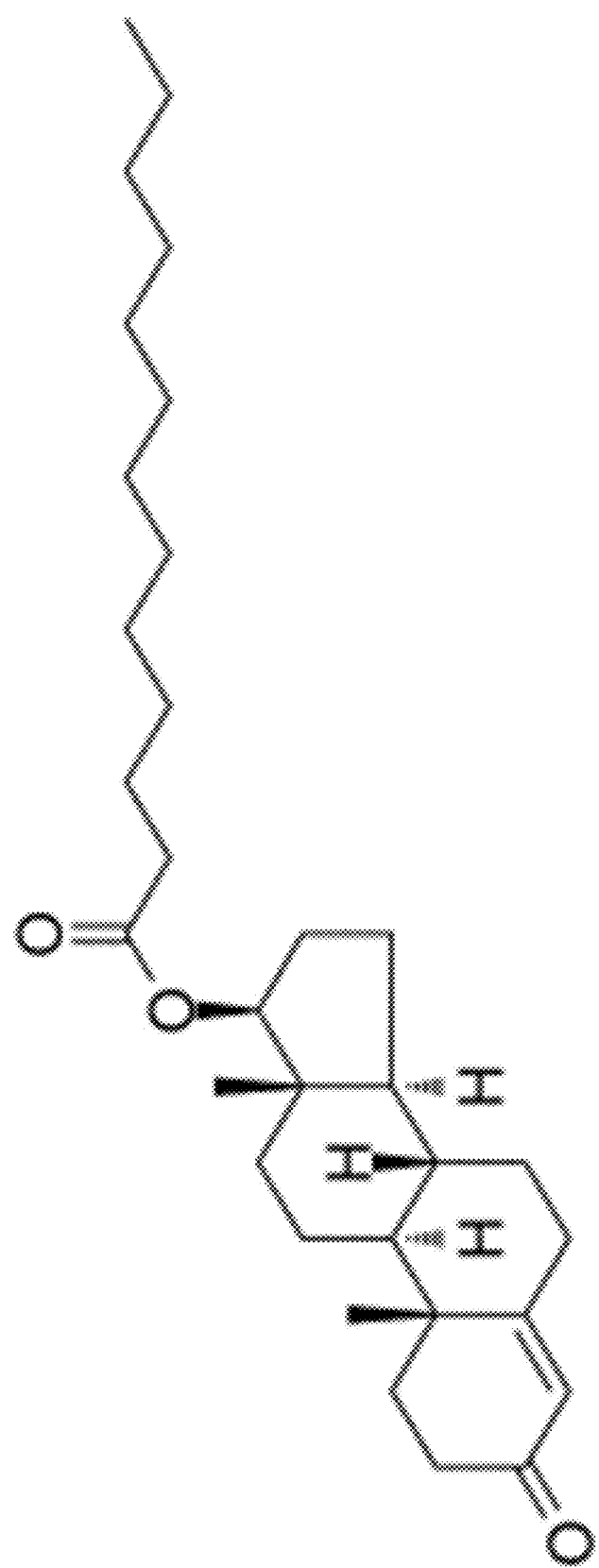
FIG. 1B is an illustration of the chemical structure for (17-ß)-3-oxoandrost-4-en-17-yl tridecanoate.

Before the present androst-4-en-17β-ol-3-one ester compositions with oral dosage units and related methods of use are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an", and "the" include plural referents unless the context clearly dictates otherwise. Thus, for example, reference to "an excipient" includes reference to one or more of such excipients, and reference to "the carrier" includes reference to one or more of such carriers.

Definitions

As used herein, the term "treatment", when used in conjunction with the administration of pharmaceutical compositions and oral dosage units containing androst-4-en-17β-ol-3-one ester, which comprises (17-ß)-3-oxoandrost-4-en-17-yl tridecanoate, refers to the administration of the oral dosage units and pharmaceutically acceptable composition to subjects who are either asymptomatic or symptomatic. In other words, "treatment" can both be to reduce or eliminate symptoms associated with a condition present in a subject, or it can be prophylactic treatment, i.e., to prevent the occurrence (or reoccurrence) of the symptoms in a subject. Such prophylactic treatment can also be referred to as prevention of the condition.

As used herein, the androst-4-en-17β-ol-3-one ester in the composition can be (17-ß)-3-oxoandrost-4-en-17-yl tridecanoate only, a combination of (17-ß)-3-oxoandrost-4-en-17-yl tridecanoate and (17-ß)-3-oxoandrost-4-en-17-yl undecanoate, a combination of (17-ß)-3-oxoandrost-4-en-17-yl tridecanoate and (17-ß)-3-oxoandrost-4-en-17-yl dodecanoate, or a combination of (17-ß)-3-oxoandrost-4-en-17-yl tridecanoate, (17-ß)-3-oxoandrost-4-en-17-yl undecanoate, and (17-ß)-3-oxoandrost-4-en-17-yl dodecanoate.

As used herein, "androst-4-en-17β-ol-3-one equivalent amount" or "total amount of androst-4-en-17β-ol-3-one equivalent" is used interchangeably and refers to the total amount of androst-4-en-17β-ol-3-one in a composition regardless of the (ester) source of the androst-4-en-17β-ol-3-one, and is typically expressed as a percentage of weight of the entire composition. The androst-4-en-17β-ol-3-one equivalent amount of a composition may be calculated by multiply a known androst-4-en-17β-ol-3-one ester amount of a composition by a conversion factor (CF) or functionally equivalently dividing by a conversion ratio (CR) (which is the reciprocal of the CF). If for instance, a composition contains a known amount of a sole androst-4-en-17β-ol-3-one ester of (17-ß)-3-oxoandrost-4-en-17-yl undecanoate, then an androst-4-en-17β-ol-3-one equivalent amount of the composition may be derived by dividing the amount of (17-ß)-3-oxoandrost-4-en-17-yl undecanoate of the composition by a CR of 1.58. Alternatively if for instance, a composition contains a known amount of a sole androst-4-en-17β-ol-3-one ester of (17-ß)-3-oxoandrost-4-en-17-yl dodecanoate, then an androst-4-en-17β-ol-3-one equivalent amount of the composition may be derived by dividing the amount of (17-ß)-3-oxoandrost-4-en-17-yl dodecanoate of the composition by a CR of 1.63. Further alternatively if for instance, a composition contains a known amount of a sole androst-4-en-17β-ol-3-one ester of (17-ß)-3-oxoandrost-4-en-17-yl tridecanoate, then an androst-4-en-17β-ol-3-one equivalent amount of the composition may be derived by dividing the amount of (17-ß)-3-oxoandrost-4-en-17-yl tridecanoate of the composition by a CR of 1.68. Further alternatively, if a composition contains a combination of androst-4-en-17β-ol-3-one esters (e.g. a composite androst-4-en-17β-ol-3-one ester), then the androst-4-en-17β-ol-3-one equivalent amount of a composition may be calculated by separately dividing the various known androst-4-en-17β-ol-3-one ester amounts of the composition by their respective CRs, and then summing the resultant values. Further alternatively, if a composition contains a composite androst-4-en-17β-ol-3-one ester, the androst-4-en-17β-ol-3-one equivalent amount of the composition may be calculated by dividing the known composite androst-4-en-17β-ol-3-one ester amount of the composition by a composite CR, where the composite CR represents a CR value that is weighted in proportion to the respective amount of the various known androst-4-en-17β-ol-3-one ester amounts in the composition. For instance, if a composite androst-4-en-17β-ol-3-one ester consisted of 50% (17-ß)-3-oxoandrost-4-en-17-yl undecanoate (corresponding to a CR of 1.58), 35% (17-ß)-3-oxoandrost-4-en-17-yl dodecanoate (corresponding to a CR of 1.63), and 15% (17-ß)-3-oxoandrost-4-en-17-yl tridecanoate (corresponding to a CR of 1.68), the composite CR would be calculated to be 50%×1.58+35%×1.63+15%×1.68=1.6125. Thus in practice for example, if a composition having a known androst-4-en-17β-ol-3-one ester that consists exclusively of 150 mg of (17-ß)-3-oxoandrost-4-en-17-yl tridecanoate, the total androst-4-en-17β-ol-3-one equivalent amount of the composition may be calculated to be 150 mg÷1.68=89 mg of androst-4-en-17β-ol-3-one. Further in practice for example, if a composition having a known composite androst-4-en-17β-ol-3-one ester that consists exclusively of a combination of 100 mg of (17-ß)-3-oxoandrost-4-en-17-yl undecanoate and 200 mg of (17-ß)-3-oxoandrost-4-en-17-yl tridecanoate, then the total androst-4-en-17β-ol-3-one equivalent amount may be calculated to be (100 mg÷1.58)+(200 mg÷1.68)=182.34 mg of androst-4-en-17β-ol-3-one.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Furthermore, the term "dosage form" can include one or more formulation(s) or composition(s) provided in a format for administration to a subject. When any of the above terms is modified by the term "oral" such terms refer to compositions, formulations, or dosage forms formulated and intended for oral administration to subjects.

As used herein, the term "fatty acid" refers to unionized carboxylic acids with a long aliphatic tail (chain), either saturated or unsaturated, conjugated or non-conjugated.

Unless otherwise specified, the term C8 to C22 fatty acid glycerides refers to a mixture of mono-, di-, and/or triglycerol esters of medium to long chain (C8 to C22) fatty acids.

Further, as used herein, the dispersant of the current invention is at least one selected from the group of hydrophilic surfactant or lipophilic surfactant. In one embodiment, the dispersant includes a hydrophilic surfactant.

As used herein, the term "solidifying agent" or "solidifying additive" are used interchangeably and refer to a pharmaceutically acceptable additive that is in a solid physical state at 20° C. Similarly, a "solid lipophilic additive" refers to a lipophilic compound or component that is in a solid physical state at 20° C. and/or renders the composition or dosage form non-liquid, such as solid or semi-solid.

As used herein, the terms "fully solubilized" and "solubility", when used to describe the state of androst-4-en-17β-ol-3-one ester with respect to a composition and/or capsule fill, refer to the absence of androst-4-en-17β-ol-3-one ester crystals in the composition or oral dosage form when observed under XRD (X-ray Diffraction) spectroscopy showing that the distinct crystalline peaks of androst-4-en-17β-ol-3-one ester are absent in the diffractometry graph.

Similarly, the solubility of androst-4-en-17β-ol-3-one ester in a particular compound, e.g., an additive, is the amount of androst-4-en-17β-ol-3-one ester dissolved to form a visibly clear solution at a specified temperature such as about 25° C. or about 37° C. As used herein, the term "substantially solubilized", when used to describe the state of androst-4-en-17β-ol-3-one ester with respect to a composition and/or capsule fill, refer to something less than the complete absence of androst-4-en-17β-ol-3-one ester crystals in the composition or oral dosage form when the composition or oral dosage form is subjected XRD analysis. Under XRD analysis, the distinct peaks of androst-4-en-17β-ol-3-one ester crystals in the composition or oral dosage form are insufficient so as to enable the distinguishing of crystalline forms from amorphous forms. With this definition in mind, compositions having crystalline forms of androst-4-en-17β-ol-3-one ester at about room temperature would be considered partially solubilized to have an unsolubilized fraction and a solubilized fraction of androst-4-en-17β-ol-3-one ester which fraction includes androst-4-en-17β-ol-3-one ester in a solid state that is not crystalline such as amorphous and solid solution which are solubilized but undissolved.

As used herein, "undissolved" or "non-dissolved" can be used interchangeably and when one is used to describe the state of androst-4-en-17β-ol-3-one ester with respect to a composition and/or capsule fill refers to the androst-4-en-17β-ol-3-one ester in a non-liquid androst-4-en-17β-ol-3-one ester containing composition that is solubilized (such as non-crystalline) and non-solubilized such as crystalline androst-4-en-17β-ol-3-one ester. The solubility of androst-4-en-17β-ol-3-one ester in the composition can be estimated based on the individual solubility in the composition components. For additives that are viscous or non-liquid at room temperature, androst-4-en-17β-ol-3-one ester solubility in the composition at room temperature (RT) may be estimated based on the observed values at higher temperature such as at 37° C., if available/determinable.

As used herein, "dissolved" when used to describe the state of androst-4-en-17β-ol-3-one ester with respect to a composition or capsule fill refers to an androst-4-en-17β-ol-3-one ester containing liquid solution having no undissolved androst-4-en-17β-ol-3-one ester.

As used herein, the term "lipophilic," refers to compounds that are not freely soluble in water; and the term "lipophilic surfactant" refers to surfactants that have HLB (hydrophilic-lipophilic balance) values of about 10 or less. Conversely, the term "hydrophilic" refers to compounds that are soluble in water; and term "hydrophilic surfactant" refers to surfactants that have HLB values of more than about 10.

As used herein, the term "ionizable fatty acid" refers to a fatty acid compound that changes its HLB as a function of pH. For example oleic acid is predominantly lipophilic at lower pH values (such as those found in the stomach) but becomes a predominantly hydrophilic at higher pH values (such as those found in the intestine).

As used herein, "subject" refers to a mammal that may benefit from the administration of a drug composition or method of this invention. Examples of subjects include humans. In one aspect, the subject can be a normal human male considered healthy. In another embodiment, the subject can be a hypogonadal male. As used herein, the androst-4-en-17β-ol-3-one deficiency or hypogonadism in a male human subject (hypogonadal male) refers to a condition wherein the average baseline plasma androst-4-en-17β-ol-3-one concentration ($C_{avg}$–B) is about 300 ng/dL or less. However in some instances, androst-4-en-17β-ol-3-one deficiency or hypogonadism in a male human subject refers to a condition wherein the average baseline plasma androst-4-en-17β-ol-3-one concentration is about 400 ng/dL or less.

As used herein, a "responder" is a subject who responds to an exogenous oral androst-4-en-17β-ol-3-one ester therapy. "Responder analysis" is the assessment of the effectiveness of androst-4-en-17β-ol-3-one ester therapy in a group of subjects deemed to obtain benefits of oral androst-4-en-17β-ol-3-one ester therapy. For example, a "$C_{avg}$ responder" is considered to be a subject who achieves an androst-4-en-17β-ol-3-one $C_{avg}$ at a steady state post dose administration (when titration is complete) within the normal androst-4-en-17β-ol-3-one level range. In another example, "$C_{avg}$ responder rate" is the percent of subjects in a group previously in need of androst-4-en-17β-ol-3-one therapy who achieve a Cavg within the normal an androst-4-en-17β-ol-3-one level range when titration is complete.

As used herein, "group" or "group of subjects" refers to a collection of at least 24 human male subjects who receive and respond to exogenous oral administration of the compositions disclosed herein, namely androst-4-en-17β-ol-3-one ester containing compositions. In one aspect, the group can include at least 100 or at least 300 male subjects. In another aspect, the group can include at least 1000 male subjects. In another embodiment, the subjects can be hypogonadal subjects.

The term "oral administration" represents any method of administration in which an active agent can be administered by swallowing, chewing, or sucking of the dosage form.

The composition of the current inventions can be admixed with food or drink prior to being orally consumed.

As used herein, "regimen" refers to an administration scheme comprising at least one dosage. As used herein, "dosage" refers to the prescribed administration of a specific amount, number, and frequency of doses over a specific period of time (see the entry for "Difference Between Drug Dose and Dosage" on the website of verywellhealth.com). As used herein, "dose" refers to a single instance of a quantity of a composition (e.g., medicine or drug) taken or recommended to be taken at a particular time. For example, a regimen having an initial dosage for a hypogonadal male subject may provide for a total dose of 800 mg administered within 30 min post meal (e.g., breakfast) having about 15-55 g of fat content repeated daily.

As used herein, "titration dosage regimen" refers to a regimen wherein at least one initial dose of an initial dosage is administered to a subject, an assessment of the efficacy of the administered at least one initial dose of an initial dosage is performed, and then at least one titrated or maintained dose in an maintenance dosage is administered to the subject, wherein based on the efficacy assessment an amount of at least one titrated or maintained dose of a maintenance dosage is either increased, decreased, or unchanged. Typically in a titration dosage regimen, if a serum concentration level relating to the administered dose exceeds a predetermined level, the quantity of at least one maintained dose is decreased, and wherein if a serum concentration level relating to the administered dose subceeds predetermined level, the quantity of the at least one maintained dose is increased, and wherein if a serum concentration level relating to the administered dose is within a predetermined range, the quantity of the at least one maintained dose is unchanged relative to an immediately preceding administered dose of an initial or maintenance dosage. It is noted that the number of doses administered prior to the maintained dose, the number of efficacy assessments, and the number of subsequent doses all may vary depending upon the response rate and needs of a given subject. As used herein, "titration amount" refers to the amount by which a dose is increased or decreased (i.e., the delta amount).

As used herein, a dose refers to a specified amount of medication taken at one time. By contrast, the dosage is the prescribed administration of a specific amount, number, and frequency of doses over a specific period of time. Also, as used herein, "daily dose" refers to the amount of active agent (e.g., androst-4-en-17β-ol-3-one ester) administered to a subject over a 24 hour period of time. The daily dose in a dosage can be administered via one or more administrations during the 24 hour period. In one embodiment, the daily dose provides for one administration in a 24 hour period. With this in mind, a "dose of an initial (or starting) dosage" refers to a dose administered during the initial dosage of a regimen. An initial (or starting) dose can be the very first dose during the initial dosage. Similarly, a "a titrated dose" refers to a dose administered as part of an up-titrated or down-titrated dosage of a regimen. In some subjects, the initial dosage may be the same as an untitrated maintenance dosage. "Titrated dose (or dosage)" can be interchangeably used with "increased dose (or dosage)" or "decreased dose (or dosage)" in a maintenance dosage. The titration, if/as needed, may be for instance an up-titration or a down-titration dose that is increased or decreased by about 20%, about 25%, about 30%, about 33%, about 35%, about 37%, about 40%, about 45%, about 50%, about 55%, about 60%, about 67%, about 75%, about 80%, or about 90% of the immediately preceding dose. A maintenance dose is a dose administered after at least one dose titration. It is worth noting that the titrated dose follows a dose titration based on the androst-4-en-17β-ol-3-one titration metric on a titration node day, however the titrated dose does not necessarily need to be of a different quantity from the initial (or starting) dose or the immediately previously administered dose (in the case of multiple titrations).

As used herein, "non-liquid" when used to refer to the state of a composition disclosed herein refers to the physical state of the active agent as being a semi-solid or solid at room temperature (approximately 20° C.).

As used herein, "solid" and "semi-solid" refers to the physical state of the active agent that supports its own weight at standard temperature and pressure and has adequate viscosity or structure to not freely flow. Semi-solid materials may conform to the shape of a container under applied pressure.

As used herein, "titration" or "dose titration" or "dose adjustment" are used interchangeably and refer to an increase or decrease, if/as needed, of the total dose of androst-4-en-17β-ol-3-one ester administered to a subject, typically based on the response of the subject to the exogenously administered androst-4-en-17β-ol-3-one ester. The dose can be increased or decreased, if/as needed, based on the measurement of serum androst-4-en-17β-ol-3-one concentration after a steady state has been achieved. The dose can be increased or decreased, if/as needed, based on the measurement of serum androst-4-en-17β-ol-3-one concentration $C_t$ range against a criteria of lower or higher than a predetermined $C_t$ level after a steady state has been achieved.

As used herein, "steady state" refers to a state of stable response in serum total androst-4-en-17β-ol-3-one levels to exogenously administered androst-4-en-17β-ol-3-one ester, typically achieved after at least 7 days following the start of a dosing regimen.

In some embodiments, the titration can also include the adjustment of the way the total daily dose is administered such as whether it is administered as one, two, or three doses within a 24 hour period, whether it is administered with a meal, with a meal with a particular fat content, or at a particular hour of the day.

As used herein, "initial dose" unless otherwise qualified refers to the first dose of androst-4-en-17β-ol-3-one ester administered to a subject in need of androst-4-en-17β-ol-3-one therapy. Thus unless otherwise qualified, the "initial dose" inherently refers to the first dose of a first dosage of a regimen. It is noted that as distinct from an unqualified "initial dose", where specifically indicted, there may also be an initial dose of a subsequent dosage. As used herein, "titrated dose" or "titration dose" refers to the first dose of androst-4-en-17β-ol-3-one ester administered to a subject in need of androst-4-en-17β-ol-3-one therapy after an androst-4-en-17β-ol-3-one level of the subject is measured, wherein the instant dose is adjusted (up or down) or unadjusted relative to the immediately preceding dose based on the measured androst-4-en-17β-ol-3-one level. The amount of adjustment if any is preferably determined based on a titration metric using an androst-4-en-17β-ol-3-one concentration measurement on the titration node day. Both a regimen and a dosage may include a plurality of titrated doses. As used herein, "maintenance dose" or "maintained dose" refers to a dose of androst-4-en-17β-ol-3-one ester administered to a subject in need of androst-4-en-17β-ol-3-one therapy wherein an androst-4-en-17β-ol-3-one level of the subject is not measured between administration of the instant dose and an immediately preceding dose, and wherein the instant dose quantity is not adjusted relative to the immediately preceding dose. Both a regimen and a dosage may include a plurality of maintenance doses.

As used herein, "titration node" or "titration node day" are used interchangeably and refer to a day on which a blood sample is drawn from a subject for measurement of the androst-4-en-17β-ol-3-one concentrations in order to determine whether an androst-4-en-17β-ol-3-one ester dose titration is necessary and what the titration type might need to be. The measured androst-4-en-17β-ol-3-one levels may also be used to determine the dose titration based on a titration metric to be utilized in deciding dose titration needs for an individual subject. As dosing regimens can include one or more titration node days the term may refer to a first titration node during a dosing regimen (e.g., between the initial dose and the titrated dose) or it can refer to a subsequent titration node day between a titrated dose and a subsequently titrated dose.

As used herein, "titration day" refers to the day when administration of a newly titrated (adjusted) dose is initiated. It should be noted that one or more titrations can be conducted to arrive at a titrated dose for therapeutically effectiveness in terms of achievement of PK performance targets. Thus, the titrated dose can be considered to be the dose based on the last or most recent titration.

As used herein, "titration metric" is a pharmacokinetic (PK) parameter determined from a blood sample or multiple blood samples on a titration node day. The androst-4-en-17β-ol-3-one PK parameter used as the titration metric can include the $C_{max}$, $C_{avg}$, $C_{min}$, $C_{pre-dose}$ or $C_t$ (total androst-4-en-17β-ol-3-one concentration at a particular time of day). The titration metric can be used to aid along with predetermined threshold criteria in the determination of whether a dose titration is necessary, its magnitude, and other factors possibly included in the titration adjustment.

As used herein, the terms "release" and "release rate" are used interchangeably to refer to the discharge or liberation of a substance, including without limitation a drug, from the dosage form into a surrounding environment such as an aqueous medium either in vitro or in vivo.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

The terms "plasma androst-4-en-17β-ol-3-one concentration", "androst-4-en-17β-ol-3-one concentration in the blood", "total androst-4-en-17β-ol-3-one concentration", "androst-4-en-17β-ol-3-one concentration", "androst-4-en-17β-ol-3-one level", and "serum Androst-4-en-17β-ol-3-one concentration" are used interchangeably and refer to the "total" androst-4-en-17β-ol-3-one concentration which is the sum of the bioavailable androst-4-en-17β-ol-3-one including free and protein-bound androst-4-en-17β-ol-3-one concentrations. As with any bio-analytical measure, for increased consistency the method employed to measure initial serum androst-4-en-17β-ol-3-one levels should be consistent with the method used to monitor and re-measure serum androst-4-en-17β-ol-3-one levels during clinical testing and androst-4-en-17β-ol-3-one therapy for a subject. Unless otherwise stated, "androst-4-en-17β-ol-3-one concentration" refers to serum total androst-4-en-17β-ol-3-one concentration (level).

As used herein, the average total androst-4-en-17β-ol-3-one concentration can be determined using methods and practices known in the art. For example, the average baseline blood androst-4-en-17β-ol-3-one concentration of a human male is the arithmetic mean of the total blood (serum or plasma) androst-4-en-17β-ol-3-one concentrations determined on at least two consecutive time points that are reasonably spaced from each other, for example from about 1 hour to about 168 hours apart. In a particular case, the blood androst-4-en-17β-ol-3-one concentration can be determined on at least two consecutive times that are about 24 hours to about 48 hours apart. In another particular method, the blood androst-4-en-17β-ol-3-one concentration of the human male can be determined at a time between about 5 o'clock and about 11 o'clock in the morning. Further, the blood androst-4-en-17β-ol-3-one concentration can be the determined by standard analytical procedures and methods available in the art, such as for example, automated or manual immunoassay methods, liquid chromatography or liquid chromatography—tandem mass spectrometry (LC-MS/MS) etc.

As used herein, the term $AUC_{0-t}$ is the area under the curve of a plasma-versus-time graph determined for the analyte from the time 0 to time "t".

As used herein, the term "$C_{max}$" refers to a maximum serum concentration level post single dose administration or maximum serum concentration during a 24 hr period post total daily dose administration, "$C_{min}$" refers to a minimum serum concentration level post single dose administration, and "$C_{pre-dose}$" refers to a nominal steady state serum concentration level prior to any dose administration. As used herein, the term "$C_{avg}$", "$C_{ave}$", or "$C_{average}$" are used interchangeably and is determined as the AUC divided by the time period (t). For example, $C_{avg-8h}$ is the average plasma concentration over a period of 8 hours post-dosing determined by dividing the $AUC_{0-8}$ value by 8. Similarly, $C_{avg-12h}$ is the average plasma concentration over a period of 12 hours post-dosing determined by dividing the $AUC_{0-12}$ value by 12; $C_{avg-24h}$ is the average plasma concentration over a period of 24 hours post-dosing determined by dividing the $AUC_{0-24}$ value by 24, and so on. Unless otherwise stated, all $C_{avg}$ values are considered to be $C_{avg-24h}$.

As used herein, "$C_t$" refers to the serum concentration of androst-4-en-17β-ol-3-one at time "t" after administration of a single dose of the drug. The time "t" is generally in hours, unless otherwise specified. For example, a $C_t$ of "$C_{(-2\ to\ 0)}$" refers to serum androst-4-en-17β-ol-3-one concentration measured in a sample collected between the time of about 2 hours before and just immediately prior to dosage administration to a subject. Similarly, $C_t$ of "$C_{(2\ to\ 4)}$" refers to serum androst-4-en-17β-ol-3-one concentration measured in a sample collected between the time of about 2 hours and 4 hours after administration of a dosage to a subject. For another instance, "CU" refers to serum androst-4-en-17β-ol-3-one concentration measured in a sample collected at about 5 hours after administration of a dose to a subject.

As used herein, the term "substantially crystalline" refers to a crystalline containing composition having crystalline forms that have a mean particle size of >1 micron. As used herein, the term "noncrystalline" or "substantially noncrystalline" refers to a composition that is fully or partially solubilized or is in an amorphous solid state without substantial crystalline forms having mean particle size of >1 micron. As used herein, the term "micronized" or "substantially micronized" refers to a particle containing composition having a mean particle size of <20 microns.

As used herein, "free of" or "substantially free of" of a particular compound or compositions refers to the absence of any separately added portion of the referenced compound or composition. Free of or substantially free of can include the presence of 1 wt % or less (based on total composition weight) of the referenced compound which may be present as a component or impurity of one or more of the ingredients.

As used herein, the term "about" is used to provide flexibility to a numerical range endpoint by providing that a given value may be "a little above" or "a little below" the endpoint. As used herein, a plurality of items, structural elements, compositional elements, and/or materials may be presented in a common list for convenience. However, these lists should be construed as though each member of the list is individually identified as a separate and unique member. Thus, no individual member of such list should be construed as a defacto equivalent of any other member of the same list solely based on their presentation in a common group without indications to the contrary.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a defacto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range, or the characteristics being described.

Invention

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

In one embodiment, a pharmaceutical capsule for oral delivery is provided. The capsule includes a capsule shell and a capsule fill. The capsule fill can include an additive and about 14 wt % to about 42 wt % of an androst-4-en-17β-ol-3-one ester based on the total weight of capsule fill. In an aspect, the androst-4-en-17β-ol-3-one ester comprises one of (17-ß)-3-oxoandrost-4-en-17-yl tridecanoate only, a combination of (17-ß)-3-oxoandrost-4-en-17-yl tridecanoate and (17-ß)-3-oxoandrost-4-en-17-yl undecanoate, a combination of (17-ß)-3-oxoandrost-4-en-17-yl tridecanoate and (17-ß)-3-oxoandrost-4-en-17-yl dodecanoate, and a combination of (17-ß)-3-oxoandrost-4-en-17-yl tridecanoate, (17-ß)-3-oxoandrost-4-en-17-yl undecanoate and (17-ß)-3-oxoandrost-4-en-17-yl dodecanoate. The oral dosage capsule is such that when a single oral administration of one or more capsules with an androst-4-en-17β-ol-3-one total equivalent dose amount of about 149 mg to about 893 mg is provided to a male subject.

The compositions and oral dosage units of the present invention can be used to treat subjects, particularly human males, or even more particularly males who suffer from androst-4-en-17β-ol-3-one deficiency or hypogonadism. Accordingly, in one embodiment of the present invention, a method for providing a blood concentration of androst-4-en-17β-ol-3-one within a target serum androst-4-en-17β-ol-3-one concentration $C_{avg}$ range for a male subject is provided. The method includes the step of orally administering to the male subject a dose of an androst-4-en-17β-ol-3-one ester containing composition. The androst-4-en-17β-ol-3-one ester comprises about 14 wt % to about 42 wt % of the androst-4-en-17β-ol-3-one ester containing composition and the dose provides about 150 mg to about 800 mg of androst-4-en-17β-ol-3-one total equivalent amount to the male subject.

In one specific embodiment, at least 25 w/w % of the androst-4-en-17β-ol-3-one ester in the pharmaceutical compositions and oral dosage units comprises (17-ß)-3-oxoandrost-4-en-17-yl tridecanoate. In such embodiment any one of the initial dose, or the titrated dose, or the maintained dose may comprise any amount of (17-ß)-3-oxoandrost-4-en-17-yl tridecanoate between 62 mg to 1500 mg.

In one aspect, the androst-4-en-17β-ol-3-one ester in the pharmaceutical compositions and oral dosage units comprises (17-ß)-3-oxoandrost-4-en-17-yl tridecanoate in an amount of at least one of 25 w/w %, 30 w/w %, 40 w/w %, 50 w/w %, 60 w/w %, 70 w/w %, 80 w/w %, 90 w/w %, and 100 w/w %.

Androst-4-en-17β-ol-3-one deficiency is typically associated with a particular condition that is the source or causes the deficiency. The compositions and oral dosage units of the present invention can be used to treat any condition associated with androst-4-en-17β-ol-3-one deficiency, including complete absence of endogenous androst-4-en-17β-ol-3-one. Examples of conditions associated with androst-4-en-17β-ol-3-one deficiency that can be treated using the oral dosage units and/or compositions of the present invention include, but are not limited to congenital or acquired primary hypogonadism, hypogonadotropic hypogonadism, cryptorchidism, bilateral torsion, orchitis, vanishing testis syndrome, orchidectomy, Klinefelter's syndrome, post castration, eunuchoidism, hypopituitarism, endocrine impotence, infertility due to spermatogenic disorders, impotence, male sexual dysfunction (MSD) including conditions such as premature ejaculation, erectile dysfunction, decreased libido, and the like, micropenis and constitutional delay, penile enlargement, appetite stimulation, androst-4-en-17β-ol-3-one deficiency associated with chemotherapy, androst-4-en-17β-ol-3-one deficiency associated with toxic damage from alcohol, androst-4-en-17β-ol-3-one deficiency associated with toxic damage from heavy metal, osteoporosis associated with androgen deficiency, and combinations thereof.

Other conditions that can be treated by the compositions and oral dosage forms disclosed herein include idiopathic gonadotropin, LHRH deficiency, or pituitary hypothalamic injury from tumors, trauma, or radiation. Typically, these subjects have low serum androst-4-en-17β-ol-3-one levels but have gonadotropins in the normal or low range. In one embodiment, the compositions or oral dosage forms may be used to stimulate puberty in carefully selected males with clearly delayed puberty not secondary to pathological disorder. In another embodiment, the compositions and oral dosage forms may be used in female-to-male transsexuals in order to maintain or restore male physical and sexual characteristics including body muscle mass, muscle tone, bone density, body mass index (BMI), enhanced energy, motivation and endurance, restoring psychosexual activity etc. In some embodiments, the (17-ß)-3-oxoandrost-4-en-17-yl tridecanoate containing compositions and oral dosage units may be useful in providing hormonal male contraception.

Additionally, androst-4-en-17β-ol-3-one therapy can also be used to improve the quality of life of subjects suffering from conditions such as decreased libido, diminishing memory, anemia due to marrow failure, renal failure, chronic respiratory or cardiac failure, steroid-dependent autoimmune disease, muscle wasting associated with various diseases such as AIDS, preventing attacks of hereditary angioedema or urticaria; andropause, and palliating terminal breast cancer. In some situations, certain biomarkers such as for example, increased SHBG levels, can be used to diagnose a subject who may be in need of androst-4-en-17β-ol-3-one therapy. These biomarkers can be associated with conditions/disease states such as anorexia nervosa, hyperthyroidism, hypogonadism, androgen insensitivity/deficiency, alcoholic hepatic cirrhosis, primary biliary cirrhosis, and the like.

Subjects that can be treated by the (17-ß)-3-oxoandrost-4-en-17-yl tridecanoate containing compositions and oral dosage units of the present disclosure can be any human male in need thereof. In particular, in one embodiment, the human male may be at least 14 years of age. In another embodiment, the human male is an adult of at least age 30. In a further embodiment, the subject can be an adult male of at least age 50. In yet a further embodiment, the subject can be an adult male of at least age 60.

As discussed above, the compositions and oral dosage units disclosed herein can be used to treat androst-4-en-17β-ol-3-one deficiency in human males. In one embodiment, the male human being treated can have an average baseline plasma androst-4-en-17β-ol-3-one concentration of about 400 ng/dL or less. In another embodiment, the male human being treated can have an average baseline plasma androst-4-en-17β-ol-3-one concentration of about 350 ng/dL or less. In another embodiment, the male human being treated can have an average baseline plasma androst-4-en-17β-ol-3-one concentration of about 300 ng/dL or less. In another embodiment, the male human being treated can have an average baseline plasma androst-4-en-17β-ol-3-one concentration of about 250 ng/dL or less. In still another embodiment, the male human being treated can have an average baseline plasma androst-4-en-17β-ol-3-one concentration of about of about 200 ng/dL or less. In a further embodiment, the male human being treated can have an average baseline plasma androst-4-en-17β-ol-3-one concentration of about of about 190 ng/dL or less. In still a further embodiment, the human male has an average baseline plasma androst-4-en-17β-ol-3-one concentration of about 400 ng/dL or less, along with a co-morbid condition of at least one of insulin resistance, fatty liver, hypertension, obesity, sarcopenia, frailty, dyslipidemia or combination thereof.

The androst-4-en-17β-ol-3-one ester compositions and oral dosage units of the current invention can be administered orally to a human male who has an average body mass index (BMI) of about 28 kg/m$^2$ or more. In another embodiment, the human male has an average BMI of about 30 kg/m$^2$ or more. In another embodiment, the human male has an average BMI of about 37 kg/m$^2$ or more. In a further embodiment, the subject male being treated can have a serum sex hormone binding globulin (SHBG) levels of about 40 nmol/L or more. In yet another embodiment, the male human being treated can have a serum SHBG levels of about 60 nmol/L or more.

Further, it has been discovered that the pharmaceutical compositions and oral dosage units disclosed herein can provide therapeutically effective treatment without the need to include oils, triglycerides, and/or hydrophilic surfactants. Accordingly, in one embodiment, the pharmaceutical compositions and oral dosage units can be free of oil. In another embodiment, the pharmaceutical composition and oral dosage units can be free of triglycerides. In one embodiment, the composition or capsule fill can comprise 25 wt % or less of total triglycerides. In one embodiment, the composition or capsule fill can be free of ionizable fatty acids. In another embodiment, the composition or capsule fill can be free of oleic acid. Without wishing to be bound by theory, it is believed that androst-4-en-17β-ol-3-one ester containing compositions or capsule fill that comprise greater than 25 wt % triglycerides have a higher dependence on digestion upon oral administration than do those in which the triglycerides comprise 25 wt % or less of the total composition or capsule fill. In one embodiment, the capsule fill can comprise 15 wt % or less of triglycerides. In yet another embodiment, the capsule fill can comprise 10 wt % or less of triglycerides. In yet a further embodiment, the capsule fill can comprise 5 wt % or less of triglycerides.

In yet a further embodiment, the pharmaceutical compositions and oral dosage units can be free of hydrophilic surfactants. In yet a further embodiment, the composition can include a hydrophilic surfactant as a dispersant and the hydrophilic surfactant can be present in an amount such that it does not appreciably solubilize the androst-4-en-17β-ol-3-one ester in the composition. A hydrophilic surfactant is said to "not appreciably solubilize" androst-4-en-17β-ol-3-one ester when it solubilizes 5 wt % or less of the androst-4-en-17β-ol-3-one ester in the composition or the dosage form. In one embodiment, a hydrophilic surfactant is deemed to "not appreciably solubilize" androst-4-en-17β-ol-3-one ester when it solubilizes 2 wt % or less of the androst-4-en-17β-ol-3-one ester in the composition or oral dosage capsule. In all of these embodiments, the pharmaceutical compositions and oral dosage units can still be capable of providing the necessary dispersion and pharmacokinetics parameters to effectively treat androst-4-en-17β-ol-3-one deficiency.

The androst-4-en-17β-ol-3-one ester can be present in the pharmaceutical compositions and oral dosage units in amounts sufficient to comprise 14 wt % to about 42 wt % of the composition or capsule fill. In one embodiment, the androst-4-en-17β-ol-3-one ester can make up about 15 wt % to about 30 wt % of the composition or oral dosage capsule fill. In yet a further embodiment, the androst-4-en-17β-ol-3-one ester can comprise about 20 wt % to about 30 wt % of the composition or oral dosage capsule fill. In still a further embodiment, the compositions and/or capsule fill material can be such that the androst-4-en-17β-ol-3-one ester comprises about 25 wt % to about 30 wt % of the total composition or capsule fill. In one embodiment, at least 22 wt % of the androst-4-en-17β-ol-3-one ester in the composition or capsule fill can be in a fully solubilized form. In one embodiment, at least 28 wt % of the androst-4-en-17β-ol-3-one ester in the composition or capsule fill can be in a fully solubilized form. In one embodiment, at least 30 wt % of the androst-4-en-17β-ol-3-one ester in the composition or capsule fill can be in a partially solubilized form. In yet another embodiment, at least about 50% of the androst-4-en-17β-ol-3-one ester can be present in dissolved form in the capsule fill or composition. In another embodiment, at least about 5 wt % of the androst-4-en-17β-ol-3-one ester in the capsule fill or composition can be present in undissolved form.

The oral dosage units of the present application may include a dose of a total equivalent amount of an androst-4-en-17β-ol-3-one ester of at least 50 mg. The oral dosage units of the present application may include a dose of a total equivalent amount of an androst-4-en-17β-ol-3-one ester of about 100 mg to about 300 mg. In another embodiment, the oral dosage capsule may include about 100 mg to about 250 mg of a total equivalent amount of an androst-4-en-17β-ol-3-one ester. In another embodiment, the oral dosage capsule may include about 120 mg to about 250 mg of a total equivalent amount of an androst-4-en-17β-ol-3-one ester. In yet a further embodiment, the oral dosage capsule can include about 50 mg to about 250 mg of a total equivalent amount of an androst-4-en-17β-ol-3-one ester. With this in mind, the compositions and oral dosage capsule may be used as part of dosing regimens to provide doses of about 150 mg to about 895 mg of per day of a total equivalent amount of an androst-4-en-17β-ol-3-one ester, and more preferably, a dose of about 250 mg to about 745 mg per day of a total equivalent amount of an androst-4-en-17β-ol-3-one ester. In some aspects, the dose of androst-4-en-17β-ol-3-one total equivalent amount is greater than or equal to one of 149 mg, 179 mg, 198 mg, 250 mg, 268 mg, 298 mg, 327 mg, 357 mg, 397 mg, 417 mg, 417 mg, 446 mg, 476 mg, 506 mg, 536 mg, 595 mg, 595 mg, 744 mg, 774 mg, and 893 mg.

In one embodiment, the androst-4-en-17β-ol-3-one ester in the pharmaceutical compositions and oral dosage units comprises at least 25 w/w % of (17-β)-3-oxoandrost-4-en-17-yl tridecanoate. In one aspect, the androst-4-en-17β-ol-3-one ester in the pharmaceutical compositions and oral dosage units comprises one of at least 25 w/w %, 30 w/w %, 40 w/w %, 50 w/w %, 60 w/w %, 70 w/w %, 80 w/w %, 90 w/w %, and 100 w/w % of (17-β)-3-oxoandrost-4-en-17-yl tridecanoate.

In one embodiment, the amount of androst-4-en-17β-ol-3-one ester per unit dosage form in the pharmaceutical compositions and oral dosage units may comprise at least 62 mg of (17-β)-3-oxoandrost-4-en-17-yl tridecanoate. In an embodiment where the androst-4-en-17β-ol-3-one ester of the pharmaceutical compositions and oral dosage units comprises a combination of (17-β)-3-oxoandrost-4-en-17-yl tridecanoate and at least one of (17-β)-3-oxoandrost-4-en-17-yl undecanoate and (17-β)-3-oxoandrost-4-en-17-yl dodecanoate, the amount of androst-4-en-17β-ol-3-one ester per unit dosage form may comprise an amount between about 100 mg to about 420 mg, such about 100 mg, about 133 mg, about 150 mg, about 168 mg, about 188 mg, about 210 mg, about 225 mg, about 252 mg, about 263 mg, about 298 mg, about 333 mg, about 350 mg, about 375 mg, and about 420 mg.

The additives used in the pharmaceutical compositions and oral dosage units of the present invention play a role in the ability of the formulation to provide the desired therapeutic characteristics. Additives that can be used may be selected from a variety of compounds and mixtures of compounds that have the ability to facilitate loading of androst-4-en-17β-ol-3-one ester. The additive can comprise about 50 wt % to about 86 wt % of the composition or capsule fill. In one embodiment, the additive can comprise about 55 wt % to about 82 wt % of the pharmaceutical composition or oral dosage capsule. In another embodiment, the additive can comprise about 60 wt % to about 80 wt % of the pharmaceutical composition or oral dosage capsule. In one embodiment, the additive can be such that the androst-4-en-17β-ol-3-one ester can have solubility in the additive, at about 37° C., of about 50 mg/g to about 750 mg/g additive.

Non-limiting examples of additives that can be used include C8 to C22 fatty acid glycerides, omega fatty acids, and mixtures thereof. In one embodiment, the C8 to C22 fatty acid glycerides can include C8 to C22 medium and/or long chain monoglycerides, medium and/or long chain diglycerides, or mixtures of a mixture of medium and/or long chain monoglycerides and medium and/or long chain diglycerides. In another embodiment, the additive can consist essentially of medium and/or long chain monoglycerides and/or diglycerides. Medium to long chain monoglycerides and diglycerides refers to compounds having chain lengths of C8 to C22. In one embodiment, the mixture of monoglycerides and diglycerides can have chain lengths of C8 to about C13. In another embodiment, the mixture of monoglycerides and diglycerides can have chain lengths of about C14 to about C22. When the additive includes C8 to C22 fatty acid glycerides, monoglycerides can comprise at least about 40 wt % of the C8 to C22 fatty acid glycerides (such as commercially available MAISINE 42-1, CAPMUL MCM, PECEOL and the like). In another embodiment, the monoglycerides can comprise at least about 60 wt % of the C8 to C22 fatty acid glycerides. In yet a further embodiment, the monoglycerides can comprise at least about 80 wt % of the C8 to C22 fatty acid glycerides.

Non-limiting examples of C8 to C22 fatty acid glycerides that can be used as additive in pharmaceutical compositions and oral dosage units of the present invention include monoglycerides and/or diglycerides derived from sources such as maize oil, poppy seed oil, safflower oil, sunflower oil, borage seed oil, coconut oil, palm kernel oil, castor oil, and mixtures thereof. Although not essential, the additive can also include a triglyceride. The triglyceride can be a medium and/or long chain triglyceride, or mixture thereof, and can be present alone or with other additives. The triglycerides can be selected from a variety of well-known pharmaceutically acceptable triglycerides including, but not limited to vegetable oils such as peanut oil, safflower oil, sunflower oil, olive oil, castor oil, corn oil, maize oil, flax seed oil, wheat-germ oil and the like, or their hydrogenated derivatives and their mixtures thereof. Additional triglyceride sources can include animal derived oils such as fish oil, seal oil, whale oil, and the like, triglycerides of C8-C22 fatty acids or their mixtures; triglycerides of C8-C13 fatty acids; triglycerides of C14-C22 fatty acids. In one embodiment, the composition can include a fatty acid triglyceride and the androst-4-en-17β-ol-3-one ester can comprise at least about 25 wt % of the composition. In another embodiment, the triglyceride can be castor oil. In yet a further embodiment, the castor oil can comprise about 45 wt % or less of the total composition. In yet another embodiment, the castor oil can comprise about 40 wt % or less of the additive. In a further embodiment, the composition can be free of castor oil. In one embodiment of the invention, the additive can include a glyceryl palmitostearate, a glyceryl stearate, a glyceryl distearate, glyceryl monostearate, or a combination thereof.

In another aspect of the invention, the additive can include a C8 to C22 fatty acid glycerides that is monoglycerides and/or diglycerides of capric acid, caprylic acid, or mixtures thereof. In another embodiment, the additive can include a C8 to C22 fatty acid glycerides that is a monoglycerides and/or diglycerides of linoleic acid, oleic acid, or mixtures thereof. Other examples of C8 to C22 fatty acids that can be used include capric acid, pelargonic acid, caprylic acid, undecanoic acid, lauric acid, myristic acid, palmitic acid, stearic acid, oleic acid, linoleic acid, linolenic acid, arachidonic acid, eicosapentaenoic acid, docosahexanoic acid, and mixtures thereof. In one embodiment, the C8 to C22 fatty acid can be capric acid, caprylic acid, undecanoic acid, lauric acid, myristic acid, palmitic acid, stearic acid, oleic acid, linoleic acid, linolenic acid or mixtures thereof. In another embodiment, the C8 to C22 fatty acid can be selected from the group consisting of capric acid, caprylic acid, oleic acid, linoleic acid, and mixtures thereof. In one embodiment, the composition or capsule fill can be free of ionizable fatty acids. In another embodiment, the composition or capsule fill can be free of oleic acid.

In a further embodiment, the additive can include an alcohol. Non-limiting examples of alcohols that can be used as additives include tocopherol, ethyl alcohol, isopropanol, butanol, benzyl alcohol, ethylene glycol, propylene glycol, butanediol, glycerol, pentaerythritol, transcutol, dimethyl isosorbide, polyethylene glycol and mixtures thereof. In one embodiment, the additive can be ethyl alcohol, benzyl alcohol, tocopherol, and mixtures thereof.

The pharmaceutical compositions and oral dosage units can also include a dispersant. In one aspect of the invention, the dispersant can be a hydrophilic surfactant having an HLB value of greater than 10, a lipophilic surfactant having an HLB value of 10 or less, or combinations thereof. In one embodiment, the compositions and oral dosage forms can include at least one hydrophilic surfactant. In another embodiment the capsule fill includes at least one hydrophilic surfactant and at least one lipophilic surfactant.

Unlike dosage forms containing ionizable components such as fatty acids (e.g. oleic acid), which are prone to being ionized at higher pH values thereby becoming charged and serving as a hydrophilic surfactant, it has been found that for improved bioavailability or activity of androst-4-en-17β-ol-3-one ester for androst-4-en-17β-ol-3-one therapy it can be useful for a composition's performance to be robust with regards to inter-conversion between hydrophilic and hydrophobic species as determined by the absence of ionized ionizable fatty acid due to pH changes such as encountered in the gastro-intestinal tract.

The total amount of lipophilic component is the total amount in wt % of the lipophilic components including the mono-, di- and/or triglycerides and the lipophilic surfactants, if present in the composition. In one embodiment, the lipophilic surfactant includes the additive and the lipophilic surfactant. The total amount of hydrophilic surfactant is the total amount (in wt %) of the added hydrophilic surfactant and that hydrophilic surfactant formed in situ in an aqueous medium as a function of pH (e.g., intestinal pH) due to the hydrophilic ionized ionizable fatty acid (e.g. oleate) formed from lipophilic unionized ionizable fatty acid (e.g. oleic acid).

Therefore, even though fatty acid such as oleic acid may be a good additive for androst-4-en-17β-ol-3-one ester, its bioavailability and activity is substantially compromised with fatty acid containing compositions either by being unable to continue to solubilize the drug or be inadequate facilitator for chylomicron related androst-4-en-17β-ol-3-one ester absorption or can be slow to allow drug to partitioning out of the carrier.

When present, the hydrophilic surfactant can, but does not have to have appreciable solubilizing effect for androst-4-en-17β-ol-3-one ester present in the composition. Non-limiting examples of hydrophilic surfactants that can be included are non-ionic hydrophilic surfactants such as polysorbates, polyoxyethylene hydrogenated vegetable oils, polyoxyethylene vegetable oils; polyoxyethylene sorbitan fatty acid esters; polyoxyethylene-polyoxypropylene block copolymers; polyglycerol fatty acid esters; polyoxyethylene glycerides; polyoxyethylene sterols, derivatives and analogues thereof; reaction mixtures of polyols and at least one member of the group consisting of fatty acids, glycerides, vegetable oils, hydrogenated vegetable oils, fractionated oils and sterols; tocopheryl polyethylene glycol succinates; sugar esters; sugar ethers; sucroglycerides; mixtures thereof; alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers such as poloxamer—108, 188, 217, 238, 288, 338, 407, 124, 182, 183, 212, 331, or 342, or combinations thereof; ionic hydrophilic surfactants such as sodium dodecyl sulphate, docusate sodium; bile acid, cholic acid, deoxycholic acid, chenodeoxycholic acid, salts thereof, and mixtures thereof. In one embodiment, the pharmaceutical composition or oral dosage form can be substantially free of hydrophilic surfactants.

In one embodiment, the hydrophilic surfactant can have at least one characteristic of: 1) being present in an amount such that it does not appreciably solubilize androst-4-en-17β-ol-3-one ester present in the composition; or 2) the solubility of androst-4-en-17β-ol-3-one ester in the hydrophilic surfactant at about 25° C. is less than 100 mg/gram, based on the total weight of the androst-4-en-17β-ol-3-one ester and the additive.

In one embodiment, the hydrophilic surfactant can have at least one characteristic of: 1) being present in an amount such that it solubilizes less than 5 wt % of the androst-4-en-17β-ol-3-one ester present in the composition; or 2) the solubility of androst-4-en-17β-ol-3-one ester in the hydrophilic surfactant at about 25° C. is less than 100 mg/gram, based on the total weight of the androst-4-en-17β-ol-3-one ester and the surfactant. In another embodiment, the hydrophilic surfactant can have at least one characteristic of: 1) the hydrophilic surfactant is present in an amount such that it solubilizes less than 5 wt % of the androst-4-en-17β-ol-3-one ester present in the composition; or 2) the solubility of androst-4-en-17β-ol-3-one ester in the hydrophilic surfactant at about 25° C. is about 50 mg/gram or less, based on the total weight of the androst-4-en-17β-ol-3-one ester and the surfactant. In yet a further embodiment, the hydrophilic surfactant can have a least one characteristic of: 1) the hydrophilic surfactant is present in an amount such that it solubilizes less than 5 wt % of the androst-4-en-17β-ol-3-one ester present in the composition; or 2) the solubility of androst-4-en-17β-ol-3-one ester in the hydrophilic surfactant at about 25° C. is about 10 mg/gram or less, based on the total weight of the androst-4-en-17β-ol-3-one ester and the surfactant. In yet a further embodiment, the hydrophilic surfactant can have the characteristic of: 1) the hydrophilic surfactant is present in an amount such that it solubilizes less than 5 wt % of the androst-4-en-17β-ol-3-one ester present in the composition; and 2) the solubility of androst-4-en-17β-ol-3-one ester in the hydrophilic surfactant at about 25° C. is about 50 mg/gram or less, based on the total weight of the androst-4-en-17β-ol-3-one ester and the surfactant.

As discussed above, in some embodiments the compositions and oral dosage units can include at least one lipophilic surfactant. Various lipophilic surfactants can be used including, but not limited to reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (LABRAFIL M 2125 CS), PEG-6 almond oil (LABRAFIL M 1966 CS), PEG-6 apricot kernel oil (LABRAFIL M 1944 CS), PEG-6 olive oil (LABRAFIL M 1980 CS), PEG-6 peanut oil (LABRAFIL M 1969 CS), PEG-6 hydrogenated palm kernel oil (LABRAFIL M 2130 BS), PEG-6 palm kernel oil (LABRAFIL M 2130 CS), PEG-6 triolein (LABRAFIL M 2742 CS), PEG-8 corn oil (LABRAFIL WL 2609 BS), PEG-20 corn glycerides (CROVOL M40), PEG-20 almond glycerides (CROVOL A40), lipophilic polyoxyethylene-polyoxypropylene block co-polymers (PLURONIC L92, L1OI, L121 etc.); propylene glycol fatty acid esters, such as propylene glycol monolaurate (Lauroglycol FCC), propylene glycol ricinoleate (Propymuls), propylene glycol monooleate (Myverol P-O6), propylene glycol dicaprylate/dicaprate (CAPTEX 200), and propylene glycol dioctanoate (CAPTEX 800), propylene glycol mono-caprylate (CAPRYOL 90); propylene glycol oleate (LUTROL OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (ARLACEL 186); sterol and sterol derivatives such as cholesterol, sitosterol, phytosterol, PEG-5 soya sterol, PEG-JO soya sterol, PEG-20 soya sterol, and the like; glyceryl palmitostearate, glyceryl stearate, glyceryl distearate, glyceryl monostearate, or a combination thereof; sorbitan fatty acid esters such as sorbitan monolaurate (ARLACEL 20), sorbitan monopalmitate (Span-40), sorbitan monooleate (Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; and mixtures thereof. It is important to note that some lipophilic surfactants may also function as the additive component of the compositions and oral dosage forms.

In one embodiment, the lipophilic surfactant can be selected from the group consisting of propylene glycol mono caprylate, propylene glycol oleate, propylene glycol monostearate, propylene glycol monolaurate, propylene glycol mono-oleate, propylene glycol dicaprylate/dicaprate, sorbitan monooleate, PEG-5 hydrogenated castor oil, PEG-7 hydrogenated castor oil, PEG-9 hydrogenated castor oil, PEG-6 corn oil, PEG-6 almond oil, PEG-6 apricot kernel oil, PEG-6 olive oil, PEG-6 peanut oil, PEG-6 hydrogenated palm kernel oil, sorbitan monolaurate (ARLACEL 20), sorbitan monopalmitate, sorbitan monooleate, sorbitan monostearate, sorbitan tristearate, sorbitan monolaurate, sorbitan monopalmitate, sorbitan monooleate, sorbitan trioleate, sorbitan sesquioleate, sorbitan tristearate, sorbitan monoisostearate, and combinations thereof.

In another aspect of the invention, the pharmaceutical compositions and/or oral dosage units, namely the capsule fill, can include a solidifying agent. As defined above, a solidifying agent is a pharmaceutically acceptable additive that is in a solid physical state at room temperature. Typically solidifying agents facilitate the solidification of the pharmaceutical compositions of the present invention at temperatures around room temperature. The compositions and capsule fill of the present invention, including those with solidifying agents, can be non-liquid at standard temperature and pressure. In one embodiment, the composition and capsule fill can be semi-solid at standard temperature and pressure. In yet another embodiment, the composition and capsule fill can be solid at standard temperature and pressure. When present, the solidifying agent can comprise from about 0.1 wt % to about 25 wt % of the pharmaceutical composition or oral dosage capsule. In another embodiment, the solidifying agent can comprise about 2 wt % to about 20 wt % of the composition or oral dosage capsule. In yet a further embodiment, the solidifying agent can comprise about 3 wt % to about 15 wt % of the composition or oral dosage capsule. In still a further embodiment, the solidifying agent can comprise about 3 wt % to about 9 wt % of the capsule fill. In yet a further embodiment, the solidifying agent can comprise 6 wt % to 9 wt % of the capsule fill. In one embodiment, the solidifying agent can melt at a temperature of about 45° C. to about 75° C. Non-limiting examples of solidifying agents that can be used include polyethylene glycols; sorbitol; gelatin; stearic acid; cetyl alcohol; cetosterayl alcohol; paraffin wax; polyvinyl alcohol; glyceryl stearates; glyceryl distearate; glyceryl monostearate; glyceryl palmitostearate; glyceryl behenate; waxes; hydrogenated castor oil; hydrogenated vegetable oil; bees wax, microcrystalline wax; sterols; phytosterols; cholesterol and mixtures thereof. In one embodiment, the solidifying agent includes a polyethylene glycol (PEG) having molecular weight from about 1000 to about 20,000 and their mixtures. In another embodiment the solidifying agent includes one or more selected from the group consisting of polyethylene glycol; gelatin; stearic acid; polyvinyl alcohol; glyceryl stearates; glyceryl distearate; glyceryl monostearate; glyceryl palmitostearate; hydrogenated castor oil; hydrogenated vegetable oil and cholesterol. In one embodiment, the pharmaceutical composition can be a solid at about 20° C. In yet a further embodiment, the solubilized solid and/or the undissolved crystalline androst-4-en-17β-ol-3-one ester can act as a solidifying agent.

The oral compositions of the present invention can be formulated to take any dosage form commonly known in the pharmaceutical arts such as granules, tablet or capsule. In one embodiment, the oral dosage form can be a capsule having a pharmaceutical composition of the present invention disposed therein. Both soft and hard gelatin and non-gelatin capsules can be used. The capsule size can be any size known in the art and can vary depending on the desired dosage amount. In one embodiment, the capsule can be a hard gelatin capsule having a fill volume of about 0.3 mL to about 1.1 mL or about 0.3 ml to about 1.4 ml in a soft gelatin/non gelatin soft capsule. The oral dosage units can be immediate release, extended release, targeted release, enteric release, delayed release dosage form or combinations thereof. In a specific embodiment, the oral dosage capsule can be a delayed release dosage form. In one embodiment, the capsule can have a ratio of the amount of androst-4-en-17β-ol-3-one ester to the volume of the capsule fill can be about 100 mg/mL to about 500 mg/mL. In another embodiment, the capsule can have a ratio of the amount of androst-4-en-17β-ol-3-one ester to the volume of the capsule fill can be about 140 mg/mL to about 420 mg/mL. In further embodiment, the capsule can have a ratio of the amount of androst-4-en-17β-ol-3-one ester to the volume of the capsule fill can be about 250 mg/mL to about 375 mg/mL.

The oral dosage units of the present invention can be formulated such that they have distinctive release profiles. In one embodiment, an oral dosage capsule comprising substantially noncrystalline forms of (17-ß)-3-oxoandrost-4-en-17-yl tridecanoate provides an in vitro release of at least about 75% of the (17-ß)-3-oxoandrost-4-en-17-yl tridecanoate during the first 120 minutes when tested using about 1000 mL of 2% w/v Triton X-100 in water maintained at about 37±1° C. taken in a USP-Type II dissolution apparatus set at 100 rpm. In another embodiment, the oral dosage capsule comprising substantially noncrystalline forms of (17-ß)-3-oxoandrost-4-en-17-yl tridecanoate has an in vitro release profile of at least about 45% of the (17-ß)-3-oxoandrost-4-en-17-yl tridecanoate during 60 minutes, when measured using about 1000 mL of 2% w/v Triton X-100 in water maintained at about 37±1° C. taken in a USP-Type II dissolution apparatus set at 100 rpm. In a further embodiment, the oral dosage capsule comprising substantially noncrystalline forms of (17-ß)-3-oxoandrost-4-en-17-yl tridecanoate has an in vitro release profile of at least 90% of the (17-ß)-3-oxoandrost-4-en-17-yl tridecanoate during 4 hours, when measured using about 1000 mL of 2% w/v Triton X-100 in water maintained at about 37±1° C. taken in a USP-Type II dissolution apparatus set at 100 rpm. In yet a further embodiment, the oral dosage capsule comprising substantially noncrystalline forms of (17-ß)-3-oxoandrost-4-en-17-yl tridecanoate has an in vitro release profile comprising a plurality of the preceding release profiles, and in yet a further embodiment, the oral dosage capsule comprising substantially noncrystalline forms of (17-ß)-3-oxoandrost-4-en-17-yl tridecanoate has an in vitro release profile comprising all of the preceding release profiles.

In yet another aspect, the dosage form comprising two or more of populations of (17-ß)-3-oxoandrost-4-en-17-yl tridecanoate compositions of the present invention is a capsule. In a particular case, the dosage form is a capsule in capsule dosage form. In another particular case the dosage form is a tablet in capsule dosage form. In another particular case, the dosage form is powder or a granules or pellets or tablets or minitablets disposed in a capsule.

The oral dosage units of the present invention can be formulated such that, when administered to a human male, they provide a serum total androst-4-en-17β-ol-3-one $C_{avg}$ ranging about 300 ng/dL to about 1100 ng/dL. In one embodiment, the oral dosage units of the present invention can be formulated such that, when administered to a human male, they provide a serum total androst-4-en-17β-ol-3-one $C_{avg}$ ranging about 300 ng/dL to about 1000 ng/dL. In another embodiment, the oral dosage units can be formulated such that, upon single administration to a human male, they provide a serum total androst-4-en-17β-ol-3-one $C_{avg}$ ranging one of about 300 ng/dL to about 900 ng/dL, about 300 ng/dL to about 800 ng/dL, about 300 ng/dL to about 700 ng/dL, about 300 ng/dL to about 600 ng/dL, about 250 ng/dL to about 900 ng/dL, about 250 ng/dL to about 800 ng/dL, about 250 ng/dL to about 700 ng/dL, and about 250 ng/dL to about 600 ng/dL. In another embodiment, the oral dosage units can be formulated such that, upon single administration to a human male, they provide a serum total androst-4-en-17β-ol-3-one $C_{avg}$ ranging from about 400 ng/dL to about 600 ng/dL. It is noted that such $C_{avg}$ value can be achieved based on administration every 24 hours.

The compositions and oral dosage units disclosed herein can be, but do not have to be, orally administered with food. In one embodiment, the composition or oral dosage capsule can be administered with a meal, such as a meal that provides about 200 to about 1000 calories of energy. In another embodiment, the composition or oral dosage capsule can be administered with a standard meal. In another embodiment, the composition or oral dosage capsule can be administered with a meal that provides about 50% of the calories derived from the fat. In another embodiment, the composition or oral dosage capsule can be administered with a high-fat, high calorie meal. In another embodiment, the composition or oral dosage capsule can be administered with a meal that provides about 500 to about 1000 calories of energy. In another embodiment, the composition or oral dosage capsule can be administered with a meal that provides about 400 to about 700 calories derived from the fat therein. The compositional make-up of the meals that are administered can vary depending on the tastes and dietary needs of a subject. However, in some situations it may be beneficial to administer the compositions and oral dosage forms with meals that provide no fat, up to about 50 g of fat, or up to 50% of calories derived from fat content of the meals. In one embodiment, the meal can provide about 10 g to about 50 g of fat. In yet a further embodiment, the meal can provide about 30 g of fat. The androst-4-en-17β-ol-3-one ester dosage compositions and oral dosage units disclosed herein can be orally administered in a 24 hours' dosing period (also referred to as or a daily dose) that is suitable to the needs of the subject. The 24 hours' dosing period can include administering the dosage forms after meals in the morning, at about noon, in the evening, at about nighttime or combinations thereof. The 24 hours' dosing period can include administering one or more dosage units at one or more administration times. In one embodiment, the pharmaceutical composition is administered as a single oral dosage capsule.

The substantially noncrystalline androst-4-en-17β-ol-3-one ester compositions and oral dosage units can provide increased bioavailability as compared to (mean particle size >1 micron) androst-4-en-17β-ol-3-one ester comprising compositions and dosage forms. For an example, the substantially noncrystalline (17-ß)-3-oxoandrost-4-en-17-yl tridecanoate oral dosage units disclosed herein can provide an in vitro release of less than about 75% or more of the (17-ß)-3-oxoandrost-4-en-17-yl tridecanoate within 120 minutes post injection. The in vitro release is determined in about 1000 mL of 2% w/v Triton X-100 in water maintained at about 37° C. in an USP Type-II Apparatus at about 100 rpm. For another example, the substantially noncrystalline (17-ß)-3-oxoandrost-4-en-17-yl tridecanoate oral dosage units can provide an in vitro release of about 45% or more of (17-ß)-3-oxoandrost-4-en-17-yl tridecanoate within 60 minutes. It has been discovered that these substantially noncrystalline (17-ß)-3-oxoandrost-4-en-17-yl tridecanoate oral dosage units (i.e., those having the above release characteristics) can provide at least a 10% increase in the androst-4-en-17β-ol-3-one AUC after single oral dosages are administered to human males. The increase of bioavailability for the oral dosage units is as compared to the equivalent dosage of substantially crystalline form comprising (17-ß)-3-oxoandrost-4-en-17-yl tridecanoate dosage forms administered under same conditions: See Example 4 and FIG. 3. In another embodiment, the androst-4-en-17β-ol-3-one ester compositions and oral dosage capsules comprising crystalline forms including mean particle size >1 micron can provide increased bioavailability as compared to compositions and dosage forms comprising substantially crystalline forms (mean particle size >1 micron) of androst-4-en-17β-ol-3-one ester.

In another embodiment, the substantially noncrystalline androst-4-en-17β-ol-3-one ester oral dosage units disclosed herein can provide at least a 10% reduction in the inter-subject variability of the androst-4-en-17β-ol-3-one $C_{max}$ and/or the androst-4-en-17β-ol-3-one AUC as compared to the equivalent dosage of substantially crystalline form containing oral dosage forms. In another embodiment, the substantially noncrystalline androst-4-en-17β-ol-3-one ester oral dosage units disclosed herein can provide 10% or more of androst-4-en-17β-ol-3-one bioavailability in subjects as compared to the equivalent dosage of substantially crystalline form comprising oral dosage forms.

Pharmacokinetic Performance

The pharmaceutical compositions and oral dosage units of the present invention can be formulated to administer one or more capsules daily to each subject in a group of at least 24 hypogonadal males for a period of at least 7 days. In one aspect, the pharmaceutical compositions and oral dosage units of the present invention can be formulated to administer one or more capsules daily to each subject in a group of at least 24 hypogonadal males for a period of one of greater than 7 days, greater than 10 days, greater than 13 days, greater than 15 days, greater than 20 days, greater than 25 days, greater than 30 days, greater than 40 days, greater than 50 days, greater than 60 days, greater than 1 month, greater than 2 months, greater than 3 months, greater than 6 months, greater than 1 year, or greater than 2 years.

The pharmaceutical compositions and oral dosage units of the present invention can be formulated to administer one or more capsules daily to each subject in a group of at least 24 hypogonadal males with one or more dose titrations, if needed, until the therapy achieves the therapeutic effectiveness (e.g., ≥75% of subjects with androst-4-en-17β-ol-3-one $C_{avg}$ within the normal range). In one aspect, the pharmaceutical compositions and oral dosage units of the present invention can be administered for a period of at least 7 days (at the steady state of androst-4-en-17β-ol-3-one) for one dose titration, if needed, based on PK performance (e.g., $C_{avg}$, $C_{max}$, $C_t$, or $C_{min}$) per dose. In another aspect, the dose titration, if needed, can be performed at least one of 7 days, 9, days, 11 days, 13 days, 15 days, 21 days, 28 days, 1 month, 2 months, 3 months, 4 months, 5 months, 6 months, 1 year, or 2 years post the start of androst-4-en-17β-ol-3-one ester therapy.

In one embodiment, using a titration metric along with a predetermined threshold criteria, a titration decision may be comprised as follows:

a) the titrated dose is unchanged if androst-4-en-17β-ol-3-one $C_{avg}$ or $C_t$ is one of within 160-350 ng/dL, within 150-500 ng/dL, within 300-550 ng/dL, within 300-600 ng/dL, within 300-700 ng/dL, within 300-800 ng/dL, within 300-900 ng/dL, within 300-1000 ng/dL, within 300-1050 ng/dL, within 300-1080 ng/dL, within 300-1100 ng/dL, within 300-1140 ng/dL, within 300-1200 ng/dL, within 250-500 ng/dL, within 250-600 ng/dL, within 250-700 ng/dL, within 250-800 ng/dL, within 250-850 ng/dL, within 350-600 ng/dL, within 350-700 ng/dL, within 350-800 ng/dL, within 350-900 ng/dL, within 400-600 ng/dL, within 400-700 ng/dL, within 400-800 ng/dL, or within 400-900 ng/dL, within 400-1050 ng/dL, within 450-900 ng/dL, within 450-1000 ng/dL, within 450-1100 ng/dL, or within 450-1200 ng/dL, or b) the titrated dose of androst-4-en-17β-ol-3-one ester dose as androst-4-en-17β-ol-3-one equivalent amount is up-titrated by an increase of one of about 50 mg or greater, about 60 mg or greater, about 75 mg or greater, about 97 mg or greater, about 107 mg or greater, about 119 mg or greater, about 149 mg or greater, about 179 mg or greater, about 198 mg or greater, about 208 mg or greater, about 223 mg or greater, about 238 mg or greater, about 268 mg or greater or about 298 mg or greater. In an aspect, the current androst-4-en-17β-ol-3-one ester dose as androst-4-en-17β-ol-3-one equivalent amount is up-titrated by an increase of at least 20% of the current dose of androst-4-en-17β-ol-3-one ester, such as about 20%, about 25%, about 30%, about 33%, about 40%, about 45%, about 50%, about 60%, about 75%, about 80%, about 90%, or about 100% if androst-4-en-17β-ol-3-one $C_{avg}$ or $C_t$ is one of less than about 150 ng/dL, about 200 ng/dL, about 250 ng/dL, less than about 300 ng/dL, less than about 350 ng/dL, less than about 400 ng/dL, less than about 420 ng/dL, or less than about 450 ng/dL based on the titration metric, or c) the titrated dose of androst-4-en-17β-ol-3-one ester dose as androst-4-en-17β-ol-3-one equivalent amount is down-titrated by a decrease of one of about 50 mg or greater, about 60 mg or greater, about 75 mg or greater, about 97 mg or greater, about 107 mg or greater, about 119 mg or greater, about 149 mg or greater, about 179 mg or greater, about 198 mg or greater, about 208 mg or greater, about 223 mg or greater, about 238 mg or greater, about 268 mg or greater or about 298 mg or greater. In an aspect, the current androst-4-en-17β-ol-3-one ester dose as androst-4-en-17β-ol-3-one equivalent amount is up-titrated by a decrease of at least 20% of the current dose of androst-4-en-17β-ol-3-one ester, such as about 20%, about 25%, about 30%, about 33%, about 40%, about 45%, about 50%, about 60%, about 75%, about 80%, or about 90% if androst-4-en-17β-ol-3-one $C_{avg}$ or $C_t$ is one of greater than about 500 ng/dL, greater than about 550 ng/dL, greater than about 600 ng/dL, greater than about 650 ng/dL, greater than about 700 ng/dL, greater than about 800 ng/dL, greater than about 850 ng/dL, greater than about 900 ng/dL, greater than about 1000 ng/dL, greater than about 1050 ng/dL, greater than about 1080 ng/dL, greater than about 1100 ng/dL, greater than about 1140 ng/dL, or greater than about 1200 ng/dL based on the titration metric, or d) any combinations thereof.

In one embodiment, the titration metric can comprise a maximum androst-4-en-17β-ol-3-one concentration ($C_{max}$) measured for a 24-hr per daily period in the steady state post the dose administration. In another embodiment, a titration metric can comprise an average androst-4-en-17β-ol-3-one concentration ($C_{avg}$) measured for a 24-hr per daily period in the steady state post the dose administration.

In one embodiment, the titration metric can comprise a single androst-4-en-17β-ol-3-one concentration measured at time t ($C_t$) in the steady state post the dose administration, such as at least one of about 4 hrs, about 5 hrs, about 6 hrs, about 7 hrs, about 8 hrs, about 9 hrs, about 10 hrs, about 11 hrs, about 12 hrs, about 14 hrs, about 16 hrs, about 18 hrs, about 20 hrs, and any combinations thereof post the dose administration.

In one embodiment, the titration metric can comprise a single pre-dose androst-4-en-17β-ol-3-one concentration measured before the dose administration, such as at one of about 1 hr, about 30 min, about 20 min, about 10 min, about 5 min, or about 1 min before the dose administration.

In one embodiment, after the first dose titration, if/as needed, from the initial dose of androst-4-en-17β-ol-3-one ester, the pharmaceutical compositions and oral dosage units of the present invention can provide one of at least 75%, at least 80%, at least 83%, at least 86%, at least 88%, at least 90%, at least 92%, at least 94%, at least 95%, and at least 96% of hypogonadal subjects with androst-4-en-17β-ol-3-one $C_{avg}$ within the normal range when administered to a group of subjects if the initial dose of androst-4-en-17β-ol-3-one ester ranges from 149 mg to 893 mg of androst-4-en-17β-ol-3-one equivalent amount upon a titration metric. The normal range of serum androst-4-en-17β-ol-3-one levels is typically 300 ng/dL to 1100 ng/dL, however its practical normal range depends on a bioanalytical lab performing the measurement of androst-4-en-17β-ol-3-one concentration from blood samples in clinical sites. For example, the normal range of androst-4-en-17β-ol-3-one can be selected from one of about 300-about 1150 ng/dL, about 300-about 1100 ng/dL, about 300-about 1080 ng/dL, about 300-about 1000 ng/dL, about 300-about 900 ng/dL, about 300-about 800 ng/dL, about 250-about 1000 ng/dL, and about 250-about 900 ng/dL, depending on the bioanalytical lab, types of blood sample collection tubes, and/or an analytical method.

In another embodiment, after the first dose titration, if/as needed, from the initial dose of androst-4-en-17β-ol-3-one ester, the pharmaceutical compositions and oral dosage units of the present invention can provide one of at least 75% at least 80%, at least 83% at least 86% at least 88%, at least 90%, at least 92%, at least 94%, and at least 96% of hypogonadal subjects with androst-4-en-17β-ol-3-one $C_{avg}$ within the normal range if the initial dose of androst-4-en-17β-ol-3-one ester ranges from 149 mg to 893 mg of androst-4-en-17β-ol-3-one equivalent amount upon an application of the inventive method.

In other embodiment, after dose titration(s), if/as needed, from the initial dose of androst-4-en-17β-ol-3-one ester, the pharmaceutical compositions and oral dosage units of the present invention can provide one of at least 75%, at least 80%, at least 83%, at least 86%, at least 88%, at least 90%, at least 92%, at least 94%, and at least 96% of hypogonadal subjects with androst-4-en-17β-ol-3-one $C_{avg}$ within the normal range if the initial dose of androst-4-en-17β-ol-3-one ester ranges from 250 mg to 744 mg of androst-4-en-17β-ol-3-one equivalent amount upon a titration metric.

In one embodiment, after dose titration(s), if needed, from the initial dose of androst-4-en-17β-ol-3-one ester, the pharmaceutical compositions and oral dosage units of the present invention can achieve the androst-4-en-17β-ol-3-one $C_{max}$ performance target of androst-4-en-17β-ol-3-one $C_{max}$ greater than 2.5×ULN in about 1% or less, about 2% or less, or about 3% or less of the hypogonadal males in the group if the initial dose of androst-4-en-17β-ol-3-one ester as androst-4-en-17β-ol-3-one equivalent amount is one of about 149 mg, about 179 mg, about 200 mg, about 250 mg, about 268 mg, about 300 mg, about 328 mg, about 400 mg, about 415 mg, about 445 mg, about 475 mg, about 505 mg, about 535 mg, about 565 mg, about 600 mg, about 745 mg, about 775 mg, about 850 mg, and about 895 mg upon a titration metric. The ULN can vary depending on the assay employed (e.g., 2.5×ULN is 2500 ng/dL if ULN is 1000 ng/dL).

In one embodiment, the present oral compositions and dosage forms can provide a serum androst-4-en-17β-ol-3-one $C_{avg}$ of 300 ng/dL to 1100 ng/dL in at least 75% of the hypogonadal males in the group. Additionally, in one aspect, under such an administration regimen the present oral compositions and dosage forms in an embodiment, can provide a serum androst-4-en-17β-ol-3-one $C_{max}$ greater than 2.5× ULN in about 3% or less of the hypogonadal males in the group. In one embodiment, the administration over at least 7 days can be divided into multiple dosages including an initial dosage in which an initial dose is administered and titrated dosages, if needed, in which one, two, or three titrated doses may be administered. In one aspect of this embodiment, the dose of the titrated dosage of the androst-4-en-17β-ol-3-one ester can be about 20% up to about 300% of the initial dose. In another aspect of the embodiment, the dose of the titrated dosage of the androst-4-en-17β-ol-3-one ester can be about 25% up to about 250% of the initial dose. In another aspect of the embodiment, the dose of the titrated dosage of the androst-4-en-17β-ol-3-one ester can be about 30% up to about 200% of the initial dose or any value therebetween (i.e., 100%=no change from the initial dose). In yet a further aspect of this embodiment, the present oral compositions and dosage forms can be formulated such that the amount of the dose of the titrated dosage is determined based on at least one dose titration metric derived from the measurement of the blood androst-4-en-17β-ol-3-one PK parameters (e.g. androst-4-en-17β-ol-3-one $C_{avg}$, androst-4-en-17β-ol-3-one $C_{max}$, androst-4-en-17β-ol-3-one $C_t$, or androst-4-en-17β-ol-3-one $C_p$re-dose) on at least one titration node day. The titration node day can be any single day beginning on at least day 7 after administration of the initial dose. In one embodiment, the first titration node day can be any day from day 7 to day 28 after administration the initial dose. In yet another embodiment, the second titration node day is any day from day 14 to day 60 after administration of the initial dose. In further embodiments, the third titration node day can be any day from one of day 21 to day 90, from day 28 to day 90, or from day 42 to day 90 after administration of the initial dose of.

In one aspect, the titration, if needed, based on the titration metric can comprise androst-4-en-17β-ol-3-one concentration at time t (i.e., $C_t$) post a single dose administration. In other words, the testing of the titration metric is performed based on androst-4-en-17β-ol-3-one $C_t$ at any time point between 4 hours to 18 hours following administration. For example, if the androst-4-en-17β-ol-3-one $C_{10}$ (serum concentration measured at 10 hours post dose) is less than 400 ng/dL then the androst-4-en-17β-ol-3-one ester dose may need to be up-titrated, and if the androst-4-en-17β-ol-3-one $C_{10}$ is greater than 1050 ng/dL then the androst-4-en-17β-ol-3-one ester dose may need to be down-titrated. For another example, if androst-4-en-17β-ol-3-one $C_{12}$ (serum concentration measured at 12 hours post dose) is less than 250 ng/dL then the androst-4-en-17β-ol-3-one ester dose may need to be up-titrated, and if androst-4-en-17β-ol-3-one $C_{12}$ is greater than 850 ng/dL then the androst-4-en-17β-ol-3-one ester dose may need to be down-titrated. For the other example, if the androst-4-en-17β-ol-3-one $C_4$ (serum concentration measured at 4 hours post dose) is less than 150 ng/dL then the androst-4-en-17β-ol-3-one ester dose may need to be up-titrated, and if the androst-4-en-17β-ol-3-one $C_4$ is greater than 550 ng/dL then the androst-4-en-17β-ol-3-one ester dose may need to be down-titrated. For a further example, if the androst-4-en-17β-ol-3-one $C_6$ is less than 300 ng/dL then the androst-4-en-17β-ol-3-one ester dose may need to be up-titrated, and if the androst-4-en-17β-ol-3-one $C_6$ is greater than 800 ng/dL then the androst-4-en-17β-ol-3-one ester dose may need to be down-titrated. For additional further example, if the androst-4-en-17β-ol-3-one $C_{18}$ is less than 160 ng/dL then the androst-4-en-17β-ol-3-one ester dose may need to be up-titrated, and if the androst-4-en-17β-ol-3-one $C_6$ is greater than 350 ng/dL then the androst-4-en-17β-ol-3-one ester dose may need to be down-titrated. The above titrations are only exemplary of possible titrations that can be accomplished using the methods of the present invention. It is further noteworthy that the titrations can be used in conjunction with the methods taught herein including the disclosed methods of providing a concentration of androst-4-en-17β-ol-3-one within a target androst-4-en-17β-ol-3-one $C_{avg}$ range for a male subject.

Pharmacodynamic Performance

The androst-4-en-17β-ol-3-one ester compositions and oral dosage forms disclosed herein can be used in conjunction with or as a component of a diagnostic or treatment kit that enables the diagnosis and treatment of a male patient in need of androst-4-en-17β-ol-3-one therapy. The diagnostic or treatment kit may comprise the androst-4-en-17β-ol-3-one ester composition or oral dosage forms disclosed herein along with one or more other components, including, but not limited to 1) instructions to enable those ordinarily skilled in the art to prepare a dosage form for immediate dispensing to the subject in need of; 2) one or more containers filled with one or more of the ingredients of the oral pharmaceutical dosage forms of the invention. Suitable containers include, for example, a bottle, a box, a blister card, a foil packet, or a combination thereof; 3) a tamper proof container or packaging; 4) other pharmaceutical dosage forms including other active agents including PDE-5 inhibitors and glucocorticosteroids; 5) Notice or printed instructions: in a form prescribed by a governmental agency regulating the manufacture, use, or sale of pharmaceuticals or biological products, which notice reflects approval by the agency of the manufacture, use, or sale for human administration to treat a condition that could be treated by oral androst-4-en-17β-ol-3-one therapy; 6) A "planner" for monitoring and tracking administration of the oral dosage forms; 7) Containers for storing and transporting the components of the kit; 8) total androst-4-en-17β-ol-3-one or free androst-4-en-17β-ol-3-one testing kits; 9) Sex Hormone binding globulin, SHBG, testing kits; 10) Body mass index testing materials to identify high risk patients; 11) tests for identifying patients with hypogonadism; 12) tests to assess testicular function or impotency; 13) test for bone mineral density/osteoporosis; 14) test for hair density 15) test for muscle mass and strength; 16) test for determining erectile dysfunction; 17) test for decreased libido; 18) test for fatigue, depression, mood disorders or irritability; 19) test for infertility; 20) test for prostate condition.

The oral dosage compositions and oral dosage forms disclosed herein can be co-administered with other active agents in order to treat a target condition. One or more coadministered active agents can be admixed with the (17-ß)-3-oxoandrost-4-en-17-yl tridecanoate containing compositions and/or oral dosage forms of the current invention. For example, phosphodiesterase type 5 (PDE-5) inhibitors, such as sildenafil citrate, tadalafil, vardenafil, avanafil, lodenafil, mirodenafil, udenafil, and the like, are used to block the degradative action of phosphodiesterase type 5 enzyme on cyclic GMP in the smooth muscle cells lining the blood vessels supplying the corpus cavernosum of the penis and are frequently used to treat erectile dysfunction. Such compounds could be co-administered with the compositions and oral dosage forms of the present invention in order to provide improved clinical outcomes through synergistic pharmacological action as measured by improved (sooner, better and longer lasting) erection, potency, libido, mood, body mass, etc. in males relative to administration of the androst-4-en-17β-ol-3-one or the co-administered PDE-5 alone. The androst-4-en-17β-ol-3-one ester compositions and oral dosage forms can also be co-administered with one or more other active agents such as aromatase inhibitors (for example letrozole, anastrozole, exemestane, fadrozole, vorozole, formestane etc.), dopamine agonists (for example apomorphine, bromocriptine, cabergoline, pergolide, ropinirole, rotigotine, pramipexole, fenoldopam etc.), prostaglandins (for example alprostadil), alpha blockers (for example yohimbine, phentolamine), vasodilators (for example minoxidil) and the like, for improved clinical outcomes through synergistic pharmacological action as measured by improvements in one or more of the secondary sexual characteristics in males such as sexual activity, potency, libido, erection etc., mood, body mass and the like, relative to administration of either the androst-4-en-17β-ol-3-one or the co-administered active agent alone.

In another aspect, the subjects receiving the dosage form of this invention are expected to improve in quality of life. The patient reported outcome may be employed to measure the improvement in other levels apart from primary (androst-4-en-17β-ol-3-one $C_{avg}$) and secondary (androst-4-en-17β-ol-3-one $C_{max}$, $C_{min}$, $C_{trough}$, etc.) outcomes which are typically quantified by the PK profiles. For measuring the pharmacodynamic related efficacy outcomes, the improvements in the symptoms are usually monitored by ranking or scoring, dairy recording etc., by the subject being treated and/or the partner or spouse of the subject, in a timely manner before and during the therapy.

Accordingly, in one embodiment the dosage forms and the methods of current invention improve sexual symptoms including but not limited to sexual activity engagement, sexual thoughts or fantasies; feel of sexual desire; frequency of experience of morning erections; maintaining erections as long as desired; hardness of erection; ejaculation; enjoyment/satisfaction of sexual activity. In another embodiment the dosage form and the method of the current invention improves or enhances the physical and physiological symptoms and body energy level as assessed by the level of happiness with the body looks; body muscle mass, body weight and weakness/strength of muscles; level of tiredness; level of physical tiredness; level of energy; level of exhaustion and the like.

In another embodiment, the dosage form and the methods of the current invention improves the symptoms related to the sleep symptoms and memory/cognition as assessed by quality of sleep at night; frequency of sleep restfulness; number of wake-up times during the night; frequency of feeling of satisfactory rest, frequency of accidental doze off during the day; frequency of purposely taken naps during the day; focus attention to tasks; level of forgetfulness; desire or ambition to take on new projects; short attention span; successful/efficient completion of tasks.

Compositions and Methods Comprising Androst-4-en-17β-ol-3-one Ester

In a further aspect, the compositions of the current invention can be formulated to provide a gastro-retentive dosage form. In one embodiment, the gastro-retentive dosage form is a capsule. In another embodiment, the gastro-retentive dosage form is retained in the upper gastro-intestinal tract for at least one hour post-dosing. In another embodiment, the gastro-retentive dosage form is retained in the upper gastro-intestinal tract for at least two hours post-dosing. In another embodiment, the gastro-retentive dosage form is retained in the upper gastro-intestinal tract for at least 4 hours post-dosing. In another embodiment, the gastro-retentive dosage form is formulated to float in the stomach after dosing. In another embodiment, the gastro-retentive dosage form is formulated to expand when it comes in contact with aqueous medium to at least 1.3 times its size compared to its size when it is not in contact with the aqueous use environment. In another embodiment, the gastro-retentive dosage form is formulated to adhere to the lining of the stomach wall after dosing.

The compositions and the oral dosage forms of the current invention can also include one or more of other additives selected from binders, bufferants, diluents, disintegrants, flavors, colorants, taste-masking agents, resins, pH modifiers, lubricants, glidants, thickening agent, opacifying agent, humectants, desiccants, effervescing agents, plasticizing agents and the like.

In addition to the compositions and oral dosage forms of the present invention, a method for providing a serum concentration of androst-4-en-17β-ol-3-one within a target serum androst-4-en-17β-ol-3-one concentration $C_{avg}$ and/or $C_{max}$ range for a male subject is also provided. It is noted that the compositions and oral dosage units of the present invention can be used in the conjunction with this method and that the teachings regarding the compositions and their administration provided above can be applied and used in connection with the methods disclosed here. The method includes the step of orally administering to the male subject an initial dosage including a dose of an androst-4-en-17β-ol-3-one ester containing composition. The androst-4-en-17β-ol-3-one ester in the composition can comprise about 14 wt % to about 42 wt % of the composition and the initial androst-4-en-17β-ol-3-one equivalent dose amount can comprise about 150 mg to about 893 mg to the male subject. After the initial dosage, the method includes a step of determining a dose titration metric based on a measurement of androst-4-en-17β-ol-3-one concentration for the male subject on at least one titration node day with the initial dosage. The method further includes a titrated dosage determined by the titration metric comprising androst-4-en-17β-ol-3-one concentration and androst-4-en-17β-ol-3-one equivalent titration amount. The titrated dosage provides a dose of androst-4-en-17β-ol-3-one ester to the subject based on the titration metric determined on the at least one titration node day of the initial dosage and is sufficient to provide total androst-4-en-17β-ol-3-one concentration that is closer to or within the PK performance target range.

In one embodiment, the method for providing a serum concentration of androst-4-en-17β-ol-3-one within a target androst-4-en-17β-ol-3-one $C_{avg}$ range for a male subject can further include the steps of determining a dose titration metric based on a measurement of androst-4-en-17β-ol-3-one concentration for the male subject on at least one titration node day with the titrated or maintained dosage, if/as needed. Following the determination of the titration metric the method includes the step of orally administering to the male subject a second titrated or maintained dosage, if/as needed, including a titrated or maintained dose of androst-4-en-17β-ol-3-one ester, wherein the androst-4-en-17β-ol-3-one ester comprises about 14 wt % to about 42 wt % of the composition. The second titrated or maintained dosage provides a dose of androst-4-en-17β-ol-3-one ester to the subject based on the titration metric determined on at least one titration node day of the titrated or maintained dosage sufficient to provide a serum androst-4-en-17β-ol-3-one plasma concentration within the PK performance target range. Following the second titrated or maintained dosage, if needed, the steps of determining the titration metric and administering an additional titrated dosage can be repeated as needed in order to achieve androst-4-en-17β-ol-3-one concentration within the PK performance target range.

In the above method, the dose administered in the initial dosage can be the same dose amount as the dose administered post titration (i.e., maintenance dose). In one embodiment, the dose of the titrated dosage, if needed, can provide an amount of androst-4-en-17β-ol-3-one ester that is about 20% to about 300% of that of the initial dose. In another embodiment, the dose of the titrated dosage, if needed, can provide an amount of androst-4-en-17β-ol-3-one ester that is about 25% to about 250% of that of the dose in the initial dosage. In yet another embodiment, the dose of the titrated dosage, if needed, can provide an amount of androst-4-en-17β-ol-3-one ester that is about 30% to about 200% of that of the dose in the initial dosage.

In one embodiment, the titration amount (i.e. the amount of change) as androst-4-en-17β-ol-3-one equivalent amount can be one of at least about ±50 mg, about ±60 mg, about ±75 mg, about ±97 mg, about ±107 mg, about ±119 mg, about ±149 mg, about ±179 mg, about ±198 mg, about ±208 mg, about ±223 mg, about ±238 mg, about ±268 mg, or about ±298 mg from initial dose or current titrated/maintained dose.

The determination step or steps of the above described titration methods can be performed from at least day 7 post administration of the initial dose. In one embodiment, the first titration node day can be any single day from day 7 to day 30 following the initial dose. In another embodiment, the second titration node day can be any single day from day 14 to day 60 following the initial dose. In yet a further embodiment, the third titration node day is any single day from day 21 to day 90 following the initial dose. In still a further embodiment, the titration node day can be any single day from day 7 to day 90 following the initial dose.

As discussed previously, subjects with whom the methods of the present invention can be used can be those in need of androst-4-en-17β-ol-3-one therapy. In one aspect, the male subject with whom the method is being used can have androst-4-en-17β-ol-3-one $C_{avg}$ or a single point $C_t$ of less than 300 ng/dL before the initial dose. In another aspect, the male subject can have androst-4-en-17β-ol-3-one $C_{avg}$ or a single point $C_t$ of less than 250 ng/dL before the initial dose. In yet another aspect, the male subject can have a serum androst-4-en-17β-ol-3-one $C_{avg}$ or a single point $C_t$ of less than 300 ng/dL before beginning of the post-titration dosage. In yet a further aspect, the male subject can have androst-4-en-17β-ol-3-one $C_{avg}$ or a single point $C_t$ of less than 250 ng/dL before beginning of the post-titration dosage. The target androst-4-en-17β-ol-3-one $C_{avg}$ or a single point $C_t$ range can vary depending on the subject, his particular needs, physiological parameters, bioanalytical lab, blood sample tubing types, and a bioanalytical method. In one embodiment, the target androst-4-en-17β-ol-3-one $C_{avg}$ or a single point $C_t$ range can be about 300 ng/dL to 1100 ng/dL and is achieved by the titration method on or after about day 7 following the initial dose. In another embodiment, the target androst-4-en-17β-ol-3-one $C_{avg}$ or a single point $C_t$ range can be about 300 ng/dL to about 1100 ng/dL and is achieved by the titration method after at least day 7 to day 180 following the initial dose. In yet a further embodiment, the target androst-4-en-17β-ol-3-one $C_{avg}$ or a single point $C_t$ range can be about 300 ng/dL to about 1100 ng/dL and can be achieved by the titration method on or after day 7 to day 90 following the initial dose.

The above described method can provide desirable pharmacokinetic parameters based on administration to a group of subjects. In one embodiment, the method of the present invention can be such that the method can provide androst-4-en-17β-ol-3-one $C_{avg}$ in the range of 300 ng/dL to 1100 ng/dL in 75% or more of hypogonadal males after at least day 7 from the initial dose. In yet a further embodiment, the method can provide androst-4-en-17β-ol-3-one $C_{max}$ of greater than 2.5 times ULN (upper limit of normal lab range) in about 3% or less of hypogonadal males after at least 7 days from the initial dose.

The above disclosed methods provide for the initial and titrated dosages of the regimen that include dose amounts that can be provided as once-a-day, twice-a-day administrations, or divided into multi-dosage administrations. When a multi-dosage administration is utilized to provide the dose amount of androst-4-en-17β-ol-3-one ester the dosages can be equal or unequal and can be administered with or without meals, depending on the designated dosage. In one aspect, when the dosages, whether once-a-day, twice-a-day, or multi-time dosages, are administered with a meal or a snack the meal or snack can include about 15 g to about 60 g of fat. In one embodiment, the method provides for administration of the dose during the titrated dosage as including once-a-day or twice-a-day administration of the androst-4-en-17β-ol-3-one ester containing composition in conjunction with meals. In one embodiment, the meal administered with the androst-4-en-17β-ol-3-one ester containing composition can have a total calorie content of about 420 and 1200 K calories with about 30% to about 60% of the calories in the meal being derived from fat.

Example 1. Composition Examples

In one embodiment, the oral compositions of the current invention include androst-4-en-17β-ol-3-one ester, such as (17-ß)-3-oxoandrost-4-en-17-yl tridecanoate or a combination of (17-ß)-3-oxoandrost-4-en-17-yl tridecanoate and one of (17-ß)-3-oxoandrost-4-en-17-yl undecanoate and (17-ß)-3-oxoandrost-4-en-17-yl dodecanoate, and at least one pharmaceutically acceptable carrier, wherein androst-4-en-17β-ol-3-one ester comprises about 14 wt % to about 42 wt % of the composition or the dosage form, and the carrier includes at least one of a lipophilic additive, a hydrophilic additive, other additives, and a combination thereof. Table A shows typical components and their relative proportions that can be utilized in the compositions of the present inventions having androst-4-en-17β-ol-3-one ester.

TABLE A

Oral compositions comprising androst-4-en-17β-ol-3-one ester

| Carrier component | Composition (% w/w) | | | | | |
|---|---|---|---|---|---|---|
| | A1 | A2 | A3 | A4 | A5 | A6 |
| androst-4-en-17β-ol-3-one ester* | 14-20 | 16-25 | 14-20 | 20-35 | 20-35 | 35-42 |
| Lipophilic additive (e.g. vitamin E or its derivatives, glyceryl fatty acid ester, polyglycerol fatty acid ester, triglycerides, propylene glycol fatty acid ester, fatty acid or its salt, edible oil, etc.) | 50-80 | 55-80 | 35-80 | 45-80 | 40-60 | 40-65 |
| Hydrophilic additive (e.g. polyoxyl vegetable oil or glycerides, PEG glycerides of fatty acid, polyglycerol fatty acid esters, polysorbates, TPGS, etc.) | 0-30 | 0-20 | 5-45 | 0-20 | 0-40 | 0-25 |
| Other additives (e.g. co-solvents, anti-oxidant, other functional additives, or combinations thereof) | q.s. | q.s. | q.s. | q.s. | q.s. | q.s. |

*androst-4-en-17β-ol-3-one ester can be (17-β)-3-oxoandrost-4-en-17-yl tridecanoate only, a combination of (17-β)-3-oxoandrost-4-en-17-yl undecanoate and at least 25% of the total ester as (17-β)-3-oxoandrost-4-en-17-yl tridecanoate, or a combination of (17-β)-3-oxoandrost-4-en-17-yl dodecanoate and at least 25% of the total ester as (17-β)-3-oxoandrost-4-en-17-yl tridecanoate.

Example 2. Dosage Form Examples

The present oral androst-4-en-17β-ol-3-one ester compositions herein can be formulated with substantially noncrystalline or crystalline form of androst-4-en-17β-ol-3-one ester (i.e., (17-ß)-3-oxoandrost-4-en-17-yl tridecanoate only, a combination of (17-ß)-3-oxoandrost-4-en-17-yl undecanoate and at least 25% of the total ester as (17-ß)-3-oxoandrost-4-en-17-yl tridecanoate, or a combination of (17-ß)-3-oxoandrost-4-en-17-yl dodecanoate and at least 25% of the total ester as (17-ß)-3-oxoandrost-4-en-17-yl tridecanoate) with at least one carrier to deliver the therapeutically effective amount of androst-4-en-17β-ol-3-one in the body on treatment of androst-4-en-17β-ol-3-one deficiency.

Table B displays the various oral dosage forms comprising crystalline and noncrystalline androst-4-en-17β-ol-3-one ester and select examples of them were tested in the clinical studies described in this disclosure.

TABLE B

Oral dosage forms comprising androst-4-en-17β-ol-3-one ester and carrier components

| Component | Composition of Dosage Form (w/w %) | | | | | | | | | | | |
|---|---|---|---|---|---|---|---|---|---|---|---|---|
| | B1 | B2 | B3 | B4 | B5 | B6 | B7 | B8 | B9 | B10 | B11 | B12 |
| androst-4-en-17β-ol-3-one ester† | 15.0 | 17.5 | 20.0 | 20.0 | 24.4 | 24.4 | 28.0 | 28.0 | 33.0 | 33.0 | 42.0 | 47.8 |
| Glyceryl monolinoleate (an example of mono- or mono/diglyceride)* | 63.2 | | | 12.0 | | 10.0 | | | | | | |
| Peppermint oil (an example of edible oil)** | | 56.5 | | 18.2 | | | 7.0 | | | | 12.0 | |
| Lauroglycol (an example of propylene glycol monolaurate) | | 5.0 | | | | | | 4.0 | | | | |
| Oleic acid (an example of fatty acid)*** | | | | | 41.2 | 55.8 | | | | | | |
| Stearic acid (an example of fatty acid)*** | | | | | | 4.0 | | | | | | |
| Lecithin | | 3.0 | | 4.0 | | | | | | | 5.0 | |
| Alpha-tocopherol | | | 48.0 | | | | | | 55.0 | | 35.0 | |
| TPGS | | 3.0 | | | | 5.0 | | 4.0 | | | | |
| Sodium lauryl sulfate | | | | 4.0 | | | | 4.0 | | 5.0 | | 4.0 |
| KOLLIPHOR RH40 (an example of | 15.6 | 15.0 | 26.0 | 4.0 | | 4.0 | | 5.0 | | | | |

TABLE B-continued

Oral dosage forms comprising androst-4-en-17β-ol-3-one ester and carrier components

| Component | B1 | B2 | B3 | B4 | B5 | B6 | B7 | B8 | B9 | B10 | B11 | B12 |
|---|---|---|---|---|---|---|---|---|---|---|---|---|
| pegylated castor oil) | | | | | | | | | | | | |
| Microcrystalline cellulose | | | | 49.0 | | 42.0 | | 45.0 | | 45.0 | | 33.0 |
| Polyvinylpyrrolidone | | | | 21.0 | | 18.0 | | 16.0 | | 17.0 | | 15.2 |
| Glyceryl distearate (an example of solidifier) | | | 6.0 | | 12.0 | | 8.0 | | 6.0 | | 6.0 | |
| PEG 8000 (an example of hydrophilic additives) | 6.0 | | | | | | | | | | | |
| Other additives | q.s. | q.s. | q.s. | q.s. | q.s. | q.s. | q.s. | q.s. | q.s. | q.s. | q.s. | q.s. |

†androst-4-en-17β-ol-3-one ester can be (17-β)-3-oxoandrost-4-en-17-yl tridecanoate only, a combination of (17-β)-3-oxoandrost-4-en-17-yl undecanoate and at least 25% of the total ester as (17-β)-3-oxoandrost-4-en-17-yl tridecanoate, a combination of (17-β)-3-oxoandrost-4-en-17-yl dodecanoate and at least 25% of the total ester as (17-β)-3-oxoandrost-4-en-17-yl tridecanoate, or a combination of (17-β)-3-oxoandrost-4-en-17-yl undecanoate and (17-β)-3-oxoandrost-4-en-17-yl dodecanoate.
*Glyceryl monolinoleate may be replaced to, but not limited, C8 to C22 medium and/or long chain monoglycerides, medium and/or long chain diglycerides, or mixtures of medium and/or long chain monoglycerides and medium and/or long chain diglycerides.
**Peppermint oil may be replaced to, but not limited, peanut oil, safflower oil, sunflower oil, olive oil, castor oil, corn oil, maize oil, coconut oil, palm kernel oil, flax seed oil, wheat-germ oil, omega-3 oil, cottonseed oil, sesame oil, soybean oil, and the like.
***Oleic acid or stearic acid may be replaced to, but not limited, caprylic acid, capric acid, lauric acid, myristic acid, palmitic acid, and arachidic acid.

For example, dosage forms of B4, B6, B8, B10, and B12 comprise substantially crystalline forms (mean particle size >1 micron) of androst-4-en-17β-ol-3-one ester, while dosage forms of B1, B2, B3, B5, B7, B9, and B11 comprise substantially noncrystalline forms (partially or fully solubilized or amorphous or crystalline form with mean particle size less than 1 micron) of androst-4-en-17β-ol-3-one ester.

For other examples, Table B-1 displays the various oral dosage forms comprising noncrystalline forms of a combination of (17-ß)-3-oxoandrost-4-en-17-yl undecanoate and (17-ß)-3-oxoandrost-4-en-17-yl tridecanoate.

TABLE B-1

Oral dosage forms comprising a combination of (17-β)-3-oxoandrost-4-en-17-yl undecanoate and (17-β)-3-oxoandrost-4-en-17-yl tridecanoate, and carrier components

| Component | BB1 | BB2 | BB3 | BB4 | BB5 | BB6 | BB7 | BB8 | BB9 | BB10 | BB11 | BB12 |
|---|---|---|---|---|---|---|---|---|---|---|---|---|
| Total androst-4-en-17β-ol-3-one ester | | 15.0 | | | 24.4 | | | 30.0 | | | 38.0 | |
| (17β)-3-oxoandrost-4-en-17-yl undecanoate | 3.4 | 4.6 | 2.6 | 5.6 | 7.5 | 4.3 | 6.9 | 8.2 | 5.3 | 6.9 | 9.3 | 5.3 |
| (17β)-3-oxoandrost-4-en-17-yl tridecanoate | 11.6 | 10.4 | 12.4 | 18.8 | 16.9 | 20.1 | 23.1 | 21.8 | 24.7 | 31.1 | 28.7 | 32.7 |
| Glyceryl monolinoleate (an example of mono- or mono/diglyceride* | 63.2 | 63.2 | 63.2 | | | | | | | | | |
| Peppermint oil (an example of edible oil)** | | | | 18.2 | 18.2 | 18.2 | | | | | | |
| Oleic acid (an example of fatty acid)*** | | | | 41.2 | 41.2 | 41.2 | 53.8 | 53.8 | 53.8 | | | |
| Stearic acid (an example of fatty acid)*** | | | | | | | 4 | 4 | 4 | | | |
| Alpha-tocopherol | | | | | | | | | | 50.0 | 50.0 | 50.0 |
| KOLLIPHOR RH40 (an example of pegylated castor oil) | 15.6 | 15.6 | 15.6 | 4 | 4 | 4 | 4 | 4 | 4 | 5 | 5 | 5 |
| Glyceryl distearate (an example of solidifier) | | | | 12 | 12 | 12 | 8 | 8 | 8 | 6 | 6 | 6 |
| PEG 8000 (an example of hydrophilic additives) | 6 | 6 | 6 | | | | | | | | | |
| Other additives | q.s. | q.s. | q.s. | q.s. | q.s. | q.s. | q.s. | q.s. | q.s. | q.s. | q.s. | q.s. |

*Glyceryl monolinoleate may be replaced to, but not limited, C8 to C22 medium and/or long chain monoglycerides, medium and/or long chain diglycerides, or mixtures of medium and/or long chain monoglycerides and medium and/or long chain diglycerides.
**Peppermint oil may be replaced to, but not limited, peanut oil, safflower oil, sunflower oil, olive oil, castor oil, corn oil, maize oil, coconut oil, palm kernel oil, flax seed oil, wheat-germ oil, omega-3 oil, cottonseed oil, sesame oil, soybean oil, and the like.
***Oleic acid or stearic acid may be replaced to, but not limited, caprylic acid, capric acid, lauric acid, myristic acid, palmitic acid, and arachidic acid.

Example 3. Release Profiles of the Oral Dosage Forms Comprising Androst-4-en-17β-ol-3-one Ester The compositions and oral dosage forms of the present invention can be formulated such that they have distinctive release profiles. In one aspect, the % release of androst-4-en-17β-ol-3-one ester, (17-ß)-3-oxoandrost-4-en-17-yl tridecanoate, from dosage forms comprising androst-4-en-17β-ol-3-one ester can be tested in about 1000 mL of 2% w/v Triton X-100 in water maintained at about 37±1° C. using a USP-Type II dissolution apparatus set at 100 rpm.

Figure 2:
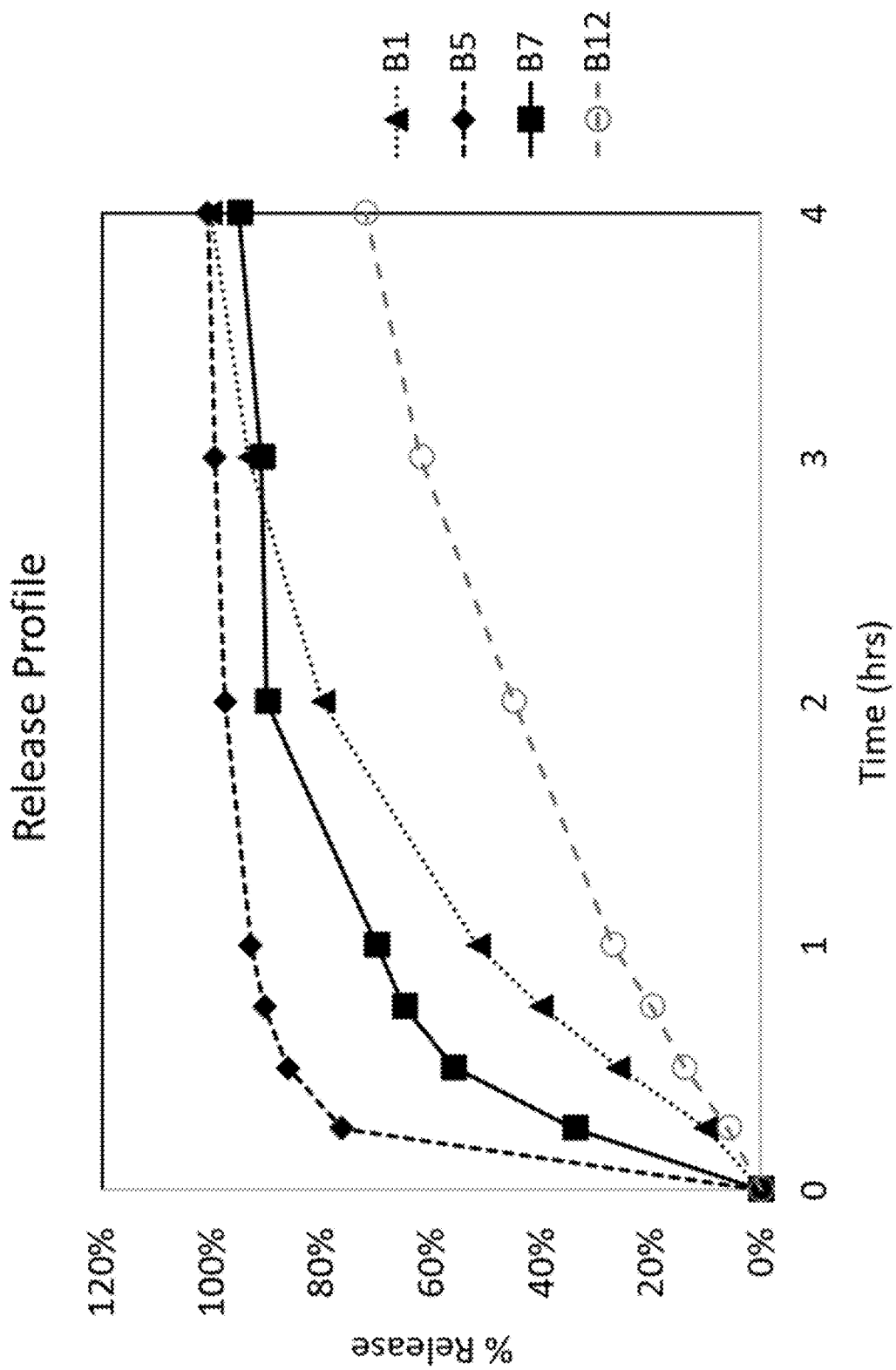
FIG. 2 is a graph of the % release profiles of the compositions comprising substantially noncrystalline forms of (17-ß)-3-oxoandrost-4-en-17-yl tridecanoate (the dosage forms B1, B5, and B7 shown in Table B) and substantially crystalline form of (17-ß)-3-oxoandrost-4-en-17-yl tridecanoate (the dosage form B12 shown in Table B) versus time (hours)

For example, FIG. 2 shows in vitro % release profiles of (17-ß)-3-oxoandrost-4-en-17-yl tridecanoate from the compositions comprising substantially noncrystalline forms (B1, B5, B7 shown in Table B) and substantially crystalline forms (B12 shown in Table B: the particle size of (17-ß)-3-oxoandrost-4-en-17-yl tridecanoate comprises more than 90% between 1 micron and 15 micron) measured using about 1000 mL of 2% w/v Triton X-100 in water maintained at about 37±1° C. taken in a USP-Type II dissolution apparatus set at 100 rpm. As shown in FIG. 2, the % release of (17-ß)-3-oxoandrost-4-en-17-yl tridecanoate from the dosage forms including noncrystalline (17-ß)-3-oxoandrost-4-en-17-yl tridecanoate forms (B1, B5, B7) is substantially different from the dosage form comprising substantially crystalline form of (17-ß)-3-oxoandrost-4-en-17-yl tridecanoate (B12). Therefore, in one embodiment, an oral dosage form comprising substantially noncrystalline (17-ß)-3-oxoandrost-4-en-17-yl tridecanoate forms can provide in vitro % release of at least about 75% of the (17-ß)-3-oxoandrost-4-en-17-yl tridecanoate during the first 120 minutes. In another embodiment, the oral dosage form comprising substantially noncrystalline (17-ß)-3-oxoandrost-4-en-17-yl tridecanoate forms can have an in vitro % release profile such that at least 45% of the (17-ß)-3-oxoandrost-4-en-17-yl tridecanoate is released within the first 1 hour, and in an additional embodiment, the oral dosage capsule comprising substantially noncrystalline (17-ß)-3-oxoandrost-4-en-17-yl tridecanoate forms can have an in vitro % release profile such that at least 90% of the (17-ß)-3-oxoandrost-4-en-17-yl tridecanoate is released within the 4 hours.

Example 4. PK Profiles of Select Dosage Forms

Figure 3:
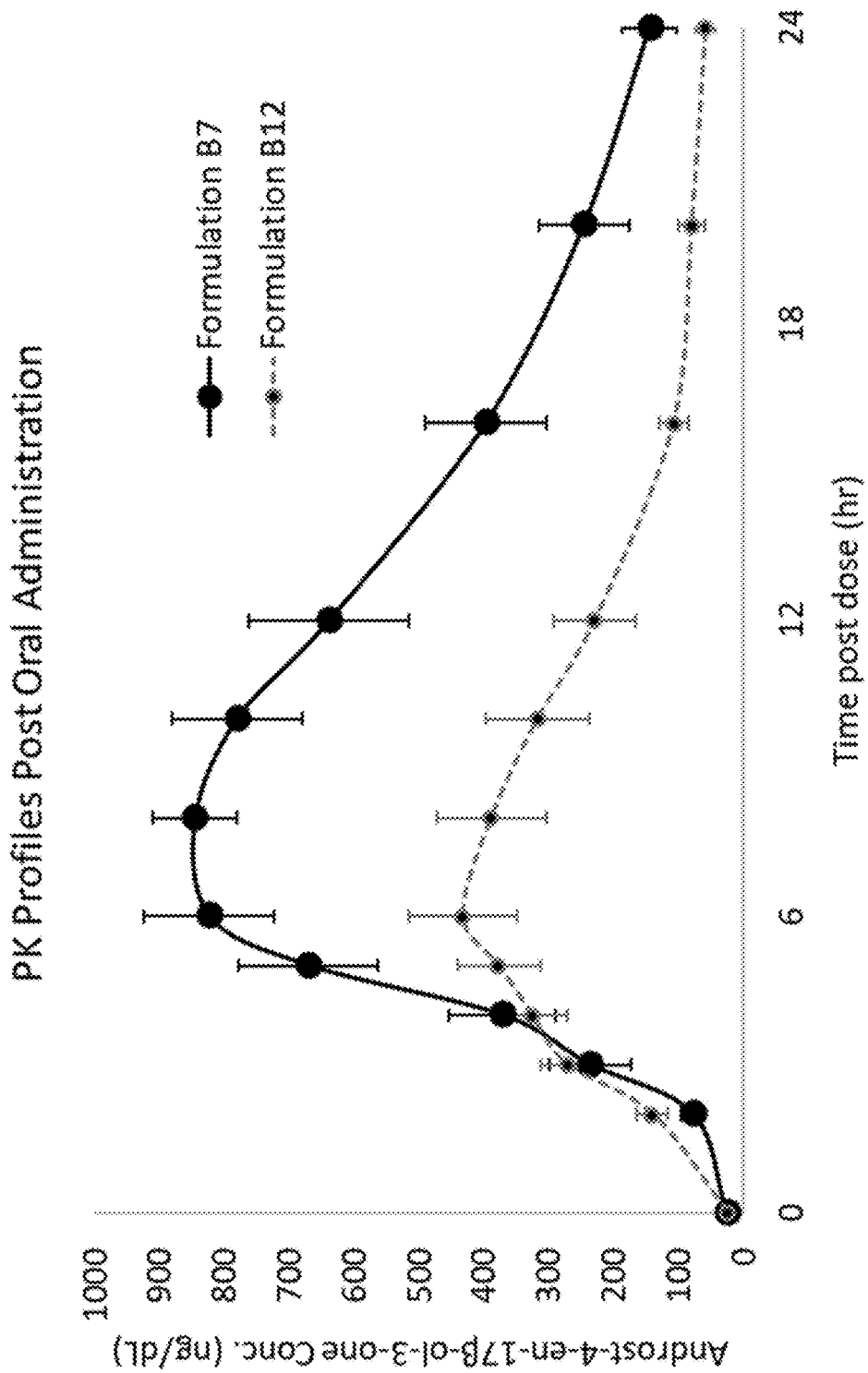
FIG. 3 shows PK profiles of androst-4-en-17β-ol-3-one from Treatment A (substantially noncrystalline form composition B7) and Treatment B (substantially crystalline form composition B12) for 24 hours post administration of study drugs to healthy postmenopausal women. Each symbol represents serum concentration of androst-4-en-17β-ol-3-one measured at time t ($C_t$) and upper/lower bars represent standard error.

A clinical study was performed to evaluate PK parameters of the oral dosage forms comprising (17-ß)-3-oxoandrost-4-en-17-yl tridecanoate in healthy postmenopausal women (N=10). The study was designed as an open-label, randomized, cross-over, single-dose, two-treatment, two-period study. The treatments were following as:
Treatment A: 550 mg of (17-ß)-3-oxoandrost-4-en-17-yl tridecanoate as androst-4-en-17β-ol-3-one ester in the dosage form B7 capsules
Treatment B: 550 mg of (17-ß)-3-oxoandrost-4-en-17-yl tridecanoate as androst-4-en-17β-ol-3-one ester in the dosage form B12 tablets
PK profiles of androst-4-en-17β-ol-3-one were obtained by measuring serum androst-4-en-17β-ol-3-one concentrations at time 0, 2, 3, 4, 5, 6, 8, 10, 12, 16, 20, and 24 hours post the single dose. FIG. 3 shows group mean PK profiles of androst-4-en-17β-ol-3-one concentrations obtained from Treatment A (dosage form B7) and B (dosage form B12) for 24 hours post administration of study drugs to subjects.

As seen in FIG. 3, the oral dosage form comprising substantially noncrystalline form of (17-ß)-3-oxoandrost-4-en-17-yl tridecanoate (dosage form B7 in Treatment A) provided higher bioavailability compared to one obtained from the oral dosage form comprising substantially crystalline form of (17-ß)-3-oxoandrost-4-en-17-yl tridecanoate (dosage form B12 in Treatment B).

Example 5. PK Parameters for a Select Dosage Form at Steady State

A multi-center, open-label, randomized, 4-treatment arm, multiple-dose study was performed to evaluate the safety, tolerability, and the steady-state PK parameters of the oral composition comprising substantially noncrystalline form of (17-ß)-3-oxoandrost-4-en-17-yl tridecanoate (dosage form B7) in hypogonadal males (N=48). The treatments were following as:
Treatment A: 500 mg of (17-ß)-3-oxoandrost-4-en-17-yl tridecanoate as androst-4-en-17β-ol-3-one ester in dosage form B7 in QD.
Treatment B: 750 mg of (17-ß)-3-oxoandrost-4-en-17-yl tridecanoate as androst-4-en-17β-ol-3-one ester in dosage form B7 in QD.
Treatment C: 1000 mg of (17-ß)-3-oxoandrost-4-en-17-yl tridecanoate as androst-4-en-17β-ol-3-one ester in dosage form B7 in QD.
Treatment D: 1250 mg of (17-ß)-3-oxoandrost-4-en-17-yl tridecanoate as androst-4-en-17β-ol-3-one ester in dosage form B7 in QD.

The steady state PK parameters were obtained post the treatment initiation. Table C shows the PK parameters of androst-4-en-17β-ol-3-one at steady state for each treatment.

TABLE C

Mean (±SD) serum PK parameters of androst-4-en-17β-ol-3-one at steady state

| Treatment | A | B | C | D |
|---|---|---|---|---|
| Dose of (17-β)-3-oxoandrost-4-en-17-yl tridecanoate | 500 mg QD | 750 mg QD | 1000 mg QD | 1250 mg QD |
| N | 12 | 11 | 12 | 12 |
| $C_{max}$, ng/dL | 608 (318) | 822 (254) | 930 (326) | 1233 (695) |
| $C_{avg}$, ng/dL | 307 (157) | 352 (41) | 405 (148) | 465 (201) |

The results shown in Table C displays that as the dose increased, $C_{avg}$ and $C_{max}$ increased. The evaluation of the relation between $C_{avg}$ or $C_{max}$ and dose amount of (17-ß)-3-oxoandrost-4-en-17-yl tridecanoate was performed using the group mean values of $C_{avg}$ and $C_{max}$ of androst-4-en-17β-ol-3-one obtained at the steady state. FIG. 4 displays A: the relations between $C_{avg}$ and dose, B: between $C_{max}$ and dose, and C: between $C_{max}$ and $C_{avg}$ and those relationships ($C_{avg}$ vs dose, $C_{max}$ vs dose, and $C_{max}$ vs $C_{avg}$) are linearly proportional.

Figure 4A:
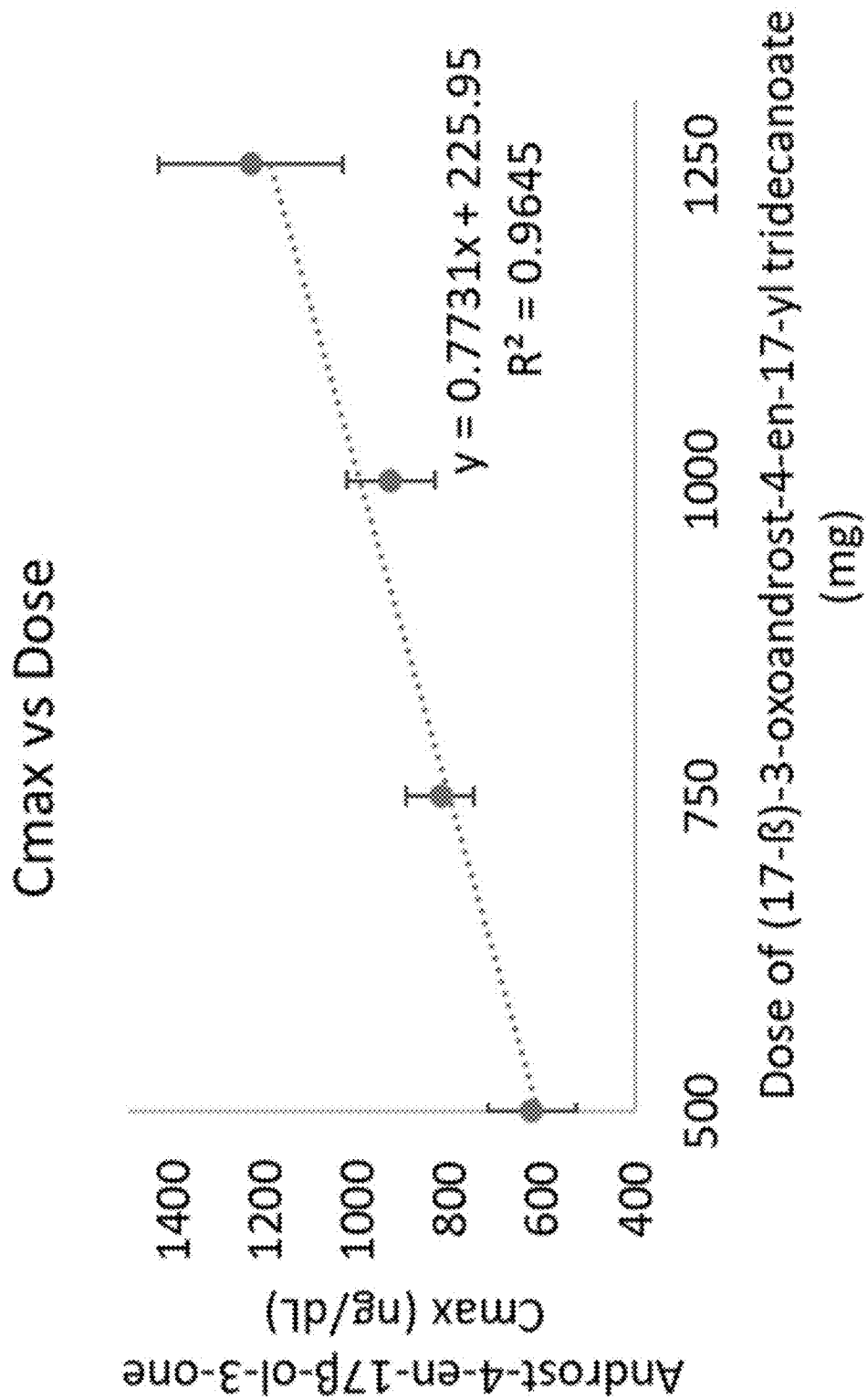
FIG. 4A shows the linear relationship between $C_{max}$ and dose of (17-ß)-3-oxoandrost-4-en-17-yl tridecanoate. The linear regression from 500 mg to 1250 mg of (17-ß)-3-oxoandrost-4-en-17-yl tridecanoate resulted in the correlation coefficient ($R^2$) close to 1: $R^2$=0.9645.
Figure 4B:
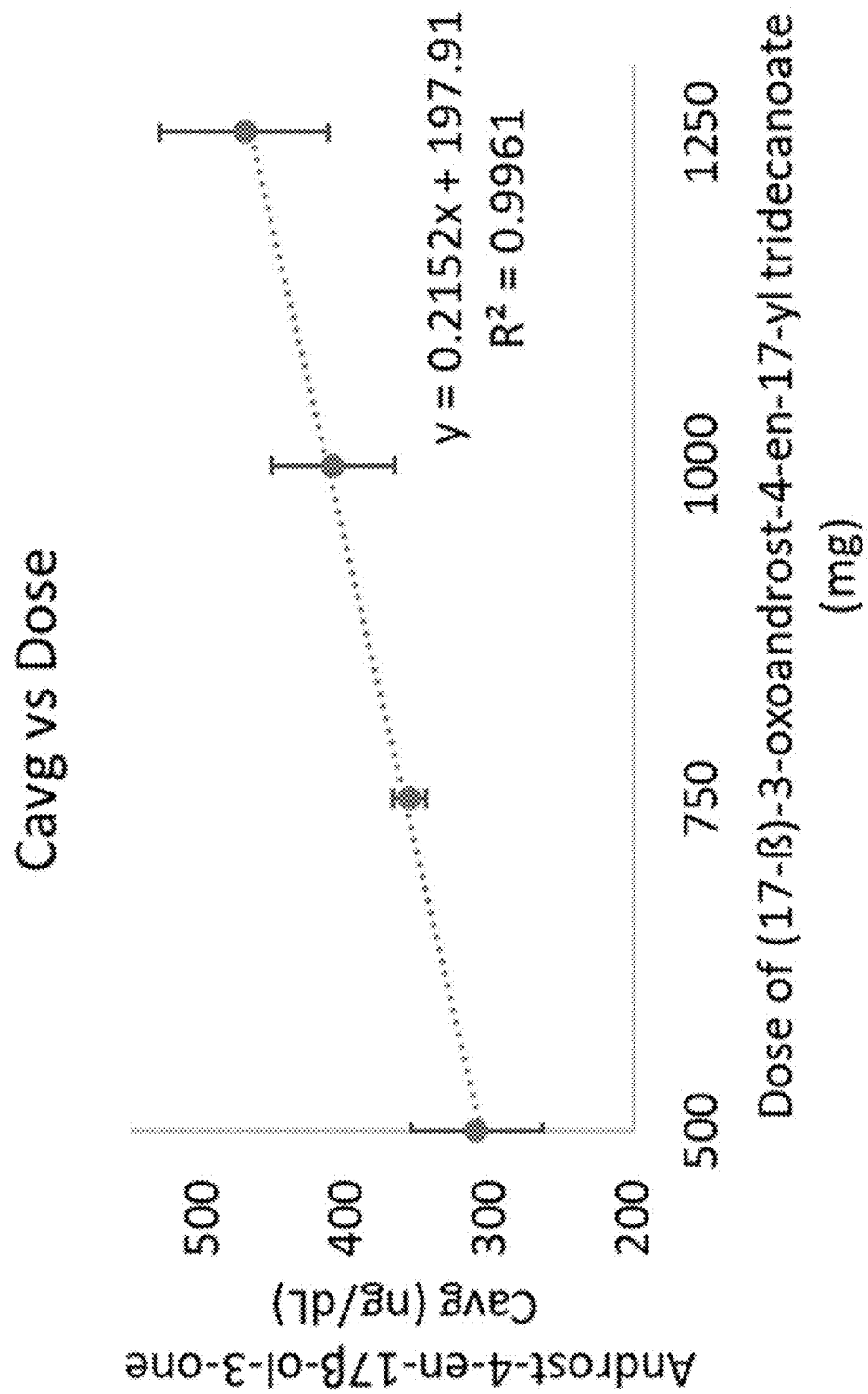
FIG. 4B shows the linear relationship between $C_{avg}$ and dose of (17-ß)-3-oxoandrost-4-en-17-yl tridecanoate. The linear regression from 500 mg to 1250 mg of (17-ß)-3-oxoandrost-4-en-17-yl tridecanoate resulted in the correlation coefficient ($R^2$) close to 1: $R^2$=0.9961.
Figure 4C:
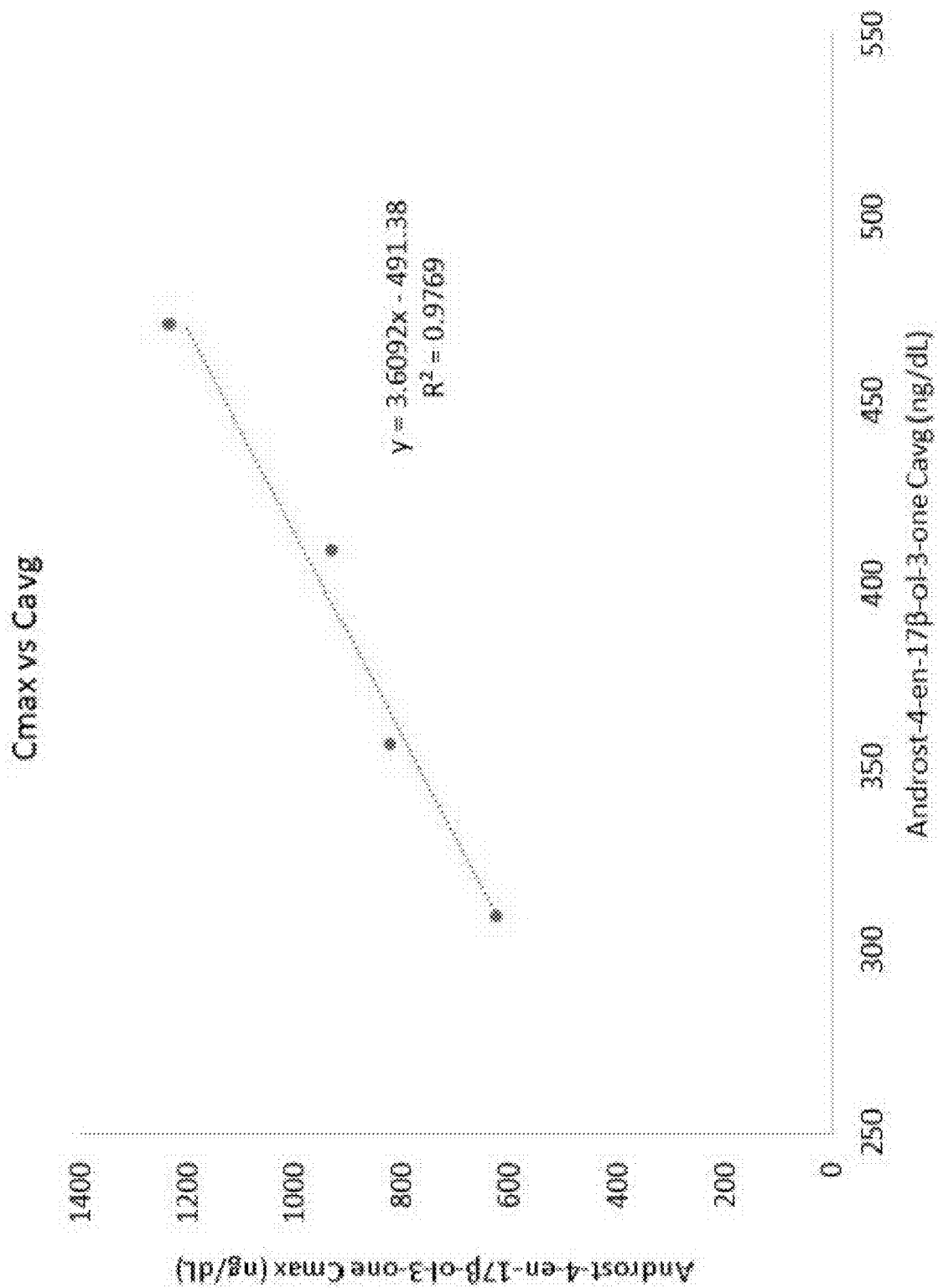
FIG. 4C shows the linear relationship between $C_{max}$ and $C_{avg}$ of androst-4-en-17β-ol-3-one obtained post administration of the noncrystalline form (17-ß)-3-oxoandrost-4-en-17-yl tridecanoate composition. The linear regression between $C_{max}$ and $C_{avg}$ of androst-4-en-17β-ol-3-one resulted in the correlation coefficient ($R^2$) close to 1: $R^2$=0.9769.
Figure 4D:
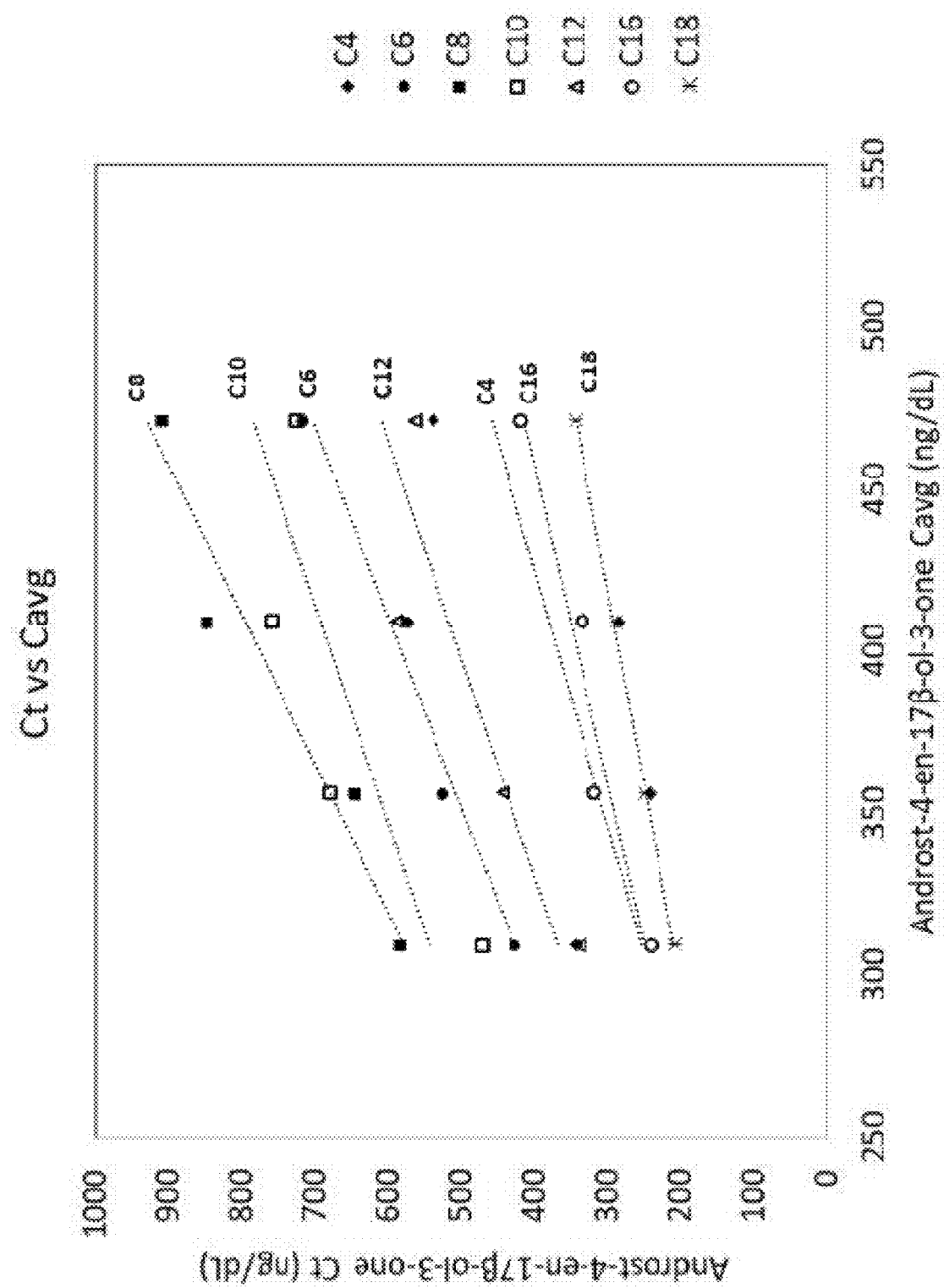
FIG. 4D shows the linear relationship between mean $C_t$ and $C_{avg}$ of androst-4-en-17β-ol-3-one obtained post administration of the substantially noncrystalline form (17-ß)-3-oxoandrost-4-en-17-yl tridecanoate composition. Mean $C_t$ at each time point is linearly proportional to mean $C_{avg}$.

In addition, the mean androst-4-en-17β-ol-3-one concentration at time "t" ($C_t$) was plotted against $C_{avg}$ in FIG. 4D. the relationship between mean $C_t$ and mean $C_{avg}$ in FIG. 4D also shows the linear proportion.

Example 6. PK Parameters of a Select Dosage Form at Steady State

A single-center, randomized, double-blind, placebo-controlled, ascending multiple-dose, serial-group study was conducted to evaluate the safety, tolerability, and the steady-state PK parameters of an oral composition comprising substantially noncrystalline form of (17-ß)-3-oxoandrost-4-en-17-yl undecanoate in adult hypogonadal male subjects (N=84). The treatments were following as:

Treatment A: 75 mg of (17-ß)-3-oxoandrost-4-en-17-yl undecanoate as androst-4-en-17β-ol-3-one ester based on dosage form B1 in BID.
Treatment B: 150 mg of (17-ß)-3-oxoandrost-4-en-17-yl undecanoate as androst-4-en-17β-ol-3-one ester based on dosage form B1 in BID.
Treatment C: 225 mg of (17-ß)-3-oxoandrost-4-en-17-yl undecanoate as androst-4-en-17β-ol-3-one ester based on dosage form B1 in BID.
Treatment D: 300 mg of (17-ß)-3-oxoandrost-4-en-17-yl undecanoate as androst-4-en-17β-ol-3-one ester based on dosage form B1 in BID.
Treatment E: placebo capsules in BID The steady state PK parameters were obtained post the treatment initiation. Table D shows the PK parameters of androst-4-en-17β-ol-3-one at steady state for each group.

TABLE D

Mean (±SD) serum PK parameters of androst-4-en-17β-ol-3-one at steady state

| Treatment | A | B | C | D |
|---|---|---|---|---|
| Dose of (17-β)-3-oxoandrost-4-en-17-yl undecanoate | 75 mg BID | 150 mg BID | 225 mg BID | 300 mg BID |
| N | 16 | 16 | 16 | 9 |
| $C_{max}$, ng/dL | 544 (169) | 792 (276) | 1169 (356) | 1644 (644) |
| $C_{avg}$, ng/dL | 270 (94) | 319 (77) | 446 (161) | 582 (184) |

The results shown in Table D display that as the dose increased, $C_{avg}$ and $C_{max}$ increased.

Example 7. Bioavailability Study of Androst-4-en-17β-ol-3-one Esters

A randomized, open-label, single-dose, 4-treatment, 4-period crossover study in eight healthy postmenopausal female subjects was conducted to evaluate PK parameters of androst-4-en-17β-ol-3-one from four different androst-4-en-17β-ol-3-one esters (i.e., (17-ß)-3-oxoandrost-4-en-17-yl undecanoate, (17-ß)-3-oxoandrost-4-en-17-yl dodecanoate, (17-ß)-3-oxoandrost-4-en-17-yl tridecanoate, and (17-ß)-3-oxoandrost-4-en-17-yl tetradecanoate). Bioavailability ratio of each androst-4-en-17β-ol-3-one ester was obtained compared to the PK parameters of androst-4-en-17β-ol-3-one post single dose administration of (17-ß)-3-oxoandrost-4-en-17-yl undecanoate.

The four treatments were following as:
Treatment A: 75.2 mg of (17-ß)-3-oxoandrost-4-en-17-yl undecanoate as 47.5 mg of androst-4-en-17β-ol-3-one equivalent amount in dosage form B1
Treatment B: 77.5 mg of (17-ß)-3-oxoandrost-4-en-17-yl dodecanoate as 47.5 mg of androst-4-en-17β-ol-3-one equivalent amount in dosage form B1
Treatment C: 79.8 mg of (17-ß)-3-oxoandrost-4-en-17-yl tridecanoate as 47.5 mg of androst-4-en-17β-ol-3-one equivalent amount in dosage form B1
Treatment D: 82.1 mg of (17-ß)-3-oxoandrost-4-en-17-yl tetradecanoate as 47.5 mg of androst-4-en-17β-ol-3-one equivalent amount in dosage form B1

Table E displays bioavailability ratio results for androst-4-en-17β-ol-3-one esters in comparison to (17-ß)-3-oxoandrost-4-en-17-yl undecanoate, along with the molecular weight conversion ratio (CR) of androst-4-en-17β-ol-3-one ester to androst-4-en-17β-ol-3-one. The bioavailability ratio was calculated by dividing AUC0-24 of androst-4-en-17β-ol-3-one obtained from each androst-4-en-17β-ol-3-one ester by AUC0-24 of androst-4-en-17β-ol-3-one obtained from (17-ß)-3-oxoandrost-4-en-17-yl undecanoate.

TABLE E

Bioavailability ratio of androst-4-en-17β-ol-3-one post single dose of androst-4-en-17β-ol-3-one esters

| Treatment | Molecular Weight Conversion Ratio to androst-4-en-17β-ol-3-one | Bioavailability Ratio to A* |
|---|---|---|
| A | 1.58 | 1.00 |
| B | 1.63 | 0.75 |
| C | 1.68 | 0.58 |

*Bioavailability ratio of the treatment was calculated using $AUC_{0-24}$ of androst-4-en-17β-ol-3-one observed from each treatment relative $AUC_{0-24}$ of androst-4-en-17β-ol-3-one observed from the treatment A.

The study results show that as the fatty acid chain length in the ester increases, the oral bioavailability decreases. Bioavailability of androst-4-en-17β-ol-3-one obtained from individual androst-4-en-17β-ol-3-one esters compared to androst-4-en-17β-ol-3-one obtained from (17-ß)-3-oxoandrost-4-en-17-yl undecanoate resulted in about 75% for (17-ß)-3-oxoandrost-4-en-17-yl dodecanoate and about 58% for (17-ß)-3-oxoandrost-4-en-17-yl tridecanoate. These results are applied to simulate the PK parameters and PK performance of the compositions comprising a combination of (17-ß)-3-oxoandrost-4-en-17-yl undecanoate, (17-ß)-3-oxoandrost-4-en-17-yl dodecanoate, and/or (17-ß)-3-oxoandrost-4-en-17-yl tridecanoate.

Example 8. Estimated PK Parameters of Select Dosage Forms Comprising a Combination of (17-ß)-3-oxoandrost-4-en-17-yl Tridecanoate and (17-ß)-3-oxoandrost-4-en-17-yl Undecanoate from Simulation Using Clinical Study Results The PK parameters obtained from the clinical studies with multiple doses of (17-ß)-3-oxoandrost-4-en-17-yl tridecanoate (Example 5), (17-ß)-3-oxoandrost-4-en-17-yl undecanoate (Example 6), and bioavailability results of androst-4-en-17β-ol-3-one esters compared to (17-ß)-3-oxoandrost-4-en-17-yl tridecanoate (Example 7) were utilized for simulation to obtain the estimated PK parameters for an oral composition comprising a combination of (17-ß)-3-oxoandrost-4-en-17-yl tridecanoate, (17-ß)-3-oxoandrost-4-en-17-yl undecanoate, and/or (17-ß)-3-oxoandrost-4-en-17-yl dodecanoate. Table F displays some examples of the estimated PK parameters obtained from simulation using PK data from the clinical studies described herein (Example 5, 6, and 7).

TABLE F

Estimated serum mean PK parameters of androst-4-en-17β-ol-3-one in dosage forms comprising a combination of (17-β)-3-oxoandrost-4-en-17-yl undecanoate and (17-β)-3-oxoandrost-4-en-17-yl tridecanoate

| Dosage Form | BB7 | BB8 | BB9 |
|---|---|---|---|
| Daily Dose* of androst-4-en-17β-ol-3-one ester as androst-4-en-17β-ol-3-one equivalent amount, mg | 294 | 330 | 384 |
| ✓ (17-β)-3-oxoandrost-4-en-17-yl undecanoate amount per unit, mg | 56 | 84 | 56 |
| ✓ (17-β)-3-oxoandrost-4-en-17-yl tridecanoate amount per unit, mg | 188 | 188 | 263 |

TABLE F-continued

Estimated serum mean PK parameters of androst-4-en-17β-ol-3-one in dosage forms comprising a combination of (17-β)-3-oxoandrost-4-en-17-yl undecanoate and (17-β)-3-oxoandrost-4-en-17-yl tridecanoate

| Dosage Form | BB7 | BB8 | BB9 |
|---|---|---|---|
| Cmax (ng/dL) | 530 | 673 | 626 |
| Cavg (ng/dL) | 280 | 335 | 347 |

*Daily dose was administered as two unit dosages.

Example 9: Effect of Dosage Forms on PK Performance

Simulations of clinical performance estimated from PK parameters with the select present dosage forms (shown in Table B) comprising substantially noncrystalline and crystalline forms of androst-4-en-17β-ol-3-one ester were carried out.

Table G below shows group PK performance results at various initial doses with an exemplary titration amount, and an exemplary titration metric post two dose adjustments/titrations. For the examples shown in Table G, the androst-4-en-17β-ol-3-one ester was (17-ß)-3-oxoandrost-4-en-17-yl tridecanoate.

TABLE G

Estimated PK performance of oral compositions comprising substantially crystalline or noncrystalline forms of androst-4-en-17β-ol-3-one ester

| Dosage form | B4 | B3 | B6 | B5 | B8 | B7 | B10 | B9 | B12 | B11 |
|---|---|---|---|---|---|---|---|---|---|---|
| Initial dose as androst-4-en-17β-ol-3-one equivalent amount | 298 mg | | 446 mg | | 595 mg | | 744 mg | | 893 mg | |
| Titration metric | Up if $C_{10}$ < 400 ng/dL, maintain if 400 ng/dL ≤ $C_{10}$ ≤ 1050 ng/dL, or down if $C_{10}$ > 1050 ng/dL | | | | | | | | | |
| Titration amount as androst-4-en-17β-ol-3-one equivalent amount | ±149 mg | | | | | | | | | |
| PK Performance target after two titrations***: % of subjects | | | | | | | | | | |
| >75% within the predetermined range* | No | Yes | No | Yes | No | Yes | No | Yes | No | Yes |
| <3% in $C_{max}$ > 2.5 × uln** | Yes | Yes | Yes | Yes | Yes | Yes | Yes | Yes | Yes | Yes |

*% of subjects within the predetermined range obtained based on the predetermined serum androst-4-en-17β-ol-3-one range in the $C_{10}$ titration metric is considered as the estimated $C_{avg}$ responder within the normal range.
**ULN: Upper limit of normal range for serum androst-4-en-17β-ol-3-one concentration.
***Titration(s) are performed, if needed, in a subject based on the predetermined levels/range.

As shown in Table G, the dosage forms comprising substantially crystalline (mean particle size >1 micron) forms of androst-4-en-17β-ol-3-one ester (B4, B6, B8, B10, B12) with the initial dose range as androst-4-en-17β-ol-3-one equivalent amount did not achieve the desired PK performance target, typically required for regulatory approval, based on the estimated PK performance by simulation. While the exemplary dosage forms comprising substantially noncrystalline forms of androst-4-en-17β-ol-3-one ester (B3, B5, B7, B9, B11) with those initial dose of androst-4-en-17β-ol-3-one equivalent amount from 298 mg to 893 mg achieved the PK performance target, based on the estimated PK performance by simulation.

This example is obtained from an exemplary simulation, and the estimated PK performance post titration(s) is not limited on this specific example.

Example 10: Effect of Initial Dose and Titration Amount on PK Performance

Simulations of clinical performance from estimated PK parameters with oral dosage forms comprising substantially noncrystalline form of androst-4-en-17β-ol-3-one ester (e.g., dosage form B7) were performed at various initial doses.

Table H below shows estimated group PK performance results at various initial doses with an exemplary titration amount and exemplary titration metric post two dose adjustments/titrations. The androst-4-en-17β-ol-3-one ester for the examples shown in Table H was (17-ß)-3-oxoandrost-4-en-17-yl tridecanoate. The utilized exemplary titration metric with the titration amount (±149 mg) as androst-4-en-17β-ol-3-one equivalent amount was following as:

Maintain the dose of androst-4-en-17β-ol-3-one ester if 250 ng/dL≤T $C_{12}$≤850 ng/dL,
up-titrate by 149 mg of androst-4-en-17β-ol-3-one equivalent amount for androst-4-en-17β-ol-3-one ester if T $C_{12}$<250 ng/dL, or
down-titrate by 149 mg of androst-4-en-17β-ol-3-one equivalent amount for androst-4-en-17β-ol-3-one ester if T $C_{12}$>850 ng/dL.

TABLE H

Estimated PK performance of oral compositions with a variety of initial doses

| Dosing Regimen | | 3A1 | 3A2 | 3A3 | 3A4 | 3A5 | 3A6 | 3A7 | 3A8 | 3A9 |
|---|---|---|---|---|---|---|---|---|---|---|
| Initial dose as androst-4-en-17β-ol-3-one equivalent amount | | 149 mg | 236 mg | 253 mg | 298 mg | 446 mg | 595 mg | 744 mg | 893 mg† | 1050 mg† |
| % of Subjects after Two Titrations*** | ≥75% within the predetermined range* | No | Yes | Yes | Yes | Yes | Yes | Yes | Yes | Yes |
| | <3% in $C_{max}$ > 2.5 × ULN** | Yes | Yes | Yes | Yes | Yes | Yes | Yes | Yes | No |

*% of subjects within the predetermined range obtained based on the predetermined serum androst-4-en-17β-ol-3-one range in the $C_{12}$ titration metric is considered as the estimated $C_{avg}$ responder within the normal range.
**ULN: Upper limit of normal range for serum androst-4-en-17β-ol-3-one concentration.
***Titration(s) are performed, if needed, in a subject based on the predetermined levels/range.
†For the initial dose greater than or equal to 893 mg, the titration amount was applied with 179 mg.

As shown in Table H, oral compositions and method of dosing regimen from 3A2 to 3A8 comprising the initial dose of androst-4-en-17β-ol-3-one equivalent amount in about 236 mg to about 893 mg are estimated to achieve both $C_{avg}$ PK performance target (i.e., ≥75% of subjects in the group with $C_{avg}$ within normal range) and $C_{max}$ PK performance target (i.e. <3% of subjects with $C_{max}$>2.5×ULN) post two titrations.

Figure 5:
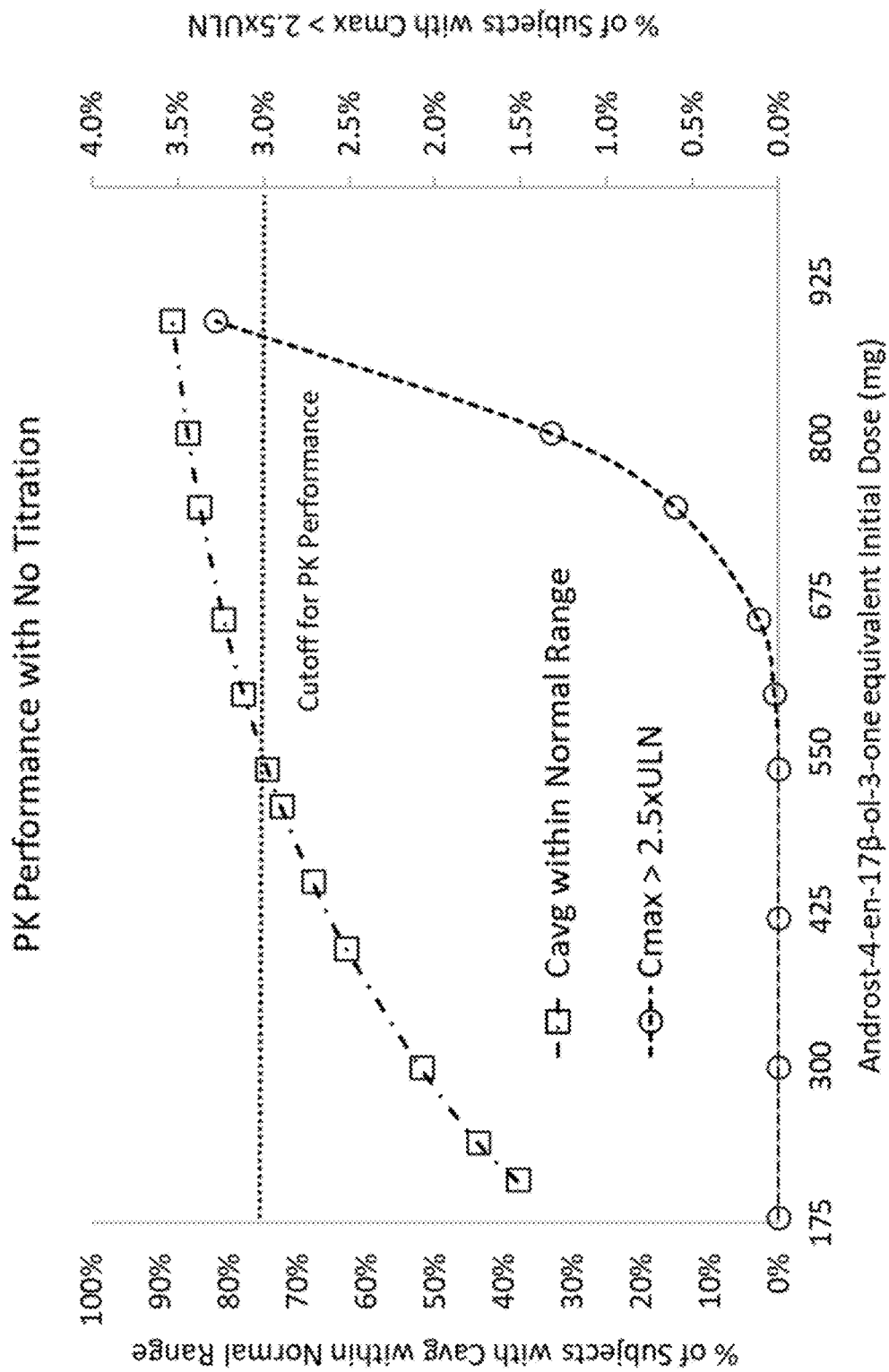
FIG. 5 shows the plots of % of subjects achieving the $C_{avg}$ and $C_{max}$ target criteria vs. the initial dose of an androst-4-en-17β-ol-3-one equivalent amount based on simulated PK results with no titration.

FIG. 5 shows the plots of % of subjects achieving the $C_{avg}$ and $C_{max}$ target criteria vs. the initial dose of androst-4-en-17β-ol-3-one equivalent amount (in this example, for (17-ß)-3-oxoandrost-4-en-17-yl tridecanoate) based on simulated PK results with no titration. As shown in FIG. 5, the initial doses greater than or equal to about 536 mg and less than or equal to about 893 mg of androst-4-en-17β-ol-3-one equivalent amount (that is, in case of (17-ß)-3-oxoandrost-4-en-17-yl tridecanoate, 900 mg and 1,500 mg) with no titration met both $C_{avg}$ and $C_{max}$ performance targets. This implies a high dose (at least about 536 mg of androst-4-en-17β-ol-3-one equivalent amount for (17-ß)-3-oxoandrost-4-en-17-yl tridecanoate) is required at the initiation of treatment to meet the PK performance if the treatment method comprises no titration. The initiation of therapy with the high dose of androst-4-en-17β-ol-3-one equivalent amount for (17-ß)-3-oxoandrost-4-en-17-yl tridecanoate in the compositions may have potential to have adverse effects in super-absorbers of androst-4-en-17β-ol-3-one ester. However, the simulated PK performance post two titrations displayed in Table H shows the initial dose ranging from about 240 mg to about 895 mg in androst-4-en-17β-ol-3-one equivalent amount for (17-ß)-3-oxoandrost-4-en-17-yl tridecanoate can be effective on both $C_{avg}$ and $C_{max}$ PK performance. The extension to lower initial doses with dose titration(s) against the required higher dose in no titration can reduce the super-absorber's potential adverse event risk. These results conclude the titration methods can be more effective and safer, compared to the methods with no titration, in that the androst-4-en-17β-ol-3-one equivalent dose can be initiated with as low as at least about 236 mg.

Simulations of clinical performance from estimated PK parameters with oral compositions comprising substantially noncrystalline forms (dosage form B7 comprising (17-ß)-3-oxoandrost-4-en-17-yl tridecanoate) of androst-4-en-17β-ol-3-one ester were performed at various titration amounts with various initial doses.

Table I below shows group PK performance results at various titration amounts with various exemplary initial doses of (17-ß)-3-oxoandrost-4-en-17-yl tridecanoate as androst-4-en-17β-ol-3-one equivalent amount, upon an exemplary titration metric (e.g. up-titrate the dose if $C_{18}$<160 ng/dL, maintain the dose if 160 ng/dL≤$C_{18}$≤350 ng/dL, or down-titrate the dose if $C_{18}$>350 ng/dL) post two dose adjustments/titrations. The PK performance was estimated based on the exemplary titration metric using serum androst-4-en-17β-ol-3-one concentration from blood samples obtained at time "t" post administration (e.g., in this case, $C_{18}$).

TABLE I

Estimated PK performance of oral compositions with a variety of titration amounts and initial doses

| Dosing Regimen | | 3B1 | 3B2 | 3B3 | 3B4 | 3B5 | 3B6 | 3B7 | 3B8 | 3B9 | 3B10 | 3B11 | 3B12 | 3B13 | 3B14 |
|---|---|---|---|---|---|---|---|---|---|---|---|---|---|---|---|
| Initial dose as androst-4-en-17β-ol-3-one equivalent amount | | 253 mg | 253 mg | 253 mg | 298 mg | 298 mg | 298 mg | 357 mg | 417 mg | 417 mg | 506 mg | 595 mg | 744 mg | 893 mg | 1050 mg |
| Titration amount of as androst-4-en-17β-ol-3-one equivalent amount | | ±48 mg | ±83 mg | ±127 mg | ±51 mg | ±149 mg | ±268 mg | ±119 mg | ±139 mg | ±149 mg | ±253 mg | ±179 mg | ±149 mg | ±179 mg | ±179 mg |
| % of Subjects after Two Titrations*** | >75% within the predetermined range* | No | Yes | Yes | No | Yes | Yes | Yes | Yes | Yes | Yes | Yes | Yes | Yes | Yes |
| | <3% in $C_{max}$ > 2.5 × ULN** | Yes | Yes | Yes | Yes | Yes | Yes | Yes | Yes | Yes | Yes | Yes | Yes | Yes | No |

*% of subjects within the predetermined range obtained based on the predetermined serum androst-4-en-17β-ol-3-one range in the $C_{18}$ titration metric is considered as the estimated $C_{avg}$ responder within the normal range.
**ULN: Upper limit of normal range for serum androst-4-en-17β-ol-3-one concentration.
***Titration(s) are performed, if needed, in a subject based on the predetermined levels/range.

As shown in Table I, the dosing regimens of 3B1-3B6 with lower initial doses as androst-4-en-17β-ol-3-one equivalent amount of 253 mg and 298 mg were compared for PK performance according to different titration amounts. For the androst-4-en-1703-ol-3-one equivalent initial dose of 253 mg (3B1-3B3), the titration amount with less than 20% of the initial dose (3B1) did not meet the PK performance target, while greater than 20% (3B2: about 33% and 3B3: 50%) met the PK performance target. Similarly, 3B4 with titration amount less than 20% of the androst-4-en-17β-ol-3-one equivalent initial dose (17% of 298 mg) failed to achieve the PK performance target, while 3B5 and 3B6 (50% and 90% of the androst-4-en-17β-ol-3-one equivalent initial dose, respectively) met the PK performance target. For the $C_{max}$ target in PK performance target, the highest androst-4-en-17β-ol-3-one equivalent initial dose (3B14: 1050 mg with the titration amount of 17% of the initial dose) failed due to having greater than 3% of subjects with $C_{max}$>2.5×ULN. In conclusion, the post-titration PK performance is significantly dependent upon the titration amount with the initial dose. Table I concludes that the titration amount range of at least 20% of the initial dose can provide the effectiveness of androst-4-en-17β-ol-3-one therapy within the androst-4-en-17β-ol-3-one equivalent initial dose of about 250 mg to about 895 mg in hypogonadal subjects.

Example 11. Effect of Number of Titrations and Titration Metric on PK Performance Upon titration simulations using the observed PK profile results obtained from clinical studies (Examples 4, 5, 6, and 7) from the dosage form comprising substantially noncrystalline forms of androst-4-en-17β-ol-3-one ester, the present oral dosage forms and methods with dose titration(s), if needed, improve response to the therapy in group of subjects/patients in need of such therapy compared to the methods without dose titration.

PK parameters with no titration were obtained from the clinical studies (Example 4, 5, 6, and 7), and the post-titration PK performance was estimated from titration simulation and assessed with regard to the target PK criteria in a group of hypogonadal men using an appropriate dose titration metrics.

The no-titration PK performance data for the dosage form B7 comprising (17-ß)-3-oxoandrost-4-en-17-yl tridecanoate from the clinical study shown in Example 5 is displayed in Table J below.

TABLE J

PK performance results with no titration from a clinical study (Example 5)

| Dose as androst-4-en-17β-ol-3-one equivalent amount | Target group response criteria (PK performance target) | Dosage form B7 with (17-β)-3-oxoandrost-4-en-17-yl tridecanoate % of responders |
|---|---|---|
| SD1 = 298 mg | $C_{avg}$ within normal range* | 36% |
| | $C_{max}$ > 2.5 × ULN** | 0% |
| SD2 = 446 mg | $C_{avg}$ within normal range | 91% |
| | $C_{max}$ > 2.5 × ULN | 0% |
| SD3 = 595 mg | $C_{avg}$ within normal range | 75% |
| | $C_{max}$ > 2.5 × ULN | 0% |
| SD4 = 744 mg | $C_{avg}$ within normal range | 92% |
| | $C_{max}$ > 2.5 × ULN | 8.0% |

*Normal range depends on the analytical lab, assay method, and/or blood collecting tube types. In this study, $C_{avg}$ responders were obtained based on the predetermined serum androst-4-en-17β-ol-3-one Cavg range between 300 ng/dL and 1140 ng/dL.
**ULN: Upper limit of normal range for serum androst-4-en-17β-ol-3-one concentration. However, the 2.5 × ULN in this study was 2,500 ng/dL regardless of the normal Cavg range.

In addition, the estimated PK performance data from titration simulation results are shown in Table K below as a function of initial dose after each titration (e.g., 0, 1, and 2 titrations) post start of the therapy.

In an example, a titration simulation using $C_{avg}$ and $C_{max}$ was performed based on normal distribution with an individual variability ranging from about 10% to 60% (average 35%) from the observed PK parameters, such as mean androst-4-en-17β-ol-3-one $C_{avg}$ and $C_{max}$ from clinical studies (Examples 5, 6, and 7). In another example, a titration simulation using $C_t$ was performed using the titration metric with the predetermined $C_t$ range obtained from the relationship between mean $C_t$ and mean $C_{avg}$, and clinical $C_t$ data from monotherapy of (17-ß)-3-oxoandrost-4-en-17-yl tridecanoate or simulated $C_t$ data for oral dosage forms comprising a combination of androst-4-en-17β-ol-3-one esters (e.g., (17-ß)-3-oxoandrost-4-en-17-yl undecanoate, (17-ß)-3-oxoandrost-4-en-17-yl dodecanoate, and (17-ß)-3-oxoandrost-4-en-17-yl tridecanoate) based on the bioavailability ratio shown in Example 7.

The following exemplary titration metric for the post-titration PK performance simulation was employed based on single point sampling at 6 hours post dose ($C_6$):
a) maintain the dose of androst-4-en-17β-ol-3-one equivalent amount for (17-ß)-3-oxoandrost-4-en-17-yl tridecanoate if androst-4-en-17β-ol-3-one $C_6$ is between 300 ng/dL and 800 ng/dL,
b) up titrate by 149 mg of androst-4-en-17β-ol-3-one equivalent amount for (17-ß)-3-oxoandrost-4-en-17-yl tridecanoate if androst-4-en-17β-ol-3-one $C_6$ is less than 300 ng/dL, or
c) down-titrate by 149 mg of androst-4-en-17β-ol-3-one equivalent amount for (17-ß)-3-oxoandrost-4-en-17-yl tridecanoate if androst-4-en-17β-ol-3-one $C_6$ greater than 800 ng/dL.

TABLE K

Estimated group PK performance following a number of titrations for the oral dosage form B7 with a variety of initial doses in the monotherapy of (17-β)-3-oxoandrost-4-en-17-yl tridecanoate

| Staring dose as androst-4-en-17β-ol-3-one equivalent amount | Target group response criteria | No titration % of responders | Post one titration*** % of responders | Post two titrations*** % of responders |
|---|---|---|---|---|
| SD1 = 298 mg | Within the predetermined range* | 58.3% | 82.6% | 92.7% |
| | $C_{max}$ > 2.5 × ULN** | <3.0% | <3.0% | <3.0% |
| SD2 = 446 mg | Within the predetermined range | 72.7% | 88.6% | 96.9% |
| | $C_{max}$ > 2.5 × ULN | <3.0% | <3.0% | <3.0% |
| SD3 = 595 mg | Within the predetermined range | 58.3% | 85.0% | 93.8% |
| | $C_{max}$ > 2.5 × ULN | <3.0% | <3.0% | <3.0% |
| SD4 = 744 mg | Within the predetermined range | 58.3% | 82.6% | 92.8% |
| | $C_{max}$ > 2.5 × ULN | >3.0% | <3.0% | <3.0% |

*Responder within the predetermined Ct range obtained based on the predetermined serum androst-4-en-17β-ol-3-one range in the $C_6$ titration metric is considered as the estimated $C_{avg}$ responder within the normal range.
**ULN: Upper limit of normal range for serum androst-4-en-17β-ol-3-one concentration.
***Titration(s) are performed, if needed, in a subject based on the predetermined levels/range.

For the exemplary dosage form B7 and method with the exemplary titration metric as shown in Table K, at variety of initial doses groups with each additional dose titration had shown improvement of PK performance relative to ones from group with no dose titration. Therefore, a titration method described in this disclosure provides a more effective option for a super or poor absorbing hypogonadal patient who may be not eligible for continuing therapy due to erroneous discontinuation of the therapy.

For practical reasons in clinical use a single blood sampling post single dose administration at steady state is likely to be utilized to assess therapy performance and decision on dose titration, as needed.

Consistent with the dosage form B7 and method of this invention, group PK performance results against desired targets based on simulations post two titrations using predetermined $C_t$ levels/ranges are presented in Table L, along with an exemplary initial dose and a titration amount. In this example, androst-4-en-17β-ol-3-one was (17-ß)-3-oxoandrost-4-en-17-yl tridecanoate. Based on the relationship between mean $C_t$ and $C_{avg}$, the titration metrics with the predetermined levels of $C_t$ at different time points have been developed to simulate PK performance with a variety of initial doses and the titration dose amount.

Simulation was performed utilizing various androst-4-en-17β-ol-3-one $C_t$ titration metrics and associated criteria/limits with the PK data obtained from the clinical study previously described.

Table L displays the results of an exemplary simulation, and the PK performance post titration(s) is not limited on this specific example.

TABLE L

Estimated PK performance following titration metrics based on androst-4-en-17β-ol-3-one $C_t$

| | Dosage form B7 with (17-β)-3-oxoandrost-4-en-17-yl tridecanoate | | | | |
|---|---|---|---|---|---|
| Initial dose as androst-4-en-17β-ol-3-one equivalent amount | 446 mg | | | | |
| Titration amount as androst-4-en-17β-ol-3-one equivalent amount | ±149 mg | | | | |
| Titration metric based on $C_t$ | Up if C4 < 300 ng/dL Maintain if 300 ng/dL ≤ C4 ≤ 650 ng/dL Down if C4 > 650 ng/dL | Up if C6 < 300 ng/dL Maintain if 300 ng/dL ≤ C6 ≤ 800 ng/dL Down if C6 > 800 ng/dL | Up if C12 < 500 ng/dL Maintain if 500 ng/dL ≤ C12 ≤ 800 ng/dL Down if C12 > 800 ng/dL | Up if C12 < 250 ng/dL Maintain if 250 ng/dL ≤ C12 ≤ 850 ng/dL Down if C12 > 850 ng/dL | Up if C18 < 160 ng/dL Maintain if 160 ng/dL ≤ C18 ≤ 350 ng/dL Down if C18 > 350 ng/dL |
| PK Performance after two titrations***: % of subjects | | | | | |
| >75% within the predetermined $C_t$ range* | No | Yes | Yes | Yes | Yes |
| <3% in $C_{max}$ > 2.5 × ULN** | Yes | Yes | Yes | Yes | Yes |

*Responder within the predetermined $C_t$ range is considered as the estimated $C_{avg}$ responder within the normal range.
**ULN: Upper limit of normal range for serum androst-4-en-17β-ol-3-one concentration.
***Titration(s) are performed, if needed, in a subject based on the predetermined levels/range.

As shown in Table L, the appropriate titration metrics with a variety of $C_t$ with different predetermined ranges can determine the therapeutic effectiveness (i.e., PK performance) with administration of the current oral dosage forms comprising substantially noncrystalline androst-4-en-17β-ol-3-one ester forms (in this case, dosage form B7). Therefore, determination of titration metrics is critical to provide the PK performance for subjects in need of the therapy.

It is understood that the above-described various types of compositions, dosage forms, methods and/or modes of applications are only illustrative of various invention embodiments. Numerous modifications and alternative arrangements may be devised by those skilled in the art without departing from the spirit and scope of the present disclosure and the appended claims are intended to cover such modifications and arrangements. Thus, while invention embodiments have been described above with particularity and detail, it will be apparent to those of ordinary skill in the art that variations including, but not limited to, variations in size, materials, shape, form, function and manner of operation, assembly and use may be made without departing from the principles and concepts set forth herein.

What is claimed is:

1. A method of administering a treatment regimen for at least one condition associated with at least one of fatigue, a reduction in muscle size, a reduction in muscle strength, a reduction in body muscle mass, a reduction in muscle tone, a reduction in bone density, a reduction in body mass index (BMI), a reduction in energy, a reduction in motivation, a reduction in endurance, decreased libido, diminished memory, anemia, marrow failure, renal failure, chronic respiratory failure, cardiac failure, a steroid-dependent autoimmune disease, muscle wasting, attacks of hereditary angioedema, attacks of hereditary urticaria; andropause, palliating terminal breast cancer, anorexia nervosa, hyperthyroidism, hypogonadism, androgen insensitivity, androgen deficiency, alcoholic hepatic cirrhosis, primary biliary cirrhosis, insulin resistance, fatty liver, hypertension, obesity, sarcopenia, frailty, and dyslipidemia, said method comprising:
administering to a subject an initial dosage comprising at least one dose of a pharmaceutical composition comprising a non-undecanoate testosterone ester,
obtaining a steady state androst-4-en-17β-ol-3-one serum concentration level of said subject, and
administering to said subject at least one maintenance dosage comprising at least one dose of said pharmaceutical composition comprising said non-undecanoate testosterone ester.

2. The method of claim 1, wherein when exposed to about 1000 mL of 2% w/v Triton X-100 in an aqueous media maintained at about 37±1° C. in a USP-Type II dissolution apparatus set at 100 rpm, said pharmaceutical composition exhibits an in vitro release rate of said non-undecanoate testosterone ester of at least one of at least about 45% during about 60 minutes, at least about 75% during about the first 120 minutes, and at least about 90% during about 4 hours.

3. The method of claim 1, wherein said at least one dose of said initial dosage comprises a total equivalent amount of androst-4-en-17β-ol-3-one of from about 250 mg to about 893 mg.

4. The method of claim 1, wherein said pharmaceutical composition comprises at least one of (17-β)-3-oxoandrost-4-en-17-yl tridecanoate, (17-β)-3-oxoandrost-4-en-17-yl dodecanoate, and a combination thereof.

5. The method of claim 3, wherein said total equivalent amount of androst-4-en-17β-ol-3-one comprises at least 25 w/w % of said non-undecanoate testosterone ester.

6. The method of claim 4, wherein said at least one dose of said initial dosage comprises from about 50 mg to about 1500 mg of said non-undecanoate testosterone ester.

7. The method of claim 1, wherein at least one of said at least one dose of said initial dosage and said at least one dose of said maintenance dosage comprises a once daily dose.

8. The method of claim 1, wherein said non-undecanoate testosterone ester comprises at least one of substantially non-crystalline non-undecanoate testosterone ester and substantially solubilized non-undecanoate testosterone ester.

9. The method of claim 1, wherein if said androst-4-en-17β-ol-3-one serum concentration level exceeds a predetermined level, said at least one dose of said maintenance dosage subceeds at least one previously administered dose, and wherein if said androst-4-en-17β-ol-3-one serum concentration level subceeds a predetermined level, said at least one dose of said maintenance dosage exceeds at least one previously administered dose, and wherein if said androst-4-en-17β-ol-3-one serum concentration level is within a predetermined range, an amount of said at least one dose of said maintenance dosage is substantially identical to the amount of at least one previously administered dose.

10. The method of claim 1, wherein if said androst-4-en-17β-ol-3-one serum concentration level exceeds a predetermined level, said at least one dose of said maintenance dosage is decreased by from about 76 mg of equivalent amount of androst-4-en-17β-ol-3-one to about 0.5 times at least one previously administered dose, and wherein if said androst-4-en-17β-ol-3-one serum concentration level subceeds a predetermined level, said at least one dose of said maintenance dosage is increased by from about 76 mg of equivalent amount of androst-4-en-17β-ol-3-one to about 2.0 times at least one previously administered dose, and wherein if said androst-4-en-17β-ol-3-one serum concentration level is within a predetermined range, said at least one dose of said maintenance dosage is not increased or decreased relative to at least one previously administered dose.

11. The method of claim 1, wherein if said androst-4-en-17β-ol-3-one serum concentration level exceeds a predetermined level, said at least one dose of said maintenance dosage is decreased by from about 20% to about 90% relative to at least one previously administered dose, and wherein if said androst-4-en-17β-ol-3-one serum concentration level subceeds a predetermined level, said at least one dose of said maintenance dosage is increased by from about 20% to about 100% relative to at least one previously administered dose, and wherein if said androst-4-en-17β-ol-3-one serum concentration level is within a predetermined range, said at least one dose of said maintenance dosage is not increased or decreased relative to at least one previously administered dose.

12. The method of claim 3, wherein if said androst-4-en-17β-ol-3-one serum concentration level exceeds a predetermined level, said at least one dose of said maintenance dosage is decreased by from about 20% to about 90% relative to at least one previously administered dose, and wherein if said androst-4-en-17β-ol-3-one serum concentration level subceeds a predetermined level, said at least one dose of said maintenance dosage is increased by from about 20% to about 100% relative to at least one previously administered dose, and wherein if said androst-4-en-17β-ol-3-one serum concentration level is within a predetermined range, said at least one dose of said maintenance dosage is not increased or decreased relative to at least one previously administered dose.

13. The method of claim 1, wherein said androst-4-en-17β-ol-3-one serum concentration level is obtained by measuring said androst-4-en-17β-ol-3-one serum concentration level at a single point from about 4 hours to about 18 hours after at least one previously administered single dose.

14. The method of claim 1, wherein said androst-4-en-17β-ol-3-one serum concentration level is obtained from a single point measurement.

15. The method of claim 1, wherein based on a group of at least 24 hypogonadal males, said method provides an androst-4-en-17β-ol-3-one serum concentration $C_{avg}$ in the eugonadal range in at least 75% of said group after at least one of achievement of a steady state serum concentration level and at least 7 days from at least one previously administered dose of said pharmaceutical composition.

16. The method of claim 1, wherein said method comprises obtaining a plurality of androst-4-en-17β-ol-3-one serum concentration levels of said subject and administering a plurality of maintenance dosages.

17. The method of claim 1, wherein:
if said at least one dose of said initial dosage comprises an equivalent amount of androst-4-en-17β-ol-3-one of about 300 mg plus/minus 50 mg and said serum concentration level measured post-administration is greater than a predetermined level, then said at least one dose of said maintenance dosage comprises an equivalent amount of androst-4-en-17β-ol-3-one of about 150 mg plus/minus 37.5 mg, and if said at least one dose of said initial dosage comprises an equivalent amount of androst-4-en-17β-ol-3-one of about 300 mg plus/minus 50 mg and said serum concentration level measured post-administration is less than a predetermined level, then said at least one dose of said maintenance dosage comprises an equivalent amount of androst-4-en-17β-ol-3-one of about 450 mg plus/minus 112.5 mg, and if said at least one dose of said initial dosage comprises an equivalent amount of androst-4-en-17β-ol-3-one of about 400 mg plus/minus 50 mg and said serum concentration level measured post-administration is greater than a predetermined level, then said at least one dose of said maintenance dosage comprises an equivalent amount of androst-4-en-17β-ol-3-one of about 200 mg plus/minus 50 mg, and if said at least one dose of said initial dosage comprises an equivalent amount of androst-4-en-17β-ol-3-one of about 400 mg plus/minus 50 mg and said serum concentration level measured post-administration is less than a predetermined level, then said at least one dose of said maintenance dosage comprises an equivalent amount of androst-4-en-17β-ol-3-one of about 600 mg plus/minus 150 mg, and if said at least one dose of said initial dosage comprises an equivalent amount of androst-4-en-17β-ol-3-one of about 450 mg plus/minus 60 mg and said serum concentration level measured post-administration is greater than a predetermined level, then said at least one dose of said maintenance dosage comprises an equivalent amount of androst-4-en-17β-ol-3-one of about 300 mg plus/minus 75 mg, and if said at least one dose of said initial dosage comprises an equivalent amount of androst-4-en-17β-ol-3-one of about 450 mg plus/minus 60 mg and said serum concentration level measured post-administration is less than a predetermined level, then said at least one dose of said maintenance dosage comprises an equivalent amount of androst-4-en-17β-ol-3-one of about 600 mg plus/minus 150 mg, and if said at least one dose of said initial dosage comprises an equivalent amount of androst-4-en-17β-ol-3-one of about 600 mg plus/minus 100 mg and said serum concentration level measured post-administration is greater than a predetermined level, then said at least one dose of said maintenance dosage comprises an equivalent amount of androst-4-en-17β-ol-3-one of at least one of about 400 mg plus/minus 100 mg and about 450 mg plus/minus 112.5 mg, and if said at least one dose of said initial dosage comprises an equivalent amount of androst-4-en-17β-ol-3-one of about 600 mg plus/minus 100 mg and said serum concentration level measured post-administration is less than a predetermined level, then said at least one dose of said maintenance dosage comprises an equivalent amount of androst-4-en-17β-ol-3-one of at least one of about 750 mg plus/minus 187.5 mg and about 800 mg plus/minus 200 mg.

18. The method of claim 17, wherein said pharmaceutical composition comprising said non-undecanoate testosterone ester comprises at least one of a substantially non-crystalline form and a substantially solubilized form.

19. The method of claim 17, wherein said administration of said at least one maintenance dosage in a group of at least 24 subjects results in a post-titration $C_{avg}$ in the normal range for at least 75% of said group and a $C_{max}$ of greater than 2.5×ULN in no more than 3% of said group.

20. The method of claim 1, wherein said administration of said at least one maintenance dosage in a group of at least 24 subjects results in a post-titration $C_{avg}$ in the normal range for at least 75% of said group and a $C_{max}$ of greater than 2.5×ULN in no more than 3% of said group.

21. The method of claim 18, wherein said at least one dose of said initial dosage comprises an equivalent amount of androst-4-en-17β-ol-3-one of at least one of about 300 mg plus/minus 50 mg, about 400 mg plus/minus 50 mg, about 450 mg plus/minus 60 mg, about 600 mg plus/minus 100 mg, and about 750 mg plus/minus 112.5 mg.

22. The method of claim 1, wherein if said androst-4-en-17β-ol-3-one serum concentration level exceeds a predetermined level, said at least one dose of said maintenance dosage subceeds said at least one dose of said initial dosage, and wherein if said androst-4-en-17β-ol-3-one serum concentration level subceeds a predetermined level, said at least one dose of said maintenance dosage exceeds said at least one dose of said initial dosage, and wherein if said androst-4-en-17β-ol-3-one serum concentration level is within a predetermined range, an amount of said at least one dose of said maintenance dosage is substantially identical to the amount of at least one previously administered dose.

23. The method of claim 1, wherein said method is limited to at least one of the following constraints comprising:

wherein if said androst-4-en-17β-ol-3-one serum concentration level exceeds a predetermined level, said at least one dose of said maintenance dosage subceeds said at least one dose of said initial dosage, and wherein if said androst-4-en-17β-ol-3-one serum concentration level subceeds a predetermined level, said at least one dose of said maintenance dosage exceeds said at least one dose of said initial dosage, and wherein if said androst-4-en-17β-ol-3-one serum concentration level is within a predetermined range, an amount of said at least one dose of said maintenance dosage is substantially identical to the amount of at least one previously administered dose, wherein said at least one maintenance dosage is administered for a plurality of days, and wherein if said androst-4-en-17β-ol-3-one serum concentration level exceeds a predetermined level, said at least one dose of said maintenance dosage is decreased by from about 20% to about 90% relative to at least one previously administered dose, and wherein if said androst-4-en-17β-ol-3-one serum concentration level subceeds a predetermined level, said at least one dose of said maintenance dosage is increased by from about 20% to about 100% relative to at least one previously administered dose, and wherein if said androst-4-en-17β-ol-3-one serum concentration level is within a predetermined range, said at least one dose of said maintenance dosage is not increased or decreased relative to at least one previously administered dose, wherein if after administration of said at least one dose of said initial dosage, a steady state androst-4-en-17β-ol-3-one serum concentration level of said subject exceeds a predetermined level, said at least one dose of said maintenance dosage subceeds said at least one dose of said initial dosage, and wherein if a steady state androst-4-en-17β-ol-3-one serum concentration level of said subject subceeds a predetermined level, said at least one dose of said maintenance dosage exceeds said at least one dose of said initial dosage, and wherein if a steady state androst-4-en-17β-ol-3-one serum concentration level is within a predetermined range, an amount of said at least one dose of said maintenance dosage is substantially identical to the amount of at least one previously administered dose, and wherein said administration results in a $C_{avg}$ responder rate that is greater than a $C_{avg}$ responder rate of an administration to subjects of a substantially similar but untitrated dosage regimen of a pharmaceutical composition comprising a non-undecanoate testosterone ester, and wherein said treatment regimen comprises a titration dosage regimen, and wherein said administration of said titration dosage regimen results in a $C_{avg}$ responder rate that is greater than a $C_{avg}$ responder rate of an administration to subjects of a substantially similar but untitrated dosage regimen of a pharmaceutical composition comprising a non-undecanoate testosterone ester.

24. The method of claim 22, wherein said at least one dose of said initial dosage comprises a total equivalent amount of androst-4-en-17β-ol-3-one of from about 250 mg to about 893 mg.

25. The method of claim 22, wherein said pharmaceutical composition comprises at least one of (17-β)-3-oxoandrost-4-en-17-yl tridecanoate, (17-β)-3-oxoandrost-4-en-17-yl dodecanoate, and a combination thereof.

26. The method of claim 22, wherein said total equivalent amount of androst-4-en-17β-ol-3-one comprises at least 25 w/w % of said non-undecanoate testosterone ester.

27. The method of claim 22, wherein said at least one dose of said initial dosage comprises from about 50 mg to about 1500 mg of said non-undecanoate testosterone ester.

28. The method of claim 22, wherein at least one of said at least one dose of said initial dosage and said at least one dose of said maintenance dosage comprises a once daily dose.

29. The method of claim 22, wherein said non-undecanoate testosterone ester comprises at least one of substantially noncrystalline non-undecanoate testosterone ester and substantially solubilized non-undecanoate testosterone ester.

30. The method of claim 22, wherein if said androst-4-en-17β-ol-3-one serum concentration level exceeds a predetermined level, said at least one dose of said maintenance dosage is decreased by from about 76 mg of equivalent amount of androst-4-en-17β-ol-3-one to about 0.5 times at least one previously administered dose, and wherein if said androst-4-en-17β-ol-3-one serum concentration level subceeds a predetermined level, said at least one dose of said maintenance dosage is increased by from about 76 mg of equivalent amount of androst-4-en-17β-ol-3-one to about 2.0 times at least one previously administered dose, and wherein if said androst-4-en-17β-ol-3-one serum concentration level is within a predetermined range, said at least one dose of said maintenance dosage is not increased or decreased relative to at least one previously administered dose.

31. The method of claim 22, wherein if said androst-4-en-17β-ol-3-one serum concentration level exceeds a predetermined level, said at least one dose of said maintenance dosage is decreased by from about 20% to about 90% relative to at least one previously administered dose, and wherein if said androst-4-en-17β-ol-3-one serum concentration level subceeds a predetermined level, said at least one dose of said maintenance dosage is increased by from about 20% to about 100% relative to at least one previously administered dose, and wherein if said androst-4-en-17β-ol-3-one serum concentration level is within a predetermined range, said at least one dose of said maintenance dosage is not increased or decreased relative to at least one previously administered dose.

\* \* \* \* \*